US010335048B2

(12) United States Patent
Rooney et al.

(10) Patent No.: US 10,335,048 B2
(45) Date of Patent: Jul. 2, 2019

(54) HIGH-RESOLUTION METABOLIC NEUROIMAGING

(71) Applicants: William Rooney, Lake Oswego, OR (US); Charles Springer, Jr., Portland, OR (US); Xin Li, Beaverton, OR (US)

(72) Inventors: William Rooney, Lake Oswego, OR (US); Charles Springer, Jr., Portland, OR (US); Xin Li, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 976 days.

(21) Appl. No.: 14/543,071

(22) Filed: Nov. 17, 2014

(65) Prior Publication Data

US 2015/0141804 A1    May 21, 2015

Related U.S. Application Data

(60) Provisional application No. 61/904,943, filed on Nov. 15, 2013.

(51) Int. Cl.
*A61B 5/055*  (2006.01)
*A61B 5/0265* (2006.01)
(Continued)

(52) U.S. Cl.
CPC .......... *A61B 5/0263* (2013.01); *A61B 5/0013* (2013.01); *A61B 5/0037* (2013.01);
(Continued)

(58) Field of Classification Search
CPC ... A61B 5/0037; A61B 5/4076; A61B 5/4082; A61B 5/0263; A61B 5/0013; G01R 33/56366; G01R 33/56341
See application file for complete search history.

(56) References Cited

U.S. PATENT DOCUMENTS

2013/0129168 A1    5/2013  Ross
2013/0154638 A1    6/2013  Jena
(Continued)

FOREIGN PATENT DOCUMENTS

WO    2010-051065 A1    5/2010
WO    2013-159111 A1    10/2013

OTHER PUBLICATIONS

Anderson et al., "The Blood-Brain Barrier and Microvascular Water Exchange in Alzheimer's Disease" Cardiovascular Phsychiatry and Neurology, vol. 2011, Article ID 615829, 9 pages.*
(Continued)

*Primary Examiner* — Amelie R Gillman
*Assistant Examiner* — Colin T. Sakamoto
(74) *Attorney, Agent, or Firm* — Schwabe, Williamson & Wyatt, P.C.

(57) ABSTRACT

Provided herein are methods and apparatuses for determining a level of cellular metabolic activity for a region of interest in order to detect and map on-going gliovascular unit metabolic activity using high-resolution $^1H_2O$ MRI. In one example approach, a computer-implemented method includes receiving a first set of DCE-MRI time-course data for a region, wherein a contrast agent is administered prior to imaging, identifying a region of interest from the first set of DCE-MRI time-course data for further analysis, performing shutter-speed pharmacokinetic analysis of the time-course data associated with the region of interest using computer-implemented software to obtain a finite and non-zero mean water molecule capillary lifetime in the region of interest, and indicating a level of cellular metabolic activity in the brain based on the mean water molecule capillary lifetime.

16 Claims, 13 Drawing Sheets

(51) Int. Cl.
    G01R 33/563    (2006.01)
    A61B 5/0295    (2006.01)
    A61B 5/026     (2006.01)
    A61B 5/00      (2006.01)
    G01R 33/48     (2006.01)
    G01R 33/50     (2006.01)
    G01R 33/56     (2006.01)

(52) U.S. Cl.
    CPC .......... *A61B 5/0295* (2013.01); *A61B 5/4082* (2013.01); *A61B 5/4088* (2013.01); *A61B 5/7282* (2013.01); *A61B 5/742* (2013.01); *G01R 33/4828* (2013.01); *G01R 33/56366* (2013.01); *A61B 5/055* (2013.01); *A61B 5/4064* (2013.01); *A61B 5/4866* (2013.01); *A61B 5/748* (2013.01); *G01R 33/5601* (2013.01); *G01R 33/5608* (2013.01)

(56) References Cited

U.S. PATENT DOCUMENTS

2013/0211247 A1    8/2013    Kalafut
2014/0058249 A1    2/2014    Li et al.

OTHER PUBLICATIONS

Li et al., "Shutter-Speed Analysis of Contrast Reagent Bolus-Tracking Data: Preliminary Observations in Benign and Malignant Breast Disease" Magnetic Resonance in Medicine, vol. 53, Issue 3, (2005), pp. 724-729.*

Ennis et al., "Mechanisms of Sodium Transport at the Blood-Brain Barrier Studied with In Situ Perfusion of Rat Brain" Journal of Neurochemistry, vol. 66, No. 2 1996.*

Yang et al., "Edema, Cation Content, and ATPase Activity After Middle Cerebral Artery Occlusion in Rats" Stroke, vol. 23, No. 9, 1992.*

Harik "Blood-brain barrier sodium/potassium pump: Modulation by central noradrenergic innervation", Proceedings of the National Academies of Science, vol. 83, (1986) pp. 4067-4070.*

Kiselev et al., "Vessel Size Imaging in Humans", Magnetic Resonance Imaging in Medicine 53: 553-563 (2005).*

Gjedde et al., Neurokinetics: The Dynamics of Neurobiology in Vivo (2011), Chapter 2 Fundamentals of Compartment Kinetics, pp. 23-101.*

Litjens et al., "Pharmacokinetic Models in Clinical Practice: What Model to Use for DCR-MRI of the Breast?" 2010 IEEE International Symposium on Biomedical Imaging: From Nano to Macro, 2010 (Year: 2010).*

Zhang et al., "Active Trans-Plasma Membrane Water Cycling in Yeast Is Revealed by NMR" Biophysical Journal vol. 101 Dec. 2011 2833-2842 (Year: 2011).*

Yankeelov et al., Variation of the Relaxographic "Shutter-Speed" for Transcytolemmal Water Exchange Affects the CR Bolus-Tracking Curve Shape, Magnetic Resonance in Medicine, 50:1151-1169 (2003).

Yankeelov et al., Evidence for shutter-speed variation in CR bolus-tracking studies of human pathology, NMR in Biomedicine, 2005, 18, pp. 173-185.

Zhang et al., Active Trans-Plasina Membrane Water Cycling in Yeast is Revealed by NMR, Biophysical Journal, vol. 101, Dec, 2011, pp. 2833-2842.

Zhang et al., Intracellular Water Lifetime Depends on Cellular Energetic State, Biophysical Journal, 764-Pos, Board B643, p. 148a, Mar. 1, 2009.

Zhou et al., DCE MRI Detected Differential Response to ZD6126 of Metastatic versus Indolent Human Melanoma, Proc. Intl. Soc. Mag. Reson. Med., 14, 2006, p. 2911.

Zhang et al., Nano-Osmotic Coupling in Active Cell Membrane Water Permeability, Proc. Intl. Soc. Mag. Reson. Med., 19, 2011, p. 3457.

International Preliminary Report on Patentability, PCT/US2014/065924.

International Search Report and Written Opinion, PCT/US2014/065924.

Li et al., Implications of Mean Intracellular Water Lifetime for Prostate DCE-MRI Modeling, Proc. Intl. Soc. Mag. Reson. Med. 19 (2011), p. 3115.

Huang et al., The magnetic resonance shutter speed discriminates vascular properties of malignant and benign breast tumors in vivo, PNAS, Nov. 18, 2009, vol. 105, No. 46, pp. 17943-17948.

Tofts et al., Estimating Kinetic Parameters From Dynamic Contrast-Enhanced T1-Weighted MRI of a Diffusable Tracer: Standardized Quantities and Symbols, J Magn Res Imag. 1999, vol. 10, pp. 223-232.

Li et al., Shutter-Speed Analysis of Contrast Reagent Bolus-Tracking Data: Preliminary Observations in Benign and Malignant Breast Disease, Magnetic Resonance in Medicine, 2005, vol. 53, Iss. 3, pp. 724-729.

Li et al., NMR Shutter-Speed Discrimination of Malignant and Benign Breast Tumors Using ROI Data, Proceedings of the International Society for Magnetic Resonance in Medicine 16th, International Society for Magnetic Resonance in Medicine, USA, May 3, 2008, p. 3830.

* cited by examiner

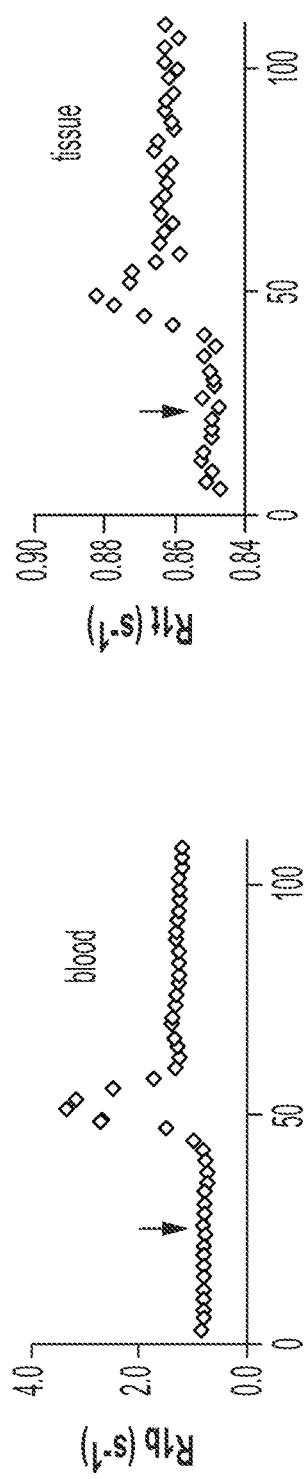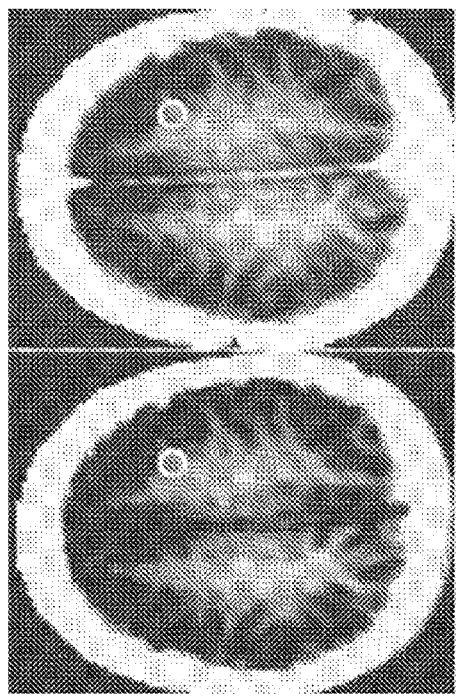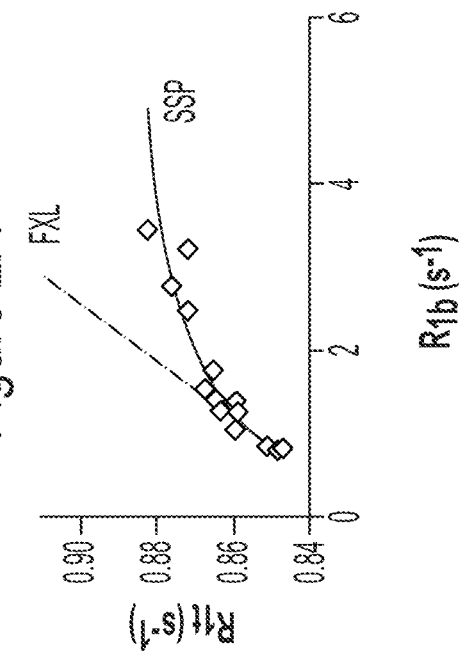
Figure 2A
Figure 2B
Figure 2C
Figure 2D

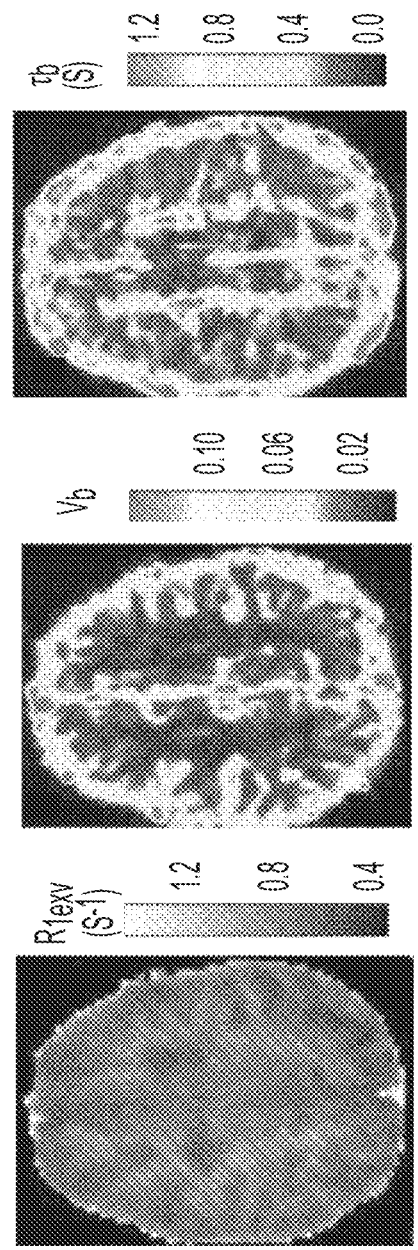

HIGH-RESOLUTION METABOLIC NEUROIMAGING

CROSS REFERENCE TO RELATED APPLICATIONS

The present application claims priority to U.S. Provisional Patent Application No. 61/904,943, filed Nov. 15, 2013, entitled "HIGH-RESOLUTION METABOLIC NEUROIMAGING," the entire disclosure of which is hereby incorporated by reference in its entirety.

ACKNOWLEDGEMENT OF GOVERNMENT SUPPORT

This invention was made with Government support under Grant Nos. R01-EB007258, R01-NS40801, and U01 CA-154602 awarded by The National Institutes of Health. The United States Government has certain rights in the invention.

FIELD

Embodiments herein relate to identification of tissue, and, more specifically, to methods and apparatuses of using magnetic resonance imaging for tissue identification, phenotyping, and monitoring.

BACKGROUND

The ability to map cerebral metabolic activity is important for diagnosis and therapy monitoring of numerous neurological disorders, including but not limited to Alzheimer's disease and other senile dementias, Huntington's disease, Parkinson's disease, multiple sclerosis, and brain tumors. Cerebral metabolic imaging typically requires the administration of a radio labeled sugar analog which is invasive and limits the spatial resolution attainable.

Metabolic imaging can be defined as mapping the distributions of metabolic molecule tissue concentrations ("levels") and/or metabolic fluxes: the metabolic thermodynamic and kinetic aspects, respectively. Metabolic imaging has the potential for early disease detection and therapy monitoring on an individualized basis. Metabolic imaging may be accomplished by positron emission tomography [PET], magnetic resonance spectroscopic imaging [MRSI], and with some effort also by single photon emission computed tomography [SPECT]. However, various problems arise with such approaches and improvements are sought. For example, the PET and HP-$^{13}$CMRSI modalities are costly. Typical nominal spatial resolutions and voxel volumes for the human metabolic imaging modalities are: $^{31}$PMRSI [(1.3 cm)$^3$=2.2 mL]; SPECT [(1 cm)$^3$=1 mL], HP-$^{13}$CMRSI [(7 mm)$^3$=340 µL]; PET [(5 mm)$^3$=125 µL]; and $^{23}$NaMRSI [(4 mm)$^3$=64 µL] [see M. Inglese, G. Madelin, N. Oesingmann, J. S. Babb, W. Wu, B. Stoekel, J. Herbert, G. Johnson, "Brain Tissue Sodium Concentration in Multiple Sclerosis: A Sodium Imaging Study at 3 Tesla," *Brain* 133, 847-857 (2010), hereby incorporated by reference herein in its entirety]. Such approaches are often insufficient for discriminating significant human anatomy. For example, the cerebral gray matter (GM)/white matter (WM) boundary usually cannot be distinguished. In comparison, MRI generated from the relatively strong $^1$H$_2$O signal routinely offers substantially higher spatial resolution; (1 mm)$^3$=1 µL, or better. Modern metabolic images are almost always accompanied by high-resolution MRI [and sometimes computed tomography (CT)] views of the same tissue. Understandably therefore, MRI is often thought of as providing only anatomical information with the exceptions of tissue function in some cases such as functional MRI and cine cardiovascular MR. Compared with PET and HP-$^{13}$CMRSI, MRI is relatively inexpensive. Also, MRI employs no ionizing radiation.

SUMMARY

Disclosed in various embodiments are computer-implemented methods for determining a level of cellular metabolic activity for a region of interest in order to detect and map on-going gliovascular unit metabolic activity using high-resolution $^1$H$_2$O MRI. Embodiments are disclosed which detect gliovascular unit metabolic activity using only repeated, non-selective RF$^1$H$_2$O magnetization perturbation before, during, and after the minimally invasive IV injection of approved doses of any of several very common clinical contrast agents (CAs). In particular, embodiments disclosed describe an MRI-based approach that utilizes contrast agents and shutter-speed pharmacokinetic modeling to calculate regional metabolic activity based on intravascular water lifetime measurement. The primary advantages of such approaches compared to existing techniques include: higher spatial resolution, substantially lower cost, less invasive procedures and data acquisition, and greater dispersion and accessibility of MRI instruments.

In various embodiments, the method may include receiving a first set of Dynamic Contrast Enhanced MRI (DCE-MRI) time-course data for a region, wherein a contrast agent (imaging dye) is administered during multi-frame imaging, identifying a region of interest from the first set of DCE-MRI time-course data for further analysis, performing shutter-speed pharmacokinetic analysis of the time-course data associated with the region of interest using computer-implemented software to obtain a finite and non-zero mean water molecule capillary lifetime ($\tau_b$) in the region of interest, and indicating a level of cellular metabolic activity in the brain based on the mean water molecule capillary lifetime. For example, in embodiments the cellular metabolic activity may comprise Na$^+$/K$^+$ ATPase activity which is negatively correlated with mean water molecule capillary lifetime. Further, in some embodiments, indicating a cerebral pathology based on the mean water molecule capillary lifetime may comprise indicating a multiple sclerosis condition based on the level of cellular metabolic activity in the brain as determined based on the mean water molecule capillary lifetime.

It should be understood that the summary above is provided to introduce in simplified form a selection of concepts that are further described in the detailed description. It is not meant to identify key or essential features of the disclosed subject matter. Furthermore, the disclosed subject matter is not limited to implementations that solve any disadvantages noted above or in any part of this disclosure.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 2 shows example 7 T $^1H_2O$ DCE-MRI data from a 22 y F control subject.

FIG. 9 shows example SSP parametric maps for a 52 y F RRMS subject.

DETAILED DESCRIPTION

Figure 1:
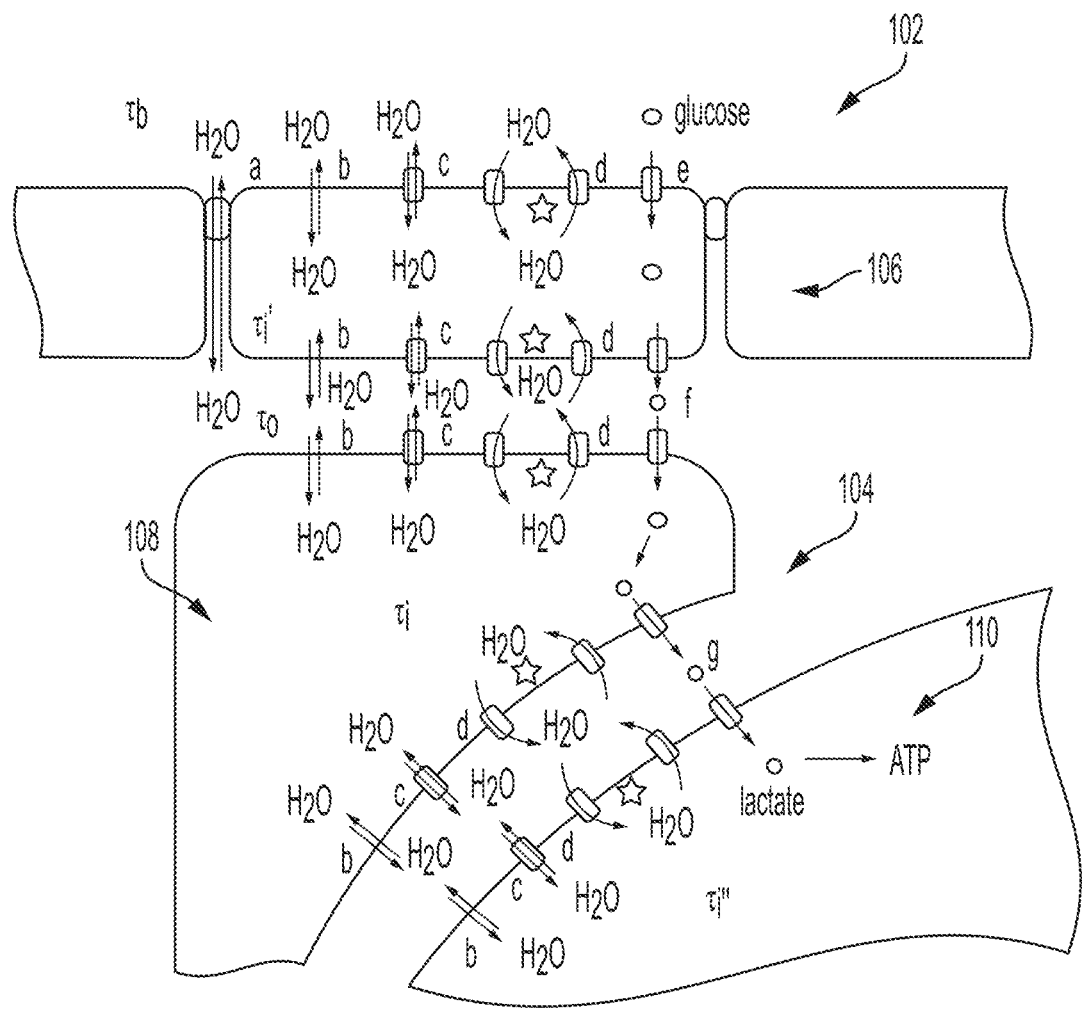
FIG. 1 illustrates gliovascular unit water exchange mechanisms determining mean water molecule lifetimes in blood.

In the following detailed description, reference is made to the accompanying drawings that form a part hereof and in which is shown by way of illustration embodiments in which the invention may be practiced. It is to be understood that other embodiments may be utilized and structural or logical changes may be made without departing from the scope of the present disclosure. Therefore, the following detailed description is not to be taken in a limiting sense, and the scope of embodiments in accordance with the present disclosure is defined by the appended claims and their equivalents. Throughout this disclosure, each cited reference/publication is hereby incorporated by reference herein in its entirety.

Various operations may be described as multiple discrete operations in turn, in a manner that may be helpful in understanding embodiments of the present invention; however, the order of description should not be construed to imply that these operations are order dependent. The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

The following abbreviations are used throughout this disclosure: ADP, adenosine diphosphate; ASL, arterial spin label; ATP, adenosine triphosphate; CA, contrast agent; CBV, cerebral blood volume; CESL/CEST, chemical exchange spin lock/saturation transfer; $CMR_{oxphos}$, cerebral metabolic rate of ATP synthesis from oxidative phosphorylation; DCE-MRI, dynamic-contrast-enhanced magnetic resonance imaging; F, cerebral blood flow (CBF); FDG, fluorodeoxyglucose; Fe-tol, ferumoxytol (Feraheme); FOV, field-of-view; FXL, fast-exchange-limit; FXR, fast-exchange-regime; GBM, glioblastoma multiforme; GBM-NA, GBM normal appearing; GdHPDO3A, gadoteridol (ProHance); GM, gray matter; GRE-EPI, gradient recalled echo-echo planar imaging; HEP, high energy phosphate; HP, hyperpolarized; IR, inversion recovery; $MR_{glc}$, metabolic rate of glucose (consumption); MRSI, magnetic resonance spectroscopic imaging; MS, multiple sclerosis; MS-NA, MS normal appearing; MT, magnetization transfer; NGM, normal GM; NKA, Na$^+$,K$^+$-ATPase; NWM, normal WM; PCr, phosphocreatine; PET, positron emission tomography; $P_i$, inorganic phosphate (PO$_4^{3-}$); rCBV relative CBV; RF, radiofrequency; ROI, region-of-interest; RRMS, relapsing-remitting-MS; SPECT, single photon emission computed tomography; SPMS, secondary-progressing MS; SSP, shutter-speed paradigm; SXR, slow-exchange-regime; TI, inversion time; TP, tracer paradigm; TSC, tissue sodium concentration; WEI, water exchange index; WM, white matter; 2SX, two-site exchange.

In various embodiments, methods, apparatuses, and systems using magnetic resonance imaging for tissue identification are provided. In exemplary embodiments, a computing device may be endowed with one or more components of the disclosed apparatuses and/or systems and may be employed to perform one or more methods as disclosed herein.

Embodiments herein provide a Magnetic Resonance Imaging (MRI) technique and optionally newly developed software, collectively referred to as the "shutter-speed" model, to analyze image data of cancer patients. Embodiments provide a minimally invasive, yet precisely accurate, approach to identify levels of cellular metabolic activity and identify cerebral pathologies.

In embodiments, a computer-implemented method for quantifying on-going cellular metabolic activity for a region of interest in a brain is provided. In one example approach, a method according to various embodiments may comprise receiving a first set of DCE-MRI time-course data for a region, wherein a contrast agent is administered prior to imaging; identifying a region of interest from the first set of DCE-MRI time-course data for further analysis; performing shutter-speed pharmacokinetic analysis of the time-course data associated with the region of interest using computer-implemented software to obtain a first finite and non-zero mean water molecule capillary lifetime in the region of interest; and indicating a level of cellular metabolic activity in the brain based on the mean water molecule capillary lifetime. For example, the cellular metabolic activity may comprise Na$^+$/K$^+$ ATPase activity.

A method according to various embodiments may further comprise correlating increasing mean water molecule capillary lifetimes with decreasing Na$^+$/K$^+$ ATPase activities, and in response to the water molecule capillary lifetime increased by an amount relative to a threshold, indicating a decrease of Na$^+$/K$^+$ ATPase activity by the amount, and in response to the water molecule capillary lifetime decreased by an amount relative to the threshold, indicating an increase of Na$^+$/K$^+$ ATPase activity by the amount.

In some embodiments, a map of the region of interest based on the inverse of mean water molecule capillary lifetime may generated and output to a display device.

A method according to various embodiments may further comprise performing shutter-speed pharmacokinetic analysis of time-course data associated with a region of interest using computer-implemented software to obtain a blood volume fraction. In some examples, individual capillary radii may be estimated based on blood volume fraction. Additionally, in some embodiments, an equilibrium water efflux from brain capillaries in the region of interest may be calculated based on an estimated average capillary length and radius and the mean water molecule capillary lifetime.

A method according to various embodiments may further comprise receiving a second set of DCE-MRI time-course data for the region of interest, wherein the second set of DCE-MRI time-course data is obtained after the region has been treated; performing shutter-speed pharmacokinetic analysis of the second set of time-course data associated with the region of interest using computer-implemented software to obtain a second finite and non-zero mean water molecule capillary lifetime in the region of interest; determining a level of cellular metabolic activity in the brain based on the second mean water molecule capillary lifetime; and indicating a difference between the level of cellular metabolic activity in the brain based on the first mean water molecule capillary lifetime and the level of cellular metabolic activity in the brain based on the second mean water molecule capillary lifetime. In some examples, a cerebral pathology may be indicated based on the mean water molecule capillary lifetime. For example, a glioblastoma multiforme condition may be indicated based on the level of cellular metabolic activity in the brain.

As another example, a multiple sclerosis condition may be indicated based on the level of cellular metabolic activity in the brain. In this example, methods according to various embodiments may further comprise indicating a first multiple sclerosis brain condition in response to the mean water molecule capillary lifetime greater than a first threshold and indicating a second multiple sclerosis brain condition in response to the mean water molecule capillary lifetime greater than a second threshold, where the second threshold is larger than the first threshold. For example, the first multiple sclerosis brain condition may comprise a normal-appearing multiple sclerosis brain condition and the second multiple sclerosis brain condition may comprise a multiple sclerosis lesion condition and/or a glioblastoma multiforme tumor condition. Additionally, method described herein may be used to indicate an advanced stage multiple sclerosis brain condition in response to the mean water molecule capillary lifetime less than a third threshold, where the third threshold is less than the first threshold.

In embodiments, the mean water molecule capillary lifetime in the region of interest may be obtained via non-linear modeling and the cellular metabolic activity may comprise neuroglial and/or neuronal metabolic activity.

Additionally, in embodiments a computer-implemented method for quantifying cellular metabolic activity for a region of interest in a heart is provided. In one example approach, a method according to various embodiments may comprise receiving a first set of DCE-MRI time-course data for a region, wherein a contrast agent is administered prior to imaging; identifying a region of interest from the first set of DCE-MRI time-course data for further analysis; performing shutter-speed pharmacokinetic analysis of the time-course data associated with the region of interest using computer-implemented software to obtain a first non-zero and finite mean intracellular water molecule lifetime in the region of interest; and indicating a level of cellular metabolic activity in the heart based on the mean intracellular water molecule lifetime.

A method according to various embodiments may further comprise receiving a second set of DCE-MRI time-course data for the region of interest, wherein the second set of DCE-MRI time-course data is obtained after the region has been treated; performing shutter-speed pharmacokinetic analysis of the second set of time-course data associated with the region of interest using computer-implemented software to obtain a second non-zero and finite mean intracellular water molecule lifetime in the region of interest; determining a level of cellular metabolic activity in the heart based on the second mean intracellular water molecule lifetime; and indicating a difference between the level of cellular metabolic activity in the heart based on the first mean intracellular water molecule lifetime and the level of cellular metabolic activity in the heart based on the second mean intracellular water molecule lifetime. For example, a heart disease condition may be indicated in response to the mean intracellular water molecule lifetime greater than a threshold. Additionally, a map of the region of interest based on the mean intracellular water molecule lifetime in the region of interest may be generated and output to a display device.

As background, every eukaryotic cell has a plasma membrane P-type ATPase ion pump; for animals, this is $Na^+,K^+$-ATPase [NKA] (see Bublitz M, Morth J P, Nissen P. P-type ATPases at a glance. J. Cell. Sci. 2011; 124: 2515-2519; Morth J P, Pedersen B P, Buch-Pedersen M J, Anderson J P, Vilsen B, Palmgren M G, Nissen P. A structural overview of the plasma membrane Na+,K+-ATPase and H+-ATPase ion pumps. Nature Rev., Mol. Cell. Biol. 2011; 12: 60-70). Since its activity maintains the trans-mural $K^+$ and $Na^+$ gradients and thus, respectively, the membrane potential and secondary active transport, NKA is vital for life. The normal "forward" reaction can be described by the following equation, where the i and o subscripts indicate intra- and extra-cellular, respectively.

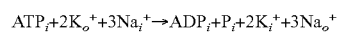

$$ATP_i + 2K_o^+ + 3Na_i^+ \rightarrow ADP_i + P_i + 2K_i^+ + 3Na_o^+$$

Even in homeostasis, the NKA pump experiences continual turnover [there are return pathways]. It has been estimated that it consumes over 50% of brain adenosine triphosphate [ATP] (Reinhard L, Tidow H, Clausen M J, Nissen P. Na+,K+-ATPase as a docking station: Protein-protein complexes of the Na+,K+-ATPase. Cell Mol. Life. Sci. 2013; 70: 205-222). Methods for measuring NKA activity have been adapted to the experimental sample. For solubilized, purified enzyme or tissue homogenate preparations, spectrophotometric or radiolabeled [$^{32}$P] ATP hydrolysis rate assays suffice (see Kutchai H, Geddis L M. Inhibition of the Na, K-ATPase of canine renal medulla by several local anesthetics. Pharmacol. Res. 2001; 43: 399-403; and Goldin S M. Active transport of sodium and potassium ions by the sodium and potassium ion-activated adenosine triphosphatase from renal medulla. J. Biol. Chem. 1977; 252: 5630-5642). For intact cells in culture or in tissue preparations, voltage clamp current, ion-selective [$Na^+/K^+$] microelectrode response, radioisotope [$^{22}Na^+/^{24}Na^+/^{42}K^+/^{86}Rb^+$] uptake/release, or $^{23}Na^+/^{87}Rb^+$ MR spectroscopic [MRS] methods measure NKA-driven trans-membrane ion transport kinetics (see Han F, Tucker A L, Lingrel J B, Despa S, Bers D M. Extracellular potassium dependence of the Na+-K+-ATPase in cardiac myocytes: Isoform specificity and effect on phospholemman. Am. J. Cell Physiol. 2009; 297: C699-C705; Wang W, Gao J, Entcheva E, Cohen I S, Gordon C, Mathias R T. A Transmural gradient in the cardiac Na/K Pump generates a transmural gradient in Na/Ca exchange. J. Membr. Biol. 2010; 233: 51-62; McCall D. Cation exchange and glycoside binding in cultured rat heart cells. Am. J. Physiol. 1979; 236: C87-C95; Garcia A, Fry N A, Karimi K, Liu C-C, Apell H-J, Rasmussen H H, Clarke R J. Extracellular allosteric $Na^+$ binding to the $Na^+,K^+$-ATPase in cardiac myocytes. Biophys. J. 2013; 105: 2695-2705; Jansen M A, Shen H, Zhang L, Wolkowicz P E, Balschi J A. Energy requirements for the Na⁺ gradient in the oxygenated isolated heart: Effect of changing the free energy of ATP hydrolysis. Am. J. Physiol. Heart Circ. Physiol. 2003; 285: H2437-H2445; and Kypriyanov V V, Stewart L C, Xiang B, Kwak J, Deslauriers R. Pathways of Rb+ influx and their relation to intracellular [Na+] in the perfused rat heart. Circ. Res. 1995; 76: 839-851). Phospholipid vesicles reconstituted with purified NKA allow measurement of both ATP hydrolysis and ion transport kinetics (Goldin S M. Active transport of sodium and potassium ions by the sodium and potassium ion-activated adenosine triphosphatase from renal medulla. J. Biol. Chem. 1977; 252: 5630-5642).

Each of these methods is best suited to macroscopically homogeneous samples. None are particularly appropriate for normally heterogeneous tissue, since there is no spatial encoding. Furthermore, many of these methods directly measure only net NKA activity, not homeostatic turnover. The radioisotope approach has been generally abandoned for ~20 years; deemed too problematic for even tissue preparations (Eisner D A, Smith T W. The Na—K pump and its effectors in cardiac muscle. In The Heart and Cardiovascular System (2nd Ed.), H. A. Fozzard, E. Haber, R. B. Jennings, and A. M. Katz, Eds. Raven Press, New York, 1992, Chap. 35, pp. 863-902). The inventors herein have recognized that NKA turnover may have never been measured, let alone mapped, in a living animal or human subject. The inventors herein have recognized that doing so would provide a very fundamental view of on-going metabolism, a new form of metabolic imaging. Since metabolic thermodynamics and kinetics have no necessary relationship, it is imperative to distinguish these aspects in imaging.

Mapping Metabolic Thermodynamics.

When restricted essentially to human subjects, current metabolic imaging has been mostly accomplished by positron emission tomography [PET] (Vallabhajosula S, Solnes L, Vallabhajosula B. A broad overview of positron emission tomography radiopharmaceuticals and clinical applications: What is new? Sem. Nucl. Med. 2011; 41: 246-264) and magnetic resonance spectroscopic imaging [MRSI] (Brindle K. Watching tumors gasp and die with MRI: The promise of hyperpolarized 13C MR spectroscopic imaging. Brit. J. Radiol. 2012; 85: 697 708; Nelson S J, Kurhanewicz J, Vigneron D B, Larson P E Z, Harzstark A L, Ferrone M, Van Criekinge M, Chang J W, Bok R, Park I, Reed G, Carvajal L, Small Et Munster P, Weinberg V K, Ardenkjaer-Larsen J H, Chen A P, Hurd R E, Odegardstuen L-I, Robb F J, Tropp J, Murray J A. Metabolic imaging of patients with prostate cancer using hyperpolarized [1-13C]pyruvate. Sci. Trans. Med. 2013; 5: 198ra108), with some single photon emission computed tomography [SPECT] (Khalil M M, Tremoleda J L, Bayomy T B, Gsell W. Molecular SPECT imaging: An overview. Int. J. Mol. Imag. 2011). Very often, this is mapping of metabolic molecule tissue concentrations ("levels")—the thermodynamic dimension of metabolism. For example, ³¹PMRSI gives the distribution of high-energy phosphate [HEP] brain levels (Zhu X-H, Qiao H, Du F, Xiong Q, Liu X, Zhang X, Ugurbil K, Chen W. Quantitative imaging of energy expenditure in human brain. Neuroimage. 2012; 60: 2107-2117). Such data could be used to estimate the cerebral distribution of the free energy for ATP hydrolysis (see Jansen M A, Shen H, Zhang L, Wolkowicz P E, Balschi J A. Energy requirements for the Na⁺ gradient in the oxygenated isolated heart: Effect of changing the free energy of ATP hydrolysis. Am. J. Physiol. Heart Circ. Physiol. 2003; 285: H2437-H2445; and Veech R L, Kashiwaya Y, Gates D N, King M T, Clarke K. The energetics of ion distribution: The origin of the resting electric potential of cells. Life 2002; 54: 241-252). ²³NaMRSI maps tissue sodium concentration [TSC] (Inglese M, Madelin G, Oesingmann N, Babb J S, Wu W, Stoekel B, Herbert J, Johnson G. Brain tissue sodium concentration in multiple sclerosis: A sodium imaging study at 3 Tesla. Brain 2010; 133: 847-857). A TSC increase often reflects an intracellular sodium, $Na_i^+$, increase [The Hillal Effect], a decrease in the transcytolemmal sodium electrochemical potential gradient. ¹HMRSI can map the lactate, N-acetylaspartate, and choline-containing metabolites (Haddadin I S, McIntosh A, Meisamy S, Corum C, Styczynski Snyder A L, Powell N J, Nelson M T, D. Yee D, Garwood M, Bolan P J. Metabolite quantification and high-field MRS in breast cancer. NMR Biomed 2009; 22: 65-76). Other thermodynamic aspects assessed include $H_3O^+$ (pH), $O_2$ [diminished in hypoxia], and redox level distributions (De Leon-Rodriguez L M, Lubag A J M, Malloy C R, Martinez G V, Gillies R J, Sherry A D. Responsive MRI agents for sensing metabolism in vivo. Acct. Chem. Res. 2009; 42: 948-957). Newer metabo-CESL/CEST [Chemical Exchange Spin Lock/Saturation Transfer] methods use radio frequency [RF] pulses to detect metabolite [creatine, glucose] resonances via the ¹$H_2O$ MR signal (see Haris M, Singh A, Cai K, Kogan F, McGarvey J, DeBrosse C, Zsido G A, Witschey W R T, Koomalsingh K, Pilla J J, Chirinos J A, Ferrari V A, Gorman J H, Hariharan H, Gorman R C, Reddy R. A technique for in vivo mapping of myocardial creatine kinase metabolism. Nat. Med. 2014; 20: 209-214; Walker-Samuel S, Ramasawmy R, Torrealdea F, Rega M, Rajkumar V, Johnson S P, Richardson S, Gongalves M, Parkes H G, Arstad E, Thomas D L, Pedley R B, Lythgoe M F, Golay X. In vivo imaging of glucose uptake and metabolism in tumors. Nat. Med. 2013; 19: 1067-1072; and Jin T, Mehrens H, Hendrich Kans., Kim S-G. Mapping brain glucose uptake with chemical exchange-sensitive spin-lock magnetic resonance imaging. J. Cereb. Blood Flow & Metabol. 2014; 34: 1402-1410). Though receptors aren't metabolites, PET and SPECT can be used to map their tissue concentrations (Logan J, Volkow N D, Fowler J S, Wang G-J, Fischman M W, Foltin R W, Abumrad N N, S. Vitkun S, Gatley S J, Pappas N, Hitzemann R, Shea C E. Concentration and occupancy of dopamine transporters in cocaine abusers with [11C]cocaine and PET. Synapse 1997; 27: 347-356; Krohn K A. The physical chemistry of ligand-receptor binding identifies some limitations to the analysis of receptor images. Nucl. Med. Biol. 2001; 28: 477-483). For example, the [¹¹C]cocaine tracer was used to determine the dopamine transporter concentration, 700 nM, in the abuser striatum. Receptors very often catalyze, or trigger by signaling, metabolic reactions.

Mapping Metabolic Kinetics.

For all the power of thermodynamics, kinetic metabolic aspects—enzyme-catalyzed fluxes [rates]—can be more informative. With PET and hyperpolarized ¹³CMRSI [HP-¹³CMRSI], a non-equilibrium isotope distribution [positron emitting isotope (e.g., in ¹⁸Fluorodeoxyglucose (¹⁸FDG)); hyperpolarized (stable) ¹³C isotope magnetization] is introduced exogenously, with minimal invasion. Then, the (relatively slow) regional approach to isotope equilibrium is mapped using spatially encoded detection. The evaluation of generally much faster steady-state ("equilibrium") unidirectional fluxes must be accomplished with proper modeling (see Brindle K. Watching tumors gasp and die with MRI: The promise of hyperpolarized 13C MR spectroscopic imaging. Brit. J. Radiol. 2012; 85: 697 708; Nelson S J, Kurhanewicz J, Vigneron D B, Larson P E Z, Harzstark A L, Ferrone M, Van Criekinge M, Chang J W, Bok R, Park I, Reed G, Carvajal L, Small E J, Munster P, Weinberg V K, Ardenkjaer-Larsen J H, Chen A P, Hurd R E, Odegardstuen L-I, Robb F J, Tropp J, Murray J A. Metabolic imaging of patients with prostate cancer using hyperpolarized [1-13C] pyruvate. Sci. Trans. Med. 2013; 5; Zhu X-H, Qiao H, Du F, Xiong Q, Liu X, Zhang X, Ugurbil K, Chen W. Quantitative imaging of energy expenditure in human brain. Neuroimage. 2012; 60: 2107-2117; Krohn K A, Mankoff D A, Muzi M, Link J M, Spence A M. True tracers: Comparing FDG with glucose and FLT with thymidine. Nucl. Med. Biol. 2005; 32: 663-671; and Krohn K A, Link J M. Interpreting enzyme and receptor kinetics: Keeping it simple, but not too simple. Nucl. Med. Biol. 2003; 30: 819-826). By far the most common example is the inference of the metabolic rate [consumption] of glucose, $MR_{glc}$ [in μmol/min/g], from the net metabolic rate [uptake] of $^{18}$FDG. In the human prostate tumor, the [1-$^{13}$C]pyruvate to [1-$^{13}$C]lactate conversion rate constant is 0.045 s$^{-1}$ (Nelson S J, Kurhanewicz J, Vigneron D B, Larson P E Z, Harzstark A L, Ferrone M, Van Criekinge M, Chang J W, Bok R, Park I, Reed G, Carvajal L, Small E J, Munster P, Weinberg V K, Ardenkjaer-Larsen J H, Chen A P, Hurd R E, Odegardstuen L-I, Robb F J, Tropp J, Murray J A. Metabolic imaging of patients with prostate cancer using hyperpolarized [1-13C]pyruvate. Sci. Trans. Med. 2013; 5). With rigorous modeling, this can yield the lactate dehydrogenase flux (Brindle K. Watching tumors gasp and die with MRI: The promise of hyperpolarized 13C MR spectroscopic imaging. Brit. J. Radiol. 2012; 85: 697 708). Particularly the $^{31}$PMRSI modality offers the unique opportunity to measure steady-state unidirectional fluxes completely non-invasively. This takes advantage of the magnetization transfer [MT] phenomenon. An RF pulse is used to selectively perturb only certain molecular nuclear magnetization from equilibrium. Monitoring the (relatively slow) magnetization recovery with spatial encoding allows mapping of faster metabolic fluxes, again with proper modeling (Zhu X-H, Qiao H, Du F, Xiong Q, Liu X, Zhang X, Ugurbil K, Chen W. Quantitative imaging of energy expenditure in human brain. Neuroimage. 2012; 60: 2107-2117; From AHL, Ugurbil K. Standard magnetic resonance-based measurements of the Pi ? ATP rate do not index the rate of oxidative phosphorylation in cardiac and skeletal muscles. Am. J. Physiol. Cell Physiol. 2011; 301: C1-C11; Balaban R S, Koretsky A P. Interpretation of 31P NMR saturation transfer experiments: What you can't see might confuse you. Am. J. Physiol. Cell Physiol. 2011; 301: C12-C15). For example in the brain, the integrated cellular creatine kinase flux and ATP production/consumption rates have been determined.

Spatial Resolution.

Extant metabolic imaging has revealed a tremendous amount about normal and pathological biochemistry, as it actually obtains in vivo. However, new approaches can be attractive. The PET and HP-$^{13}$CMRSI modalities are costly. Typical nominal spatial resolutions and voxel volumes for human modalities are: $^{31}$PMRSI[(1.3 cm)$^3$=2.2 mL] (17); $^1$HMRSI [(1 cm)$^3$=1 mL] (20), SPECT [(1 cm)$^3$=1 mL] (16) HP-$^{13}$CMRSI [(7 mm)$^3$=340 μL] (15); PET [(5 mm)$^3$=125 μL] (16); and $^{23}$NaMRSI [(4 mm)$^3$=64 μL] (see Inglese M, Madelin G, Oesingmann N, Babb J S, Wu W, Stoekel B, Herbert J, Johnson G. Brain tissue sodium concentration in multiple sclerosis: A sodium imaging study at 3 Tesla. Brain 2010; 133: 847-857). These are often insufficient for discriminating significant human anatomy. For example, the cerebral gray matter (GM)/white matter (WM) boundary usually cannot be clearly distinguished. In comparison, MRI generated from the relatively strong $^1$H$_2$O signal—commonly provides higher spatial resolution; (1 mm)$^3$=1 or better. Metabolic images are almost always accompanied by high-resolution MRI [sometimes computed tomography] views of the same tissue. Therefore, though MRI is relatively inexpensive [compared with PET and HP-$^{13}$CMRSI] and employs no ionizing radiation, it is understandably often thought of as providing only anatomical and/or vascular information. Of course, it has long mapped some tissue functions, such as in ciné cardiovascular MRI and functional MRI. The new metaboCESL/CEST techniques approach anatomical $^1$H$_2$O resolution (22), since they employ this strong signal for indirect metabolite detection.

$^1$H$_2$O Mapping of NKA Flux.

Embodiments herein introduce a method for applying a newly-discovered aspect of the biology of water itself active trans-membrane cycling. The [Dynamic-Contrast-Enhanced] DCE-MRI $^1$H$_2$O method is in wide clinical use. It employs any of a number of approved paramagnetic, monomeric Gd(III) chelates as contrast agents (CAs). For tissues in which there is extensive CA extravasation, a proper pharmacokinetic analysis of the CA bolus DCE-MRI time-course yields the mean lifetime [$\tau_i$] of water molecules inside the cells within a voxel (Li X, Priest R A, Woodward W J, Siddiqui F, Beer T M, Garzotto M G, Rooney W D, Springer C S. Cell membrane water exchange effects in prostate DCE-MRI. J. Magn. Reson. 2012; 218: 77-85). The reciprocal [$\tau_i^{-1}$] is the first-order rate constant [$k_{io}$] for the unidirectional, equilibrium cellular water molecule efflux. The inventors herein have documented the evidence, from enzymatic manipulations spanning a number of different cell types and models [from cells to animals to humans], that the $k_{io}$ magnitude is proportional to P-type ATPase turnover (Springer C S, Li X, Tudorica L A, Oh K Y, Roy N, Chui S Y-C, Naik A M, Holtorf M L, A. Afzal A, W. D. Rooney W D, Huang W. Intra-tumor mapping of intra-cellular water lifetime: Metabolic images of breast cancer? NMR Biomed. 2014; 27: 760-773). This is likely due to active transmembrane water cycling that accompanies the osmolyte cycling driven by the membrane ion pump.

Because the normal blood-brain-barrier is CA-impermeable, cerebral DCE-MRI data do not directly yield $\tau_i$. However, the mean capillary water lifetime [$\tau_b$] is readily determined. Fortunately, the metabolic activity of cerebral neurons is exquisitely, symbiotically connected with those of neuroglia [oligodendrocytes, astrocytes] and thence capillary endothelial cells all within synaptic proximities (see Lee Y, Morrison B M, Li Y, Lengacher S, Farah M H, Hoffman P N, Liu Y, Tsingalia A, Jin L, P W. Zhang P-W, Pellerin L, Magistretti P J, Rothstein J D. Oligodendroglia metabolically support axons and contribute to neurodegeneration. Nature 2012; 487: 443-448; Rinholm J E, Bergersen L H. The wrap that feeds neurons. Nature 2012; 487: 435-436; Abbot N J, Rönnbäck L, Hansson E. Astrocyte-endothelial interactions at the blood-brain barrier. Nat. Rev. Neurosci. 2006; 7: 41 53; and Harris J J, Jolivet R, Attwell D. Synaptic energy use and supply. Neuron 2012; 75: 762-777). The terms "neurovascular unit" and "gliovascular unit" have been coined to connote this. In the examples described herein, results from normal and Multiple Sclerosis normal-appearing [MS-NA] brain are presented, along with MS lesion and glioma tumor, indicating that $\tau_b^{-1}$ [$k_{po}$] is proportional to metabolic turnover within the neurogliovascular unit. The examples described herein show the first human brain $k_{po}$ maps [40 μL voxels], and present evidence of unexpected results including that these are metabolic flux maps at $^1$H$_2$O resolution.

"Quantitative MRI" produces parametric maps of MR, pathophysiological, and/or pharmacokinetic biomarker properties. The DCE-MRI subcategory is particularly significant because it applies to a wide pathology range. In DCE-MRI, the $T_1$-weighted tissue $^1H_2O$ MRI signal intensity is acquired before, during, and after the (usually) bolus injection of a hydrophilic, paramagnetic contrast agent. As used herein, the term contrast agent (CA) is synonymous with contrast reagent (CR). The CA passage through a tissue region-of-interest (ROI) can cause a transient increase of the longitudinal $^1H_2O$ relaxation rate constant $[R_1 \equiv (T_1)^{-1}]$ with consequent elevated MR steady-state signal intensity. This elevation may be identified on the MR image.

In DCE-MRI, the neglect of intercompartmental water exchange kinetics considerations can lead to systematic errors in parameters extracted by quantitative analyses. Examples here are the compartmental water mole fractions defining tissue spaces. Therefore, DCE-MRI is also a subcategory of in vivo MR "molecular imaging," mapping the distribution and/or activity of molecules in living tissues.

In essence, in embodiments, the CA plays the role of the nuclear medicine radioactive tracer. However, in nuclear medicine, the tracer is detected directly (by its radioactivity in disintegrations per second (dps), the amount of tracer present in the tissue, but compartmental localization is not intrinsic to the signal). In contrast, the MRI CA is detected indirectly, via its interaction with water and effect on the nature of tissue $^1H_2O$ relaxation (so the water interaction with the CA is what is directly traced). Beneficially, the CA is not radioactive. Also, MRI involves no ionizing radiation.

Metabolic imaging with high spatial resolution is very desirable. Approved doses of monomeric Gd(III) chelate contrast agents (CAs) yield DCE-MRI data from the normal and normal-appearing human brain. There is no significant cerebral CA extravasation. Shutter-speed pharmacokinetic analysis of the DCE time-course yields the mean water molecule capillary lifetime $(\tau_b)$ in the high-resolution $^1H_2O$ MRI voxel $[(1 \text{ mm})^3$; or region-of-interest (ROI)], along with the blood volume fraction $(v_b)$. The reciprocal $(\tau_b^{-1})$ is the first-order rate constant $(k_{po})$ for unidirectional microvessel water efflux at equilibrium. Population-averaged ROI $\tau_b$ values are 345 ms and 403 ms in normal white matter (WM) and (GM), respectively. The $v_b$ of WM is less than half that of GM. In normal-appearing multiple sclerosis (MS) brain, $\tau_b$ values are increased by ~40% and ~25% in WM and GM, respectively: they are even larger in MS lesions and in glioblastoma multiforme tumors. Analyses of variations in the independent $\tau_b$ and $v_b$ parameters indicate that the $\tau_b$ increase is dominated by a decrease in the microvascular water permeability coefficient, $P_W$. Concomitant decreases in adenosine triphosphate and creatine phosphate levels [from $^{31}P$ MR spectroscopic imaging (MRSI)], along with literature reports of increased tissue sodium concentration [from $^{23}NaMRSI$] in MS further indicate that $P_W$ is dominated by an active component. These results are consistent with a decrease in gliovascular unit $Na^+/K^+ATPase$ [NKA] activity in these pathologies. Alterations in NKA activity can be transmitted to the $\tau_b$ quantity by a cascade of changes in known active trans-membrane water cycling processes within the gliovascular unit. This offers the promise that high-resolution cerebral $\tau_b$ maps serve as reciprocal NKA activity maps.

Metabolic imaging can be defined as mapping the distributions of metabolic molecule tissue concentrations ("levels") and/or metabolic fluxes: the metabolic thermodynamic and kinetic aspects, respectively. Metabolic imaging has the potential for early disease detection and therapy monitoring on an individualized basis. Restricting ourselves essentially to human subjects, metabolic imaging is mostly accomplished by positron emission tomography [PET] and magnetic resonance spectroscopic imaging [MRSI], with some effort also by single photon emission computed tomography [SPECT] [M M Khalil, J L Tremoleda, T B Bayomy, W Gsell, "Molecular SPECT Imaging: An Overview," *Int J Mol Imag* (2011)]. Exemplifying metabolic thermodynamics, $^{31}PMRSI$ gives the distribution of high-energy phosphate [HEP] levels in the brain [X-H Zhu, H Qiao, F Du, Q Xiong, X Liu, X Zhang, K Ugurbil, W Chen, "Quantitative Imaging of Energy Expenditure in Human Brain," *Neuroimage* 60: 2107-2117 (2012)]. Such data could be used, for example, to estimate the cerebral distribution of the free energy for adenosine triphosphate [ATP] hydrolysis. Another method, $^{23}NaMRSI$, maps tissue sodium concentration [TSC] [M. Inglese, G. Madelin, N. Oesingmann, J. S. Babb, W. Wu, B. Stoekel, J. Herbert, G. Johnson, "Brain Tissue Sodium Concentration in Multiple Sclerosis: A Sodium Imaging Study at 3 Tesla," *Brain* 133, 847-857 (2010)]. Generally, a TSC increase reflects an increase in intracellular sodium, $Na_i^+$ [The Hillal Effect], which in turn means a decrease in the transcytolemmal sodium electrochemical potential gradient. Other thermodynamic aspects assessed by metabolic imaging include distributions of $H_3O^+$ (pH), $O_2$ (diminished in hypoxia), and redox levels. Though they aren't metabolites, PET and SPECT can be used to map approximate biochemical receptor tissue concentrations. For example, the $[^{11}C]$cocaine tracer was used to show the dopamine transporter concentration is 700 nM in the cocaine abuser striatum [J Logan, N D Volkow, J S Fowler, G-J Wang, M W Fischman, R W Foltin, N N Abumrad, S Vitkun, S J Gatley, N Pappas, R Hitzemann, C E Shea, "Concentration and Occupancy of Dopamine Transporters in Cocaine Abusers with $^{11}$C]Cocaine and PET," *Synapse* 27:347-356 (1997)]. These receptors very often catalyze, or trigger by signaling, metabolic reactions.

In order to determine metabolic fluxes with PET and hyperpolarized $^{13}CMRSI$ [HP-$^{13}CMRSI$], a non-equilibrium isotope distribution [positron emitting isotope for PET; hyperpolarized (stable) $^{13}C$ isotope magnetization for HP-$^{13}CMRSI$] is introduced exogenously, with minimal invasion. Then, the (relatively slow) regional approach to isotope equilibrium is mapped using spatially encoded detection. The evaluation of much faster steady-state ("equilibrium") unidirectional fluxes (rates) must be accomplished with proper modeling. For example in the prostate tumor, the $[1-^{13}C]$pyruvate to $[1-^{13}C]$lactate conversion rate constant is 0.045 s$^{-1}$ [S J Nelson, J Kurhanewicz, D B Vigneron, P E Z Larson, A L Harzstark, M Ferrone, M Van Criekinge, J W Chang, R Bok, I Park, G Reed, L Carvajal, E J Small, P Munster, V K Weinberg, 1H Ardenkjaer-Larsen, A P Chen, R E Hurd, L-I Odegardstuen, F J Robb, J Tropp, J A Murray, "Metabolic Imaging of Patients with Prostate Cancer Using Hyperpolarized [1-13C]Pyruvate," *Sci Trans Med* 5:198ra108 (2013)]. With further modeling, this can yield the lactate dehydrogenase flux. Particularly the $^{31}PMRSI$ modality offers the unique opportunity to measure steady-state unidirectional fluxes completely non-invasively. This takes advantage of the magnetization transfer [MT] phenomenon. A radio frequency [RF] pulse is used to selectively perturb only certain molecular nuclear magnetization from equilibrium. Monitoring the (relatively slow) nuclear magnetization recovery with spatial encoding allows mapping of faster metabolic fluxes, again with proper modeling. For example in the brain, the integrated cellular creatine kinase flux and ATP production/consumption rates can be determined [X-H Zhu, H Qiao, F Du, Q Xiong, X Liu, X Zhang, K Ugurbil, W Chen, "Quantitative Imaging of Energy Expenditure in Human Brain," *Neuroimage* 60: 2107-2117 (2012)].

Thus, metabolic imaging provides a tremendous amount of information about normal and pathological biochemistry, as it actually obtains in vivo. However, improvements can always be sought. The PET and HP-$^{13}$CMRSI modalities are costly. Typical nominal spatial resolutions and voxel volumes for the human metabolic imaging modalities are: $^{31}$PMRSI [$(1.3\ cm)^3$=2.2 mL] [X-H Zhu, H Qiao, F Du, Q Xiong, X Liu, X Zhang, K Ugurbil, W Chen, "Quantitative Imaging of Energy Expenditure in Human Brain," *Neuroimage* 60: 2107-2117 (2012)]; SPECT [$(1\ cm)^3$=1 mL] [M M Khalil, J L Tremoleda, T B Bayomy, W Gsell, "Molecular SPECT Imaging: An Overview," *Int l Mol Imag* (2011.], HP-$^{13}$CMRSI [$(7\ mm)^3$=340 µL] [S J Nelson, J Kurhanewicz, D B Vigneron, P E Z Larson, A L Harzstark, M Ferrone, M Van Criekinge, J W Chang, R Bok, I Park, G Reed, L Carvajal, E J Small, P Munster, V K Weinberg, J H Ardenkjaer-Larsen, A P Chen, R E Hurd, L-I Odegardstuen, F J Robb, J Tropp, J A Murray, "Metabolic Imaging of Patients with Prostate Cancer Using Hyperpolarized [1-13C] Pyruvate," *Sci Trans Med* 5:198ra108 (2013)]; PET [$(5\ mm)^3$=125 µL] [M M Khalil, J L Tremoleda, T B Bayomy, W Gsell, "Molecular SPECT Imaging: An Overview," *Int J Mol Imag* (2011)]; and $^{23}$NaMRSI [$(4\ mm)^3$=64 µL] [M. Inglese, G. Madelin, N. Oesingmann, J. S. Babb, W. Wu, B. Stoekel, J. Herbert, G. Johnson, "Brain Tissue Sodium Concentration in Multiple Sclerosis: A Sodium Imaging Study at 3 Tesla," *Brain* 133, 847-857 (2010)]. These are often insufficient for discriminating significant human anatomy. For example, the cerebral gray matter (GM)/white matter (WM) boundary usually cannot be distinguished. In comparison, MRI—generated from the relatively strong $^1H_2O$ signal routinely offers substantially higher spatial resolution; $(1\ mm)^3$=1 µL, or better. In fact, modern metabolic images are almost always accompanied by high-resolution MRI and sometimes computed tomography (CT)] views of the same tissue. Understandably therefore, MRI is often thought of as providing only anatomical information—with the exceptions of tissue function in some cases such as functional MRI and cine cardiovascular MR. Compared with PET and HP-$^{13}$CMRSI, MRI is relatively inexpensive. Also, MRI employs no ionizing radiation.

Embodiments herein provide an opportunity to detect and map on-going gliovascular unit metabolic activity using high-resolution $^1H_2O$ MRI. This is achieved with only repeated, non-selective RF $^1H_2O$ magnetization perturbation before, during, and after the minimally invasive IV injection of approved doses of any of several very common clinical contrast agents (CAs).

Mean Brain Intra-Capillary Blood Water Molecule Lifetime [$\tau_b$].

The average erythrocyte speed through cerebral cortical capillaries is 2 mm/s (see Itoh Y, Suzuki N. Control of brain capillary blood flow. J. Cereb. Blood Flow & Metabol. 2012; 32: 1167-1176; Gesztelyi G, Finnegan W, DeMaro J A, Wang J-Y, Chen J-L, Fenstermacher J. Parenchymal microvascular systems and cerebral atrophy in spontaneously hypertensive rats. Brain Res. 1993; 611: 249-257; and Pawlik G, Rackl A, Bing R J. Quantitative capillary topography and blood flow in the cerebral cortex of cats: An in vivo microscopic study. Brain Res. 1981; 208: 35-58). The average erythrocyte speed through cerebral cortical capillaries measures blood velocity. In a common $(1\ mm)^3$ high-resolution human $^1H_2O$ MRI voxel, a conservatively small estimate of the average, tortuous capillary path-length is 2 mm (Pawlik G, Rackl A, Bing R J. Quantitative capillary topography and blood flow in the cerebral cortex of cats: An in vivo microscopic study. Brain Res. 1981; 208: 35-58; Hutchinson E B, Stefanovic B, Koretsky A P, Silva A C. Spatial flow-volume dissociation of the cerebral microcirculatory response to mild hypercapnia. Neuroimage 2006; 32: 520-530). Thus, the mean voxel transit time for a blood water molecule is at least 1 s. Many things happen to the molecule during this period. The mean lifetime inside an erythrocyte ($\tau_i$) is 10 ms (Wilson G J, Woods M, Springer C S, Bastawrous S, Bhargava P, Maki J H. Human whole blood 1H2O longitudinal relaxation with normal and high-relaxivity contrast reagents: Influence of trans-cell-membrane water exchange. Magn. Reson. Med. 2014; 71: 000-000; Li X, Huang W, Morris E A, Tudorica L A, Seshan V E, Rooney W D, Tagge I, Wang Y, Xu J, and Springer C S. Dynamic NMR effects in breast cancer dynamic-contrast-enhanced MRI. Proc. Natl. Acad. Sci., USA 2008; 105: 17937 17942; Hills B P, Belton P S. NMR studies of membrane transport. Ann. Rep. NMR Spectros. 1989; 21: 99 159; Herbst M D, Goldstein J H. A review of water diffusion measurement by NMR in human red blood cells. Am. J. Physiol. 1989; 256 (Cell Physiol. 25): C1097-C1104). By equilibrium mass action, for a 40% hematocrit the mean plasma lifetime before entering a red cell ($\tau_p$) is 15 ms. Thus, any given water molecule enters and leaves erythrocytes ~40 times during its voxel passage [also, the entire red cell water content is exchanged ~100 times]. The 3D Einstein diffusion equation, $<r^2>=6\ Dt_D$ (Marshall A G. Biophysical Chemistry: Principles, Techniques, and Applications, John Wiley & Sons, New York, 1978, p. 152), allows estimation of $H_2O$ molecule/capillary wall encounter frequency: r is the capillary radius, D the water diffusion coefficient, and $t_D$ the average time to diffuse a distance r. Inserting the mean feline r value, 2.6 µm, and a conservatively small D value [1.5 µm$^2$/ms (half the pure water D)], we obtain $t_D$=0.8 ms. Even an $H_2O$ molecule in the center of the capillary lumen would encounter the wall >1000 times during its voxel passage. It is a very good approximation that capillary blood water is "well-mixed." Thus, the probability of a water molecule escaping the capillary can be estimated. The $\tau_b$ inverse, $\tau_b^{-1}$, is the unidirectional first-order rate constant, $k_{po}$, for water extravasation. For a well-mixed lumen, this is: $\tau_b^{-1}=P_W^\dagger (A_{ca}/V_{ca})$, where $P_W^\dagger$ is the transendothelial water permeability coefficient, $A_{ca}$ the individual capillary surface area, and $V_{ca}$ the individual capillary lumen volume (Chen S-T, Springer C S. Ionophore-catalyzed cation transport between phospholipid inverted micelles manifest in DNMR. Biophys. Chem. 1981; 14: 375-388). For a cylindrical microvessel: $\tau_b^{-1}=2(P_W^\dagger/r)$. The inventors herein noted that, a r=2.6 µm and a primate $P_W^\dagger$ value of 2 µm/s, predicts 650 ms for $\tau_b$ (see Labadie C, Lee J-H, Vétek G, Springer C S. Relaxographic imaging. J. Magn. Reson. B 1994; 105: 99-112; Eichling J O, Raichle M E, Grubb R L, Ter-Pogossian M M. Evidence of the limitations of water as a freely diffusible tracer in brain of the rhesus monkey. Circ. Res. 1974; 35: 358-364; and Paulson O B, Hertz M M, Bolwig T G, Lassen N A. Filtration and diffusion of water across the blood-brain barrier in man. Microvasc. Res. 1977; 13: 113-124). The $k_{po}$ ($\tau_b^{-1}$) value (1.5 s$^{-1}$) corresponds to ~78% probability [=100(1−exp(−$k_{po}$t): t is the capillary transit time (~1 s)] any given water molecule will exchange out of the blood space [to be replaced by an extravascular $H_2O$ molecule] during its capillary passage). Because blood velocity causes no net change in the number of capillary $H_2O$ molecules (which are indistinguishable), the $\tau_b$ quantity is not influenced by the blood flow [F; CBF] magnitude. This contrasts with the situation for the extraction of labeled water, which is nearly "perfusion-limited" (Eichling J O, Raichle M E, Grubb R L, Ter-Pogossian M M. Evidence of the limitations of water as a freely diffusible tracer in brain of the rhesus monkey. Circ. Res. 1974; 35: 358-364).

It is important to note that $P_W^\dagger/r$ is also independent of the intensive capillary density [$\rho^\dagger$] property. With tracer studies [e.g., intracarotid $^{15}OH_2$] and sacrificial autoradiography [e.g., IV $^3HOH$], one obtains the intensive $P_W^\dagger S$ product, where S is the total ROI vascular surface area per unit tissue volume—dependent on the vascularity (see Eichling J O, Raichle M E, Grubb R L, Ter-Pogossian M M. Evidence of the limitations of water as a freely diffusible tracer in brain of the rhesus monkey. Circ. Res. 1974; 35: 358-364; Reid A C, Teasdale G M, McCulloch J. The effects of dexamethasone administration and withdrawal on water permeability across the blood-brain barrier. Ann. Neurol. 1983; 13, 28-31). The latter is measured by the blood volume fraction [$v_b$ (CBV)]: the $\rho^\dagger \bullet V$ product [V is the mean $V_{ca}$]. In $P_W^\dagger/r$, r is the mean ROI vascular radius, and is related to only the V factor of the $\rho^\dagger \bullet V$ product. Thus, theory demands that $\tau_b$ is independent of $\rho^\dagger$, and therefore a potentially powerful new type of imaging biomarker: we characterize it as supra-intensive. Examples described herein show that $k_{po}$ is also experimentally independent of $v_b$, a very meaningful finding, and that it can distinguish cerebral pathology undetectable with ordinary intensive biomarkers.

Inter-Compartmental $^1H_2O$ Exchange Effects in In Vivo MR.

It has been known that a sufficiently concentrated paramagnetic solute localized in a cell suspension extracellular space can cause non-mono-exponential longitudinal and/or transverse $^1H_2O$ relaxation. A two-site exchange [2SX] analysis of the recovery yields the mean intracellular water molecule lifetime [see Springer C S, Li X, Tudorica L A, Oh K Y, Roy N, Chui S Y-C, Naik A M, Holtorf M L, A. Afzal A, W. D. Rooney W D, Huang W. Intra-tumor mapping of intra-cellular water lifetime: Metabolic images of breast cancer? NMR Biomed. 2014; 27: 760-773; Li X, Huang W, Morris E A, Tudorica L A, Seshan V E, Rooney W D, Tagge I, Wang Y, Xu J, and Springer C S. Dynamic NMR effects in breast cancer dynamic-contrast-enhanced MRI. Proc. Natl. Acad. Sci., USA 2008; 105: 17937 17942; Hills B P, Belton P S. NMR studies of membrane transport. Ann. Rep. NMR Spectros. 1989; 21: 99 159; and Herbst M D, Goldstein J H. A review of water diffusion measurement by NMR in human red blood cells. Am. J. Physiol. 1989; 256 (Cell Physiol. 25): C1097-C1104). This is equilibrium transcytolemmal water exchange. Longitudinal relaxation for yeast cell samples exemplifies this (see Zhang Y, Poirier-Quinot M, Springer C S, Balschi J A. Active trans-plasma membrane water cycling in yeast is revealed by NMR. Biophys. J. 2011; 101: 2833-2842; Labadie C, Lee J-H, Vetek G, Springer C S. Relaxographic imaging. J. Magn. Reson. B 1994; 105: 99-112; and Silva M D, Helmer K G, Lee J-H, Han S S, Springer C S, Sotak C H. Deconvolution of compartmental water diffusion coefficients in yeast-cell suspensions using combined T1 and diffusion measurements. J. Magn. Reson. 2002; 156: 52-63). The extracellular CA increases the intrinsic outside water proton signal [$^1H_2O_o$] longitudinal relaxation rate constant, $R_{1o}$ [$\equiv(T_{1o})^{-1}$]. Such an approach increases the longitudinal transcytolemmal "shutter-speed," $\tau_{1c}^{-1}$ [$\equiv|R_{1o}-R_{1i}|$], sufficiently that this water exchange NMR system is moved out of its fast-exchange-limit [FXL] condition [$\tau_{1c}^{-1} \ll (\tau_i^{-1}+\tau_o^{-1})$; $R_{1i}$ is the intrinsic inside ($^1H_2O_i$) relaxation rate constant]. A sufficient outside CA concentration, [$CA_o$], allows the NMR system to reach the slow-exchange-regime [SXR] condition. This is characterized by non-mono-exponential magnetization recovery, but is distinct from the slow-exchange- and no-exchange-limit conditions. It is customary to achieve the SXR condition with cell suspensions, but there is no convincing evidence that the SXR can be reached in vivo with approved CAs. However, it was shown that when the [$CA_o$] value is only modest, and the system can attain only the fast-exchange-regime [FXR] condition, it is still possible to measure $\tau_i$ by varying $\tau_{1c}^{-1}$ (by varying [$CA_o$]) (Labadie C, Lee J-H, Vetek G, Springer C S. Relaxographic imaging. J. Magn. Reson. B 1994; 105: 99-112). The FXR condition features mono-exponential longitudinal recovery: i.e., $R_1$ is single-valued, but with a non-linear [$CA_o$]-dependence. In the FXL condition, this dependence is linear. The in vivo implementation of these principles generally employs some variant of DCE-MRI, the serial acquisition of $T_1$-weighted images before, during, and after a bolus CA injection. The common tracer paradigm [TP] pharmacokinetic analysis of an ROI or pixel signal intensity time-course imposes the assumption that all exchange systems remain in their FXL conditions. This denies access to $\tau_b$, or [each is held effectively zero in the FXL], and causes systematic changes in other pharmacokinetic parameters, such as $v_b$. However, Shutter-Speed Paradigm [SSP] pharmacokinetic analysis allows that $\tau_b$ and are finite, and relieves the systematic distortions of other biomarkers. Overviews of these concepts are described in Li X, Priest R A, Woodward W J, Siddiqui F, Beer T M, Garzotto M G, Rooney W D, Springer C S. Cell membrane water exchange effects in prostate DCE-MRI. J. Magn. Reson. 2012; 218: 77-85; Zhang Y, Poirier-Quinot M, Springer C S, Balschi J A. Active trans-plasma membrane water cycling in yeast is revealed by NMR. Biophys. J. 2011; 101: 2833-2842; Li X, Huang W, Morris E A, Tudorica L A, Seshan V E, Rooney W D, Tagge I, Wang Y, Xu J, and Springer C S. Dynamic NMR effects in breast cancer dynamic-contrast-enhanced MRI. Proc. Natl. Acad. Sci., USA 2008; 105: 17937 17942; and Li X, Rooney W D, Springer CS. A unified MRI pharmacokinetic theory for intravascular and extracellular contrast reagents. Magn. Reson. Med. 2005; 54: 1351-1359.

Multiple infusions of an intravascular CA were used to vary the murine brain transendothelial shutter-speed, $\tau_{1e}^{-1}$ [$\equiv|R_{1b}-R_{1exv}|$]($^1H_2O_b$ and $^1H_2O_{exv}$ are the intra- and extravascular signals, respectively) and reach the FXR condition [$\tau_{1e}^{-1} \to (\tau_b^{-1}+\tau_{exv}^{-1})$; $\tau_{exv}$ is the mean extravascular water molecule lifetime] for this water exchange system. Variation of the plasma CA concentration ([$CA_p$]) allowed the exchange kinetics to be measured (see Schwarzbauer C, Morrissey S P, Deichmann R, Hillenbrand C, Syha J, Adolf H, Nöth U, Haase A. Quantitative magnetic resonance imaging of capillary water permeability and regional blood volume with an intravascular MR contrast agent. Magn. Reson. Med. 1997; 37: 769 777). The cortical $\tau_b$ value calculated from these results was 295 ms—of the magnitude earlier predicted from literature parameters. An approach using a single intravascular CA injection was demonstrated in the rat (see Barbier E L, St. Lawrence Kans., Grillon E, Koretsky A P, Décorps M. A model of blood-brain barrier permeability to water: Accounting for blood inflow and longitudinal relaxation effects. Magn. Reson. Med. 2002; 47: 1100-1109). The [$CA_p$] value was not varied, but the acquisition was combined with an Arterial Spin Labeling [ASL] variant. This approach yields only $P_W^\dagger S$ and, because ASL is used, the F value must be included in order to obtain $P_W^\dagger S$ correctly. An SSP DCE-MRI method was introduced whereby a single CA bolus injection can be used to determine human brain $\tau_b$ (Rooney W D, Yankeelov T E, Coyle P K, Telang F W, Springer C S. Regional blood volumes and intravascular water lifetimes in human brain. Proceedings of the 11th Annual Meeting ISMRM, Toronto, Ontario, Canada, 2003; 2188). In some embodiments, this approach may be used. The water exchange index [WEI], an approximate, dimensionless, non-linear $\tau_b^{-1}$ estimate was demonstrated in the mouse, an approach also requiring a single intravascular CA injection (see Kim Y R, Tejima E, Huang S, Atochin D N, Dai G, Lo E H, Huang P L, Bogdanov A, Rosen B R. In vivo quantification of transvascular water exchange during the acute phase of a permanent stroke. Magn. Reson. Med. 2008; 60: 813-821). Unfortunately, the WEI approximation formally depends on the $v_b$ value (Huang S, Farrar C T, Dai G, Kwon S J, Bogdanov A A, Rosen B R, Kim Y R. Dynamic monitoring of blood-brain barrier integrity using water exchange index (WEI) during mannitol and CO2 challenges in mouse brain. NMR Biomed. 2013; 26: 376-385). As noted above, an important feature of the actual $\tau_b^{-1}$ [$k_{po}$] biomarker is its $v_b$-independence if r does not vary.

Indirect Detection.

There are crucial differences between the tracer and shutter-speed paradigms. Classic tracers [radiolabeled molecules, electron-dense compounds, etc.] are detected directly: the tracer molecule is also the signal molecule. Though the CA of DCE-MRI plays the tracer pharmacokinetic role, it is detected indirectly—via its effect on the $^1H_2O$ signal. Thus, the CA is the tracer molecule but water is the signal molecule. These species are never distributed equally in tissue: water is in every compartment, each of which contributes to the $^1H_2O$ signal. For the classic solute tracer paradigm, water is not molecular: it is assumed to be a continuum filling tissue spaces. Furthermore, the compartmentalization of the classic tracer is not intrinsic to its signal: one cannot tell if the molecule is intra- or extravascular. However, CA compartmentalization is inherently encoded in the DCE-MRI time-course. Three simultaneous signals [$1^1H_2O_b$, $1^1H_2O_o$, and $^1H_2I_i$] and their sequentially varying $T_1$ values report the time-varying [CA] values in each compartment CA enters (Li X, Priest R A, Woodward W J, Siddiqui F, Beer T M, Garzotto M G, Rooney W D, Springer C S. Cell membrane water exchange effects in prostate DCE-MRI. J. Magn. Reson. 2012; 218: 77-85; Li X, Rooney W D, Springer C S. A unified MRI pharmacokinetic theory for intravascular and extracellular contrast reagents. Magn. Reson. Med. 2005; 54: 1351-1359). Thus, the imposition of a tracer analysis on DCE-MRI data joins contradictory postulates: unknown vs. known CA compartmentalization. The only reconciliation is by the assumption that all water exchange systems are in FXL conditions. If m is assumed effectively zero, the vascular CA compartmentalization is "short-circuited;" as if CA is both intra- and extravascular a tracer-like ambiguity. These principles apply also to metaboCESL/CEST (Strijkers G J, Hak S, Kok M B, Springer C S, Nicolay K. Three-compartment T1 relaxation model for intracellular paramagnetic contrast agents. Magn. Reson. Med. 2009; 61, 1049-1058).

Chemical Equilibrium Measurement.

Another important difference is experimental. For classic water tracers [e.g., $^{15}OH_2$], studies may be initiated with a non-equilibrium isotope compartmental distribution, and the kinetics of the tissue approach to equilibrium may be monitored by detecting only the labeled water (e.g., see Eichling J O, Raichle M E, Grubb R L, Ter-Pogossian M M. Evidence of the limitations of water as a freely diffusible tracer in brain of the rhesus monkey. Circ. Res. 1974; 35: 358-364). In DCE-MRI, there is no compartmental selection in the initial water proton magnetization perturbation: all $^1H_2O$ signals are (usually) inverted, and the return to magnetic equilibrium of each of them is monitored simultaneously. Only magnetization equilibrium is perturbed. These methods can lead to common parameters [e.g., $P_W^\dagger$ here], and thus can support each other. However, the experimental results must be analyzed with different paradigms as appropriate. For example, though the SSP assumes that brain capillary water is "well-mixed" it does not require the same assumption of extravascular water, which is in fact not well-mixed. Although $\tau_i$ and $\tau_o$ values are typically hundreds of milliseconds, that of $\tau_{exv}$ is typically tens of seconds—because of the relatively sparse microvessel density. Yet the extravascular ["parenchymal"] MR system is in the Fast-Exchange-Limit condition even though transcytolemmal water exchange is not particularly fast. With no extravascular CA, the $\tau_{1c}^{-1}$ values are much smaller than $(\tau_i^{-1}+\tau_o^{-1})$. Thus, the non-well-mixed nature of the parenchyma is of no consequence to the DCE-MRI experiment, but "unstirred layer" effects can be significant for $^{15}OH_2$ re-intravasation kinetics, or for any tracer study (Eisner D A, Smith T W. The Na—K pump and its effectors in cardiac muscle. In The Heart and Cardiovascular System (2nd Ed.), H. A. Fozzard, E. Haber, R. B. Jennings, and A. M. Katz, Eds. Raven Press, New York, 1992, Chap. 35, pp. 863-902).

Active Trans-Membrane Water Cycling.

There is considerable interest in the brain capillary $\tau_b$ ($k_{po}^{-1}$) quantity. As indicated above, $\tau_b$ variation can reflect change in capillary r, in $P_W^\dagger$, or in both. Vasodilation or vasoconstriction [r alteration] would respectively decrease or increase $k_{po}$ [$\tau_b^{-1}$]. However, the rate constant for r changes is orders of magnitude smaller than $k_{po}$ itself (Zhang Y, Poirier-Quinot M, Springer C S, Balschi J A. Active trans-plasma membrane water cycling in yeast is revealed by NMR. Biophys. J. 2011; 101: 2833-2842; Ye R, Verkman A S. Simultaneous optical measurement of osmotic and diffusional water permeability in cells and liposomes. Biochem. 1989; 28: 824-829). Changes in $k_{po}$ not attributable to capillary size alteration are ascribed to $P_W^\dagger$ variation and, until recently, this has been conceived as resulting from alterations in passive molecular processes [$P_W^\dagger$(passive)]. These include: a) para-cellular water passage through endothelial tight junctions, b) simple, trans-cellular water diffusion across cell membrane lipid bilayers, and c) trans-cellular transport through membrane aquaporin protein water channels and/or trans-cellular leakage through membrane transporters (Kimelberg H K. Water homeostasis in the brain: Basic concepts. Neurosci. 2004; 129: 851-860; Amiry-Moghaddam M, Ottersen O P. The molecular basis of water transport in the brain. Nat. Rev. Neurosci. 2003; 4: 991 1001; Li J, Shaikh S A, Enkavi G, Wen P-C, Huang Z, Tajkhorshid E. Transient formation of water conducting states in membrane transporters. Proc. Nat. Acad. Sci. 2013; 110: 7696-7701). However, NMR studies have recently revealed the cell membrane water permeability coefficient ($P_W$) to have an active component [$P_W$(active)] that dominates over the passive component (Springer C S, Li X, Tudorica L A, Oh K Y, Roy N, Chui S Y-C, Naik A M, Holtorf M L, A. Afzal A, W. D. Rooney W D, Huang W. Intra-tumor mapping of intra-cellular water lifetime: Metabolic images of breast cancer? NMR Biomed. 2014; 27: 760-773; Zhang Y, Poirier-Quinot M, Springer C S, Balschi J A. Active trans-plasma membrane water cycling in yeast is revealed by NMR. Biophys. J. 2011; 101: 2833-2842). This is due to active trans-membrane water cycling accompanying active trans-membrane osmolyte cycling, which is paced by the driving cell membrane P-type ATPase ion pump. For animal cells, this is the $Na^+,K^+$-ATPase, NKA. The molecular mechanism likely involves water co-transporting membrane symporters and supports a cycling flux of $10^{12}$ water molecules/s/cell (see Zeuthen T. Water-transporting proteins. J. Membr. Biol. 2010; 234: 57-73; and Zeuthen T, MacAulay N. Transport of water against its concentration gradient: Fact or fiction? WIREs Membr. Transp. Signal. 2012; 1: 373-381).

As remarked above, $\tau_b$ variation can reflect change in capillary r, in $P_W$, or in both. Alteration of r—vasodilation or vasoconstriction—would respectively increase or decrease $\tau_b$ ($k_{po}^{-1}$). However, the rate constant for r changes is orders of magnitude smaller than $\tau_b^{-1}$ itself [Y Zhang, M Poirier-Quinot, C S Springer, J A Balschi, "Active Trans-Plasma Membrane Water Cycling in Yeast is Revealed by NMR," Biophys. J. 101, 2833-2842 (2011)]. Changes in $\tau_b$ not attributable to capillary size alteration are ascribed to $P_W$ variation and, until now, this has been conceived as resulting from alterations in passive molecular processes [$P_W$(passive)]. Some are indicated in the FIG. 1 cartoon and include: a) paracellular water passage through endothelial tight junctions, b) simple, transcellular water diffusion across cell membrane lipid bilayers, and c) transcellular transport through membrane aquaporin protein water channels and/or transcellular leakage through membrane transporters. In particular, FIG. 1 shows gliovascular unit water exchange mechanisms determining mean water molecule lifetimes in blood ($\tau_b$, beige, labeled 102), interstitium ($\tau_o$, aqua, labeled 104), and endothelial ($\tau_i'$, gray, labeled 106), neuroglial ($\tau_i$, pink, labeled 108), and neuronal ($\tau_i''$, blue, labeled 110) cell spaces. The equilibrium paracellular (a), simple diffusion (b), facilitated transcellular (c), and active water cycling (d, stars) pathways are indicated, as are "Magistretti steps" (e,f,g).

However, Applicants' NMR studies have recently revealed the cell membrane water permeability coefficient ($P_W'$) to have an active component [$P_W'$(active)], and that it dominates the passive component. This is due to active trans-membrane water cycling that accompanies active trans-membrane osmolyte cycling, which is paced by the driving cell membrane transporter ATPase. For mammalian cells, this is the $Na^+/K^+$ATPase (NKA). The molecular mechanism almost certainly involves water co-transporting membrane symporters, and supports a cycling flux of $10^{12}$ water molecules/cell/s. In the FIG. 1 cartoon, these active processes are indicated by d) trans-membrane water cycles (stars) in endothelial (gray), neuroglial (pink) and neuronal (purple) cells in intimate proximity within synaptic dimensions. The pink cells can be astrocytes, oligodendrocytes, pericytes, etc. Combinations of neurons, glia, and microvessels have been termed "gliovascular units", because of their crucial, exquisite symbiotic metabolic and energetic interactions. The e-g) "Magistretti Mechanism" shown in FIG. 1 has astrocytes and oligodendrocytes essentially conducting most glycolysis and transferring lactate to neurons for mostly oxidative phosphorylation: the capillary is intimately involved. Because it maintains the trans-membrane ion gradients that drive much secondary active transport and produce the membrane potential, one can argue that NKA is the most important enzyme in biology. Therefore, $\tau_b^{-1}$ measurement offers the very exciting possibility of quantifying perhaps the most crucial on-going cellular metabolic activity in the brain. There can be a cascade of this activity [1d), stars] consequent to increased neuronal metabolism. There is no other way to measure NKA activity in vivo.

EXAMPLES

The examples discussed below illustrates systems and methods for determining a level of cellular metabolic activity for a region of interest in order to detect and map on-going gliovascular unit metabolic activity using high-resolution $^1H_2O$ MRI in accordance with various embodiments. The examples discussed below are for illustrative purposes and are not intended to be limiting.

In preliminary results shown below, the inventors herein found that $\tau_b$ is increased 2-fold and 10-fold, respectively, in human multiple sclerosis (MS) lesions and glioblastoma multiforme (GBM) tumors. Since there is good reason to expect that $P_W$(passive) has actually increased, it is highly unlikely the capillary radius could increase sufficiently to overcome this and further cause a $\tau_b$ increase. Thus, the inventors herein hypothesize significant $P_W$(active) decreases occur in these pathological lesions. Perhaps more importantly, as the non-limiting examples discussed below show, $\tau_b$ is also increased even in MS-normal appearing white and gray matter (NAWM and NAGM, respectively).

Methods

Subjects.

Healthy controls [n=6, 2M/4F, 30 (±10) y], and subjects with early relapsing-remitting MS [n=6, 2M/4F 46 (±7) y] were recruited. The MS group was selected to be early in disease but have positive MRI findings. Only subjects between the ages of 18-55 years were studied, in order to avoid potentially confounding physiological differences associated with normal aging. Healthy [2M/4F, 30 (±10) y], relapsing-remitting-MS (RRMS) [2M/4F, 46 (±7) y, 18-55 y], and glioblastoma multiforme (GBM) [3M/2F, 19-57 y] subjects gave informed consent to OHSU Institutional Review Board [IRB] approved protocols. The MS group was early in disease, but with positive MRI findings. An additional 52 year old female late-stage RRMS subject was also studied. The GBM subjects had prior surgical biopsies or resections and chemo-radiation therapy.

$^{31}$PMRSI. MS Subjects.

Healthy control subjects (n=12, age: 24-65 years, 7 females and 5 males) and subjects with multiple sclerosis (n=15, Age: 28-62 years, 10 females, 5 males) were recruited and enrolled in an approved Institutional Review Board protocol. Informed consent was obtained per the study protocol from each subject. MS Subjects went through a self-reported Expanded Disability Status Score (EDSS) assessment test (scores range=2.0-6.5, median=4.0). The tests were scored by a board certified physician.

Healthy and MS Subject DCE-MRI.

A 7 T [Tesla] whole-body MRI instrument (Siemens, Erlangen Germany), with quadrature transmission and 24-channel phased-array receive head RF coils, was used. Dynamic measurements employed a single-slice inversion recovery (IR) turboflash technique (Haase A. Snapshot FLASH MRI. Applications to T1, T2, and chemical-shift imaging. Magn. Reson. Med. 1990; 13: 77-89), sampling magnetization eight post-inversion times [TIs]: the inversion pulse was non-selective. The 128×96 image matrix covered a (256×192) mm² FOV [nominal pixel; (2 mm)²], and a 6° flip angle RF pulse selected a 10 mm transverse slice superior to the lateral ventricles [nominal voxels; (2×2×10) mm³=40 4]. Gadoteridol [ProHance; Bracco Diagnostics, Inc.] was injected into an antecubital vein catheter at 2.5 mL/s using a power injector [Medrad] to deliver a dose of 28 μmol/kg (typically ~5 mL), followed by a 15 mL saline flush at the same rate. For each CA injection, 50 IR image sets were collected with 2.5 s temporal resolution. Total acquisition time was 2.1 minutes. Parametric $R_1$ maps were calculated on a voxel basis by fitting the signal magnitude at each TI with a full Bloch simulation incorporating all RF pulses and delays. The IR was modeled with a two-parameter single exponential, using a gradient expansion algorithm.

GBM Subject DCE-MRI.

Data were acquired using a 3 T Tim Trio (Siemens) instrument, body transmit and 12-channel phased-array head receive RF coils, and a full volume 2D GRE-EPI sequence. Non-selective IR pulses sampled at 24 TIs. The $[128]^2$ image matrix covered a $(256)^2$ FOV [nominal $(2 \text{ mm})^3$ isotropic resolution [8 µl nominal voxels] (Grinstead J W, Rooney W D. Fast T1 mapping in human brain using inversion recovery EPI with GRAPPA at 3 T and 7 T. Proceedings of the 16th Annual Meeting ISMRM, Toronto, Ontario, Canada, 2008; 3084). ProHance DCE-MRI was similar to the controls and MS subjects. The next day, the intravascular FeO nanoparticle CA Ferumoxytol [Fe-tol; Feraheme; Amag Pharmaceuticals] was used. Points were obtained in the CA steady-states before and after three IV Fe-tol injections (Gahramanov S, Raslan A M, Muldoon L I, Hamilton B E, Rooney W D, Várallyay C G, Njus J M, M. Haluska M, Neuwelt E A. Potential for differentiation of pseudoprogression from true tumor progression with dynamic susceptibility-weighted contrast-enhanced magnetic resonance imaging using Ferumoxytol vs Gadoteridol: A pilot study. Int. J. Radiat. Oncol. Biol. Phys. 2011; 79: 514-523), fractionated into doses [1:2:4] totaling 4 mg(Fe)/kg [72 µmol(Fe)/kg, ~12 nmol(Fe-tol)/kg], each at 3 mL/s. The five minute acquisitions were initiated 120 s after each Fe-tol injection, during the steady-state period when $[CA_p]$ was uniform and constant. [The 14 hour Fe-tol plasma $t_{1/2}$ ensures $[CA_p]$ is larger after each successive injection.] All four acquisitions were completed in 40 minutes. Pre- and post-CA session $R_1$ maps were co-registered to pre-CA $T_1$-w MPRAGE maps using rigid body transformations. This protocol yielded four pharmacokinetic time points, sufficient to characterize high quality $R_{1t}$ vs. $R_{1b}$ measurements such as those in NA-brain [FIG. 6]. This sparse temporal sampling approach was originally designed for optimization of brain coverage and spatial resolution. Unlike GdHPDO3A DCE-MRI, in which $[CA_p]$ reaches large values only transiently—during the first pass [FIG. 2], Fe-tol steady-state $[CA_p]$ can attain quite high and sustained levels.

$^1H_2O$ MRI.

Magnetic resonance studies were performed using a 7 T whole body MRI instrument (Siemens, Erlangen Germany). For the dynamic contrast enhanced (DCE) MRI study, a quadrature radiofrequency (RF) coil was used for transmission, and a 24-channel phased-array receiver was used for signal reception. For the $^1H_2O$ component of the $^{31}P$ study an eight-channel phased-array 1H RF coil (Rapid Biomedical, Germany) was used for data acquisition. Subjects were positioned in the RF coil and referenced in the static magnetic field direction (z) using laser fiducial beams. After B0 shimming and RF pulse voltage calibration, four sets of whole-brain 3D Magnetization-Prepared Rapid Gradient Echo (MPRAGE) images were acquired at inversion times (TI) of 300, 900 and 2000 ms, in addition to an acquisition without inversion pulse, for quantitative $T_1$ mapping and tissue segmentation. Other imaging parameters were: field of view (FOV): 192×256×192 $mm^3$, data matrix: 192×256×96, flip angle, $\alpha=8°$, repetition time (TR)=2.5 s, echo time (TE)=2.3 ms, total acquisition time (TA)=4.5 min. High resolution 3D data sets with MPRAGE were acquired with TR=2.3 s, TI=1.05 s, $\alpha=6°$, isotropic resolution of 0.7 mm (0.8 mm for 8-channel RF coil), data matrix: 320×320×208, TA=10.8 min as well as Fluid-Attenuated Inversion Recovery (FLAIR) sequences (TR=8 s, isotropic spatial resolution of 0.8 mm, TI=2.15 s, data matrix: 280×320×208, TA=9.6 min). In some cases, high-resolution $T_2$*-weighted 2D slices were acquired too (TR=950 ms, TE=20.2 ms, $\alpha=35°$, FOV=162×226×30 $mm^3$, matrix size=598×832×20, TA=9 min 31 sec).

Plasma CA levels can achieve high instantaneous concentrations during the first-pass of a dynamic contrast enhanced (DCE) experiment and impart a large dynamic range in blood $^1H_2O$ $R_1$ values. Furthermore, the duration of the first-pass is sufficiently short that CA extravasation is not likely to be a significant issue except for the leakiest lesions. The inventors herein have collected data during the CA first-pass, when blood $^1H_2O$ $R_1$ values become sufficient to drive the blood-tissue water exchange system well out of the FXL. The $T_{1e}^{-1}$ value (defined above) is now strikingly time-dependent, and the exchange process appears to slow dramatically before appearing to speed back up.

Dynamic measurements were obtained using a single-slice inversion recovery (IR) turboflash technique that sampled magnetization at eight time points post inversion. The image matrix was 128×96 over a (256 mm×192 mm) FOV, and a 6° flip angle RF pulse selected a 10 mm transverse slice superior to the lateral ventricles. Gadoteridol (ProHance, Bracco Diagnostics, Inc) was injected at a rate of 2.5 mL/s into a catheter placed in the antecubital vein using a Medrad power injector to deliver a dose of 0.028 mmol/kg (typically ~5 mL) and followed by a 15 mL saline flush also at an injection rate of 2.5 mL/sec. For each CA injection, 50 time points were collected with a 3.8 s temporal resolution. Parametric $R_1$ maps were calculated on a voxel basis by fitting the magnitude signal intensity at each inversion time to a full Bloch simulation that incorporated all RF pulses and delays and modeled the recovery from inversion as a two-parameter single exponential using a gradient expansion algorithm.

Non-linear modeling [IDL (RSI, Inc.)] was used to extract accurate estimates of $R_{1exv}$, $v_b$, and $\tau_b$ for selected ROIs (and also on a voxel-wise basis) using the following Equation 1:

$$R_{1t}(t) = \frac{1}{2}\{(R_{1e}+R_{1b}(t)+\tau_b^{-1}+p_b/(\tau_b(1-p_b)))-[(R_{1e}-R_{1b}(t)-\tau_b^{-1}+p_b/(\tau_b(1-p_b)))^2+4p_b/(\tau_b^2(1-p_b))]^{1/2}\}$$

Equation 1:

In Equation 1, $p_b$ is the mole fraction of tissue water in blood $[v_b=p_b f_W]$, where $f_W$ is the tissue volume fraction accessible to mobile aqueous solutes (Li X, Rooney W D, Springer C S. A unified MRI pharmacokinetic theory for intravascular and extracellular contrast reagents. Magn. Reson. Med. 2005; 54: 1351-1359)]. Equation 1 is used for discrete regions of interest, and also on a voxel-wise basis. $R_{1e}=1/T_1$ of extravascular $^1H_2O$—sans transendothelial exchange, $R_{1b}(t)=1/T_1$ blood $^1H_2O$—sans transendothelial exchange, $\tau_b$=average intravascular water lifetime, and $p_b$=intravascular water fraction. The independent measure in the modeling is $R_{1b}$, the blood $^1H_2O$ $R_1$ value, which is determined by $[CA_b]$ as defined $R_{1b}(t)=R_{1b,0}+R_1[CA_b]$; with $R_{1b,0}$=the pre-contrast $R_1$ value of blood water, $R_1$ is the contrast agent relaxivity, and $[CA_b]$ is the blood concentration of the contrast agent. $R_{1b}$ was measured directly from an ROI placed fully within the sagittal sinus on $R_1$ maps. Equation 1 describes a 2SX NMR system spanning the FXL and FXR conditions, depending on $[CA_b]$. For elaboration, see Li X, Priest R A, Woodward W J, Siddiqui F, Beer T M, Garzotto M G, Rooney W D, Springer C S. Cell membrane water exchange effects in prostate DCE-MRI. *J. Magn. Reson.* 2012; 218: 77-85; and Hutchinson E B, Stefanovic B, Koretsky A P, Silva A C. Spatial flow-volume dissociation of the cerebral microcirculatory response to mild hypercapnia. *Neuroimage* 2006; 32: 520-530.

Data Acquisition.

After completion of the $^1H_2O$ MRI acquisition, the subject was removed from the magnet and the RF coil was switched to the $^{31}P$ coil. This coil is a modified 3 T $^1H$ birdcage coil (Siemens) integrated with a home-built proton loop coil, referred to as "$^1$Halo" coil [Barbara T M, Sammi M K, Rooney W D, Grinstead J. A 7 T Halo Loop Resonator for Registration of 31P MRSI. 19*th Proceedings of International Society of Magnetic Resonance in Medicine*, Montreal, Canada, 2011; 1896]. This coil is unique in its design, its axis being parallel to the main magnetic field, and has negligible perturbation to the $^{31}P$ coil sensitivity. The subject was carefully re-positioned in this novel integrated $^{31}P$/"$^1$Halo" coil setup and referenced with laser markers to be in the same location. Scout images for co-registration purposes were acquired with $^1$Halo coil tuned to proton frequency. Subsequent phosphorus RF pulse calibration and CSI data acquisition were done using the $^{31}P$ coil.

A $^{31}P$ MRSI gradient-echo FID acquisition was performed with an echo time of 2.3 ms (FOV: 250×250×200 mm$^3$, acquisition data matrix: 20×20×16, final data matrix: 32×32×16, TR=300 ms, $\alpha$=24°, spectral data points=1024, spectral width=10 kHz). An optimized sinc RF pulse of 600 is duration centered at phosphocreatine (PCr) resonance frequency (0 ppm) with a bandwidth-time product of 6.54 was used to uniformly excite the phosphorus metabolites and avoid signal contribution from outside the region of interest. This large bandwidth also minimized spatial mis-registration during the slab selection in z-direction (e.g. 1.4 mm dispersion between PCr and $\beta$-adenosine triphosphate ($\beta$-ATP) peaks). A cosine-weighted 3D-spatial phase encodings (2379 unique locations, ns=12, total 7476) were performed to minimize the acquisition time while maintaining a high signal to noise ratio with total acquisition time of 37.5 minutes. Two low resolution MRSI acquisitions (FOV: 240×240×200 mm$^3$, acquisition data matrix: 12×12×10, final data matrix=16×16×16, TR=220 ms, TE=2.3 ms, TA=4.6 min) were acquired with different flip angles (10° and 20°) to map the B1-field of the $^{31}P$ coil.

Absolute Signal measurement was demonstrated in a phantom consisting of a 6.5 mL sphere (an NMR tube with a spherical bulb at one end) containing 1M phosphoric acid and 10 mM nickel chloride solution in a 2 L plastic bottle filled with sodium chloride bath solution. The bath concentration was varied (70.3, 112.5, 150 and 200 mM) by serial dilution of 200 mM sodium chloride solution. For each concentration, RF power was calibrated for phosphorus magnetization inversion null and a $^{31}P$ spectrum acquired at calibrated 90° flip angle [sw=3000 Hz, np=2048, TR=5 s, ns=8, bath temperature=22.5 (±1.0)° C.].

Data Processing. Absolute Signal Normalization.

Spectral peak was fit to a Lorentzian line shape using AMARES routine in jMRUI software. Linewidth, signal magnitude and calibrated RF power for 90° flip angle were analyzed as a function of bath solution concentration.

Brain Tissue Segmentation.

$T_1$-weighted MPRAGE images were used to generate relaxation rate constant, $R_1$ (1/$T_1$) maps by solving for Bloch equation. Voxels representing skull, skin and other non-brain tissue were removed from the high resolution MPRAGE image data set by using a combination of edge preserving RF bias field removal (3D Gaussian smoothing kernel, sigma 10 mm) and FSL's Brain Extraction Tool (BET) [S M Smith. Fast robust automated brain extraction. *Hum. Brain Mapp.* 2002; 17: 143-155]. The RF-bias corrected image was then linearly registered to a standard space template [Montreal Neurological Institute (MNI152_$T_1$_2 mm)] and used to iteratively estimate brain mask and skull size, and generate final bias corrected image set. After thresholding for flow related signal enhancement (98th percentile image intensity value), tissue segmentation into gray matter (GM), white matter (WM) and cerebrospinal fluid (CSF) was carried out using FMRIB's Automated Segmentation Tool (FAST) using standard space tissue prior probability estimates to initialize the process.

Tissue definitions were improved by using complementary information available from other additional scans and atlas based image processing routines in FSL [Berlow Y A, Sammi M K, Barbara T M, Grinstead J, Bourdette D, Rooney W D. Quantitative Volumetrics of Multiple Sclerosis Brain from 7 T MRI., 2013; 4692]. WM definition was improved by using an upper bound of 2.0 s for WM $T_1$ from the co-registered $R_1$ maps to the MPRAGE image set. FMRIB's Integrated Registration and Segmentation Tool (FIRST), which uses shape and intensity based models, was used to define GM subcortical brain structures [B Patenaude, S M Smith, D N Kennedy, M Jenkinson. A Bayesian model of shape and appearance for subcortical brain segmentation. *Neuroimage* 2011; 56: 907-922]. White matter lesions were identified using a semi-automated technique. Voxel clusters were identified automatically that had hypointense values within the atlas based WM spatial distribution. These clusters were manually evaluated and edited for the corresponding hyperintensities on the coregistered FLAIR image in order to obtain final white matter lesion volumes. Tissue volumes were normalized using a scaling factor based on skull size [S M Smith. Fast robust automated brain extraction. *Hum. Brain Mapp.* 2002; 17: 143-155]. Skeletal muscle was defined on the $R_1$ maps using the registered total phosphorous signal image data (see below). Areas of high phosphorus signal in non-brain voxels that had $T_1$ times ranging from 1.4 s to 3.3 s were defined as muscle regions. Group differences in normalized brain volumes were analyzed with analysis of covariance adjusting for age.

$^1H_2O$ MRI and $^{31}P$MRSI Data Co-Registration.

Scout images, acquired in the same reference frame as phosphorus spectroscopic images, were used as reference images to co-register with anatomic proton image sets in FSL co-registration tool—FLIRT [M Jenkinson, P Bannister, M Brady, S Smith. Improved Optimization for the Robust and Accurate Linear Registration and Motion Correction of Brain Images. *Neuroimage* 2002; 17: 825-841]. The transformation matrix obtained from this co-registration was used to align segmented tissue images to $^{31}P$ spectroscopic data.

$^{31}P$ Spectral Data Processing.

Spectral data showed a significant baseline roll due to a finite delay between RF pulse and fid acquisition (2.3 ms). Therefore, a time-domain fitting-AMARES routine-in jMRUI 3.0 software was used for processing. Software routines developed in Matlab were used to create input files for batch processing and analyze jMRUI results. In AMARES, linewidths of ATP peaks were constrained to be equal, J-coupling of 16.6 Hz and peak positions were soft-constrained to be within ±30 Hz of the expected spectral frequency offset except for PCr and inorganic phosphate ($P_i$) peaks. Fitted resonance peak amplitudes were corrected for $B_1$ and $T_1$-saturation effects based on the steady-state signal calculation. Apparent $T_1$ values of phosphate metabolites from the work of Lei and co-workers [A. Haase. Snapshot FLASH MRI. Applications to T1, T2, and chemical-shift imaging. Magn Reson Med. 1990 January; 13(1):77-89] in human brain were used, except for the phosphocholine (PC) peak (not measured) which was assumed to be 4.0 s (similar to glycerol-3-phosphocholine (GPC) peak). In addition, transmitter amplitude correction was carried out to normalize differential coil loading by each subject as well as gain for the receiver chain.

The corrected signal, S, is given by the following Equation 2 below, where $S_m$, is the measured signal and $C_{T1}$, $C_{B1}$, $C_{load}$ and $C_{gain}$ are the correction terms for $T_1$, $B_1$, load and receiver gain, respectively.

$$S=S_m*C_{T1}*C_{131}*C_{load}*C_{gain} \qquad \text{Equation 2:}$$

Tissue Contribution Maps and Spectroscopic Data Analysis.

To account for the signal contribution from different tissue types to the spectroscopic voxels, convolution of the segmented tissue images with the spatial response function (SRF) (popularly known as point spread function (PSF)) of the spectroscopic acquisition was carried out. SRF has a full width at half maximum of 2.77 cm in x and y directions, and 2.86 cm in z direction. This yields an effective voxel volume of ~11.46 mL.

A large volume of interest (VOI) in supratentorial brain region superior to the ventricles was defined in the brain atlas to confine the data analysis to the same brain region and is without any significant $B_1$- and $B_0$-inhomogeneity effects. This VOI was transformed into each subject's brain region using the co-registration transformation matrix generated during brain tissue segmentation. Within this subject-specific VOI, any voxels that had significant SM (1%), less than 20% tissue contribution or with any zero peak amplitudes were excluded. Of the remaining voxels for all the subjects, a linear mixed-effect regression analysis of total phosphorus signal as well as individual phosphorus metabolite signal dependence on tissue type and group (MS versus HC) was carried out using Equation 3 below in statistical software package R.

$$S_{Metabolite}=GM+WM+Group+GM*Group+\\WM*Group+\varepsilon_{Subject}+\varepsilon_{random} \qquad \text{Equation 3:}$$

This model analyzed tissue and group interactions as well as random errors that are global ($\varepsilon_{random}$) or subject specific ($\varepsilon_{subject}$). A separate regression analysis for signal ratios (metabolite/Total $^{31}$P signal) was also modeled for a comparison. The projected metabolite peak amplitudes or ratios were calculated from the model for the pure tissue types (GM and WM).

For brain region specific analysis, caudate and thalamus regions were identified in the native space using FIRST [B P Hills, P S Belton, "NMR Studies of Membrane Transport," *Ann Rep NMR Spectros* 21: 99-159 (1989)] and spectra from these regions were analyzed for the subject group differences.

Results

Cerebral $\tau_b$ Values in Normal and MS Brain.

FIG. 2 displays example 7 T $^1$H$_2$O inversion recovery (IR) turboflash DCE-MRI data, and shutter-speed paradigm (SSP) analysis (38), for a 22 y F control subject. Panels A and B show $R_1$ time-courses (50 points, 2.3 s apart): 0.03 mmol/kg of GdHPDO3A (Gadoteridol) was injected (3 mL/s) at $^{35}$ s (arrows). The FIG. 2A data are from a blood (sagittal sinus) ROI while those in FIG. 2B arise from the WM ROI indicated by circles in panel D; axial $R_1$ maps before and after CA administration. The CA passes through the brain without extravasation. Panel C plots the $R_{1b}$-dependence of $R_{1t}$ from FIGS. 2A,B. If the tracer paradigm (TP) obtained, the $R_{1t}$,$R_{1b}$ plot would be linear. This is indicated by the FIG. 2C dashed line. The data are not linear, and are well fitted with a 2SX [two-site-exchange] SSP version, solid curve, with $\tau_b$=560 ms, $v_b$=0.018, and $R_{1exv}$=0.85 s$^{-1}$ [the pre-exchange extravascular $^1$H$_2$O $R_1$]. If the TP is forced to the data, the dashed FXL [fast-exchange-limit] line must pivot about their origin, and its slope, $v_b$, is significantly decreased. In this case, the TP gives a $v_b$ value of 0.015; a 17% underestimation. Of course, TP also denies access to $\tau_b$, since it assumes it zero.

Figures 3A, 3B, 3C:
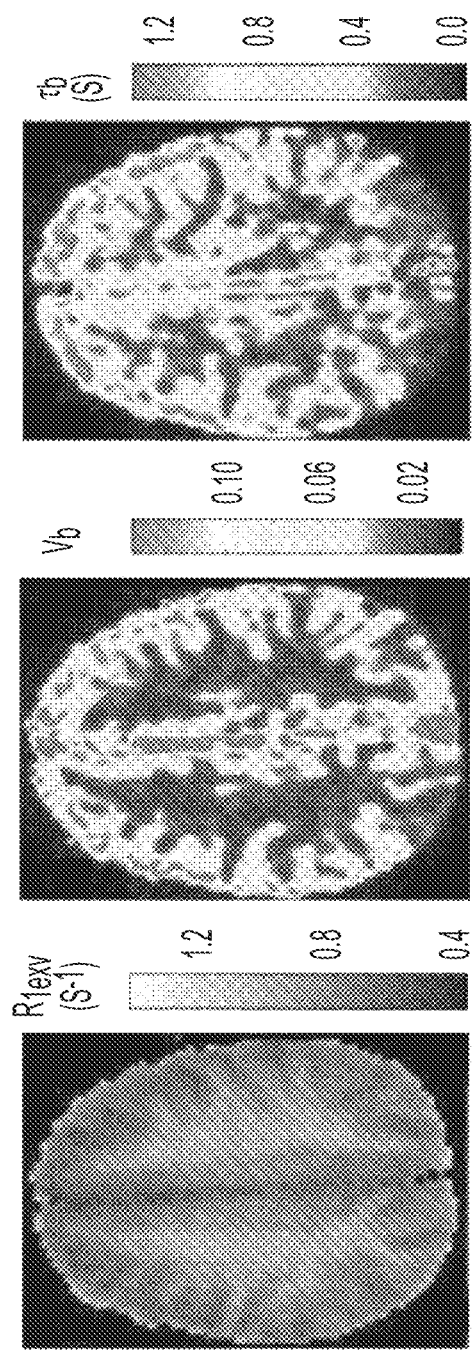
FIG. 3 shows example Shutter-Speed Paradigm (SSP) parametric maps for a 22 y F healthy control subject.

FIG. 3 displays axial pixel-by-pixel parametric maps for the FIG. 2 subject. In particular, FIG. 3 shows SSP parametric maps for 22 y F healthy control subject; (a) shows the axial $R_{1exv}$ map (pre-exchange extravascular $R_1$), (b) shows the $v_b$ map, and (c) the $\tau_b$ map. The biomarkers are: $R_{1exv}$ (a), $v_b$ (b), and $\tau_b$ (c): elevated values in the subarachnoid CSF space are not meaningful. The $v_b$ map exhibits greater GM (~0.03) than WM (~0.01) values. These rather well approximate absolute $v_b$ fractions—unlike [Dynamic-Susceptibility-Contrast] DSC-MRI relative (rCBV) values. Such maps are thus quite important in their own right. However, they exhibit the extensive nature of the $v_b$ property discussed above. The larger GM $v_b$ value reflects the well-known greater GM vascularity. But, as also discussed above, $\tau_b$ is an intensive parameter independent of $v_b$. It is therefore very encouraging that the $\tau_b$ map (FIG. 3c) is more uniform (~375 ms) across the brain, with only slightly smaller values in WM. Previous approaches have not used $\tau_b$ map and FIG. 3c may be the first $\tau_b$ map ever presented.

Figure 4:
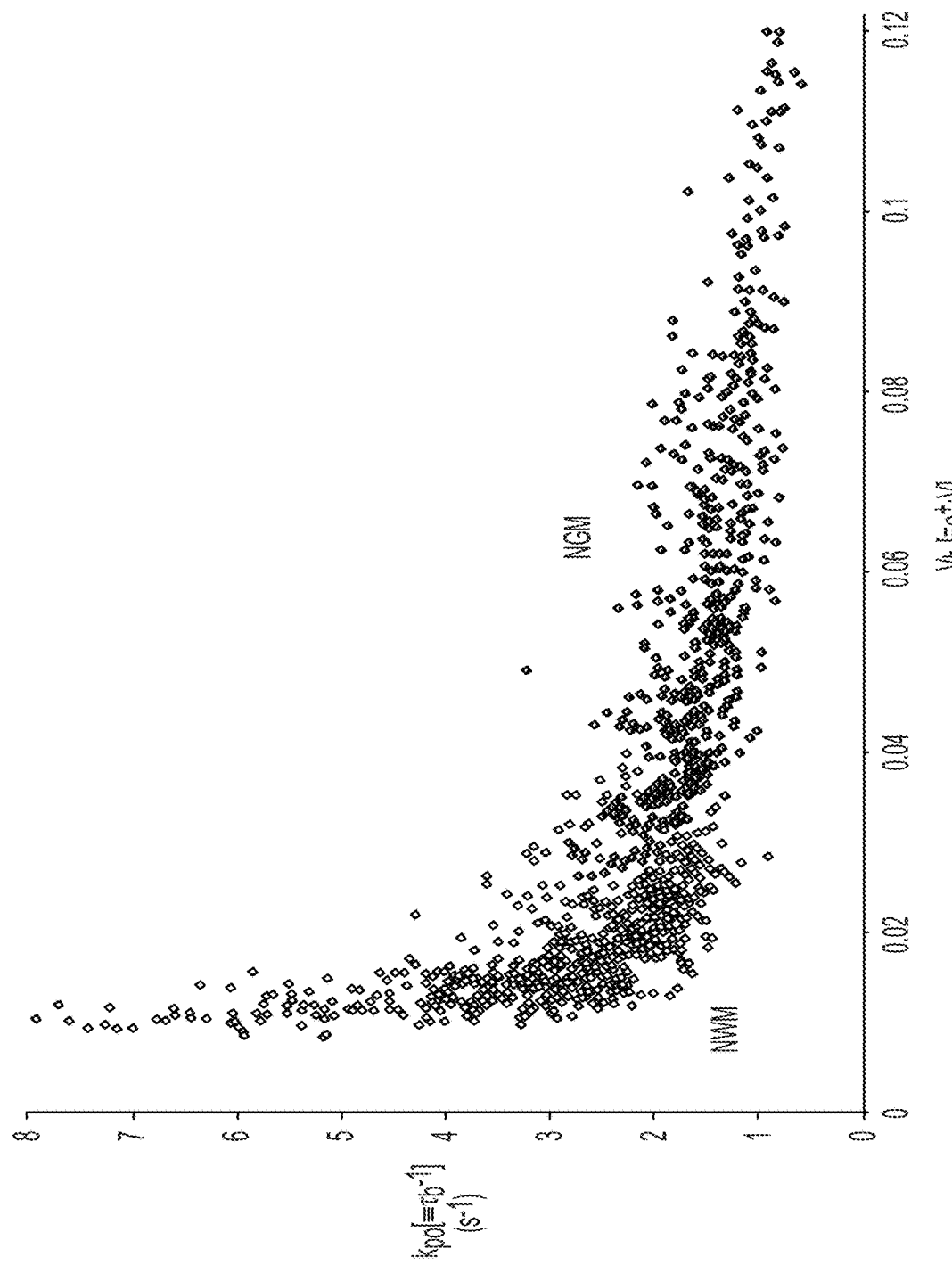
FIG. 4 shows an example scatter plot of $k_{po}$ [$\tau_b^{-1}$] values vs. $v_b$ values for the pure normal white matter and gray matter pixels from FIG. 3.

FIG. 4 shows the pixel-by-pixel $k_{po}$ vs. $v_b$ scatter plot of much of the FIG. 3b,c data. The pixels were chosen from 2500 in a square ROI centered on and covering ~75% of the FIGS. 2,3 brain image slice. The $R_{1exv}$ relaxation rate constant spectrum [histogram] was used to assign the pixels (74). The 649 pixels with $R_{1exv}$ values between 0.80 and 0.92 s$^{-1}$ were identified as NWM, and yield the pink FIG. 4 points. The 670 pixels between 0.62 and 0.72 s$^{-1}$ are labeled NGM, and give the olive FIG. 4 points. As expected, the NWM points cluster below $v_b$=0.02. The NGM points cluster about a $v_b$ value (0.06) somewhat greater than expected, because a number represent voxels with some partial-volume-averaging of vessels larger than capillaries especially near the cortical surface [FIG. 3c]. Interestingly, the NGM $k_{po}$ [$\tau_b^{-1}$] values are essentially independent of $v_b$, and the NWM $v_b$ values are essentially independent of $k_{po}$. The basically horizontal and vertical orthogonal NGM and NWM clusters are consistent with parameters not numerically correlated by data fittings. The interesting trends seen in FIG. 4 are physiological. The parameter $v_b$=$\rho^\dagger \bullet$V. By definition, $k_{po}$ is $\rho^\dagger$-independent, and is dependent on only $V^{1/2}$. Since $k_{po}$ is experimentally independent of $v_b$, $k_{po}$ variations must be due to $P_W^\dagger$ variations [Background]. These are large in NWM voxels but $v_b$ is small and apparently regulated [likely $\rho^\dagger$ regulation], while $k_{po}$ seems regulated in NGM voxels. The very slight downward slope of the green point cluster at larger $v_b$ is due to the partial-volume-averaging mentioned above. Larger $v_b$ values reflect larger mean r values, and there is a slight $k_{po}$ decrease due to this. But, mostly, $k_{po}$ is constant in NGM.

In consideration of population averages, Table 1 presents (region-of-interest) ROI biomarker values averaged for six healthy controls [4F/2M 30 (±10) y] and also for six relapsing remitting MS (RRMS) subjects [4F/2M 46 (±7) y], who were presenting with inactive WM lesions. Precision is generally quite good: the standard deviations listed are due mostly to inter-subject variation. The fact that the $\tau_b$ values in normal WM and GM (NWM and NGM) are more similar than the $v_b$ values is due to the aforementioned intensive nature of $\tau_b$, and may also suggest that, in the normal brain, metabolic activity per gliovascular unit is constant. This, in turn, hints that $\tau_b$ may be dominated by the $P_W$(active) contribution (see below). The $R_{1exv}$ values are reduced in NGM, NAGM, and MS lesions because of decreased macromolecular volume fractions. The $v_b$ values are increased in NAWM, NAGM, and decreased in MS lesions. Perhaps most interesting is the fact that $\tau_b$ is increased in MS-NAWM as well as in MS-NAGM and even more-so in lesions.

TABLE 1

SSP DCE-MRI ($^1H_2O$)

| | $R_{1exv}$ (s$^{-1}$) | $v_b$ | $\tau_b$ (s) | $k_{po}$ [$\tau_b^{-1}$] (s$^{-1}$)$^c$ |
|---|---|---|---|---|
| Healthy Controls (n = 6)$^a$ | | | | |
| NWM | 0.831 (±0.021) | 0.014 (±0.002) | 0.35 (±0.04) | 3.2 (±0.56) |
| NGM | 0.679 (±0.015) | 0.031 (±0.004) | 0.41 (±0.06) | 2.9 (±0.59) |
| Relapsing Remitting MS (n = 6)$^a$ | | | | |
| NAWM | 0.810 (±0.022) | 0.019 (±0.002) | 0.48 (±0.05) | 2.2 (±0.20) |
| NAGM | 0.672 (±0.009) | 0.045 (±0.004) | 0.50 (±0.03) | 2.0 (±0.13) |
| lesion | 0.624 (±0.009) | 0.012 (±0.003) | 0.59 (±0.14) | 1.8 (±0.45) |
| Glioblastoma (n = 5)$^b$ | | | | |
| NA-frontal WM | 1.10 (±0.027) | 0.008 (±0.001) | 0.44 (±0.04) | 2.6 (±0.31) |
| NA-thalamus | 0.90 (±0.009) | 0.017 (±0.001) | 0.38 (±0.05) | 2.9 (±0.37) |
| NA-putamen | 0.78 (±0.013) | 0.012 (±0.005) | 0.43 (±0.03) | 2.5 (±0.22) |
| tumor | 0.67 (±0.013) | 0.046 (±0.013) | ≥5.6 | ≤0.18 |

$^a$ProHance, 7T;
$^b$Ferumoxytol, 3T;
$^c$($k_{io}$) [=($\tau_b$)$^{-1}$].
Uncertainties are (±SEM).

For a cylindrical capillary, $k_{po}=2\cdot P_W^\dagger \cdot r^{-1}$: the quantity r is a 1D measure of capillary size. With a conservatively large r value [3 μm], $k_{po}=0.7\ P_W^\dagger$ [$k_{po}$ in s$^{-1}$, $P_W^\dagger$ in μm/s]. With a typical $P_W^\dagger$ value [2 μm/s], $k_{po}=4\ r^{-1}$ [r in μm]. Thus, $k_{po}$ is linearly related to $P_W^\dagger$ and linearly related to $r^{-1}$, with different coefficients. Below, concomitant relative [%] changes in the population-averaged $v_b$ and $k_{po}$ parameters for the NGM→NAGM [Table 1] transition are compared. A deductive quantitative analysis shows that the $k_{po}$ decrease is dominated by a $P_W^\dagger$ decrease. The analogous exercise indicates an even greater $P_W^\dagger$ decrease in MS-NAWM. $k_{po}$ [$\tau_b^{-1}$] is dominated by the $P_W^\dagger$ factor, not the $r^{-1}$ factor.

A conservative consideration of the MS-induced GM $\tau_b$ change—the smallest in Table 1—yields ($\tau_b$(NAGM))$^{-1}$/($\tau_b$(NGM))$^{-1}$=2.0 s$^{-1}$/2.5 s$^{-1}$=0.80: the NAGM $k_{po}$ is reduced by 20% from that in NGM. From the fundamental relationships given above, ($\tau_b$(NAGM))$^{-1}$/($\tau_b$(NGM))$^{-1}$={$P_W$(NAGM)/$P_W$(NGM)}($r_{NGM}$/$r_{NAGM}$), where $r_{NGM}$ and $r_{NAGM}$ are the mean capillary radii in NGM and NAGM tissues, respectively. Capillaries dominate vascular volume in most voxels [M Unekawa, M Tomita, Y Tomita, H Toriumi, K Miyaki, N Suzuki, "RBC Velocities in Single Capillaries of Mouse and Rat Brains are the Same, Despite a 10-Fold Difference in Body Size," Brain Res 1320: 69-73 (2010)]. If the water permeability coefficients were equal [$P_W$(NAGM)=$P_W$(NGM)], then $r_{NAGM}$=1.25 $r_{NGM}$. It seems unlikely that NAGM capillaries would dilate to 125% the radius of those in NGM: generally brain microvessels do not dilate or constrict significantly. Recall, also, that r is the average radius. If $r_{NAGM}$=$r_{NGM}$, $P_W$(NAGM)=0.8 $P_W$(NGM).

It is extremely difficult, and invasive, to determine individual capillary radii in vivo. However, limits of their changes can be estimated. The blood volume fraction $v_b$=(n/V$_T$)V=ρ'V, where (n/V$_T$) is the number of capillaries in the voxel or ROI total volume, the number capillary density, ρ' [typically a few hundred/μL], and V is the mean individual capillary volume. Assuming capillaries are cylindrical, r~V$^{1/2}$ and the ratio {$v_b$(NGM)/$v_b$(NAGM)}$^{1/2}$={ρ'$_{NGM}$/ρ'$_{NAGM}$}$^{1/2}$($r_{NGM}$/$r_{NAGM}$). Taking $v_b$(NGM) as 0.031, and $v_b$(NAGM) as 0.045 (Table 1) gives {$v_b$(NGM)/$v_b$(NAGM)}$^{1/2}$=0.83. Though unlikely (as stated), if $r_{NAGM}$ was actually 1.25 $r_{NGM}$, then ρ'$_{NAGM}$=0.93 ρ'$_{NGM}$: the NAGM capillary density would be almost the same as that of NGM. If $r_{NAGM}$=$r_{NGM}$, then ρ'$_{NAGM}$=1.45 ρ'$_{NGM}$ and capillary density is increased by 45% in the disease. This seems plausible and explains the $v_b$ ratio. Recall, however, that capillary density does not directly affect the intensive $P_W$ value.

Decreased $k_{po}$ in the MS Lesion.

Figure 5:
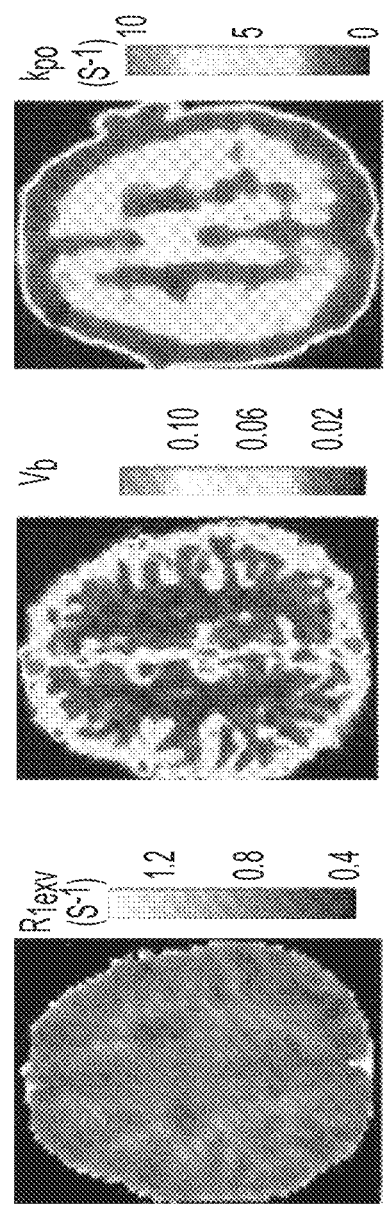
FIG. 5 shows example SSP maps for a 52 y F advanced RRMS subject.

In non-enhancing MS lesions, the $k_{po}$ value is decreased even further: the average for the six Table 1 RRMS subjects is 1.8 s$^{-1}$. However, those represent relatively early-stage disease. FIG. 5 shows results for a 52 y F late-stage RRMS subject. Quite large chronic demyelinated WM lesions appear hypointense in the $R_{1exv}$ map [5a]—indicating extensive macromolecular loss, consistent with demyelination and gliosis. These lesions are many months past their last high CA-enhancement stage. The $v_b$ map [5b] is rather similar to that of the control [3b], except reduced (<0.01) in lesion areas and NAWM. However, the $k_{po}$ map [5c] is dramatically altered. Unlike NWM [FIG. 3c], the WM region is extremely hypointense. The $k_{po}$ values in the lesions themselves (~1.5 s$^{-1}$) are decreased below the MS-NAWM mean (2.2 s$^{-1}$) and even the RRMS lesion mean (1.8 s$^{-1}$) [Table 1]. Furthermore, compared with RRMS NAGM mean (2.0 s$^{-1}$) [Table 1], the $k_{po}$ values (~2.9 s$^{-1}$) are considerably increased in this advanced subject NAGM. [It is hard to discern the NAWM situation because the lesions are so large.]

Decreased $k_{po}$ in the Glioblastoma multiforme (GBM) Tumor.

Figure 6:
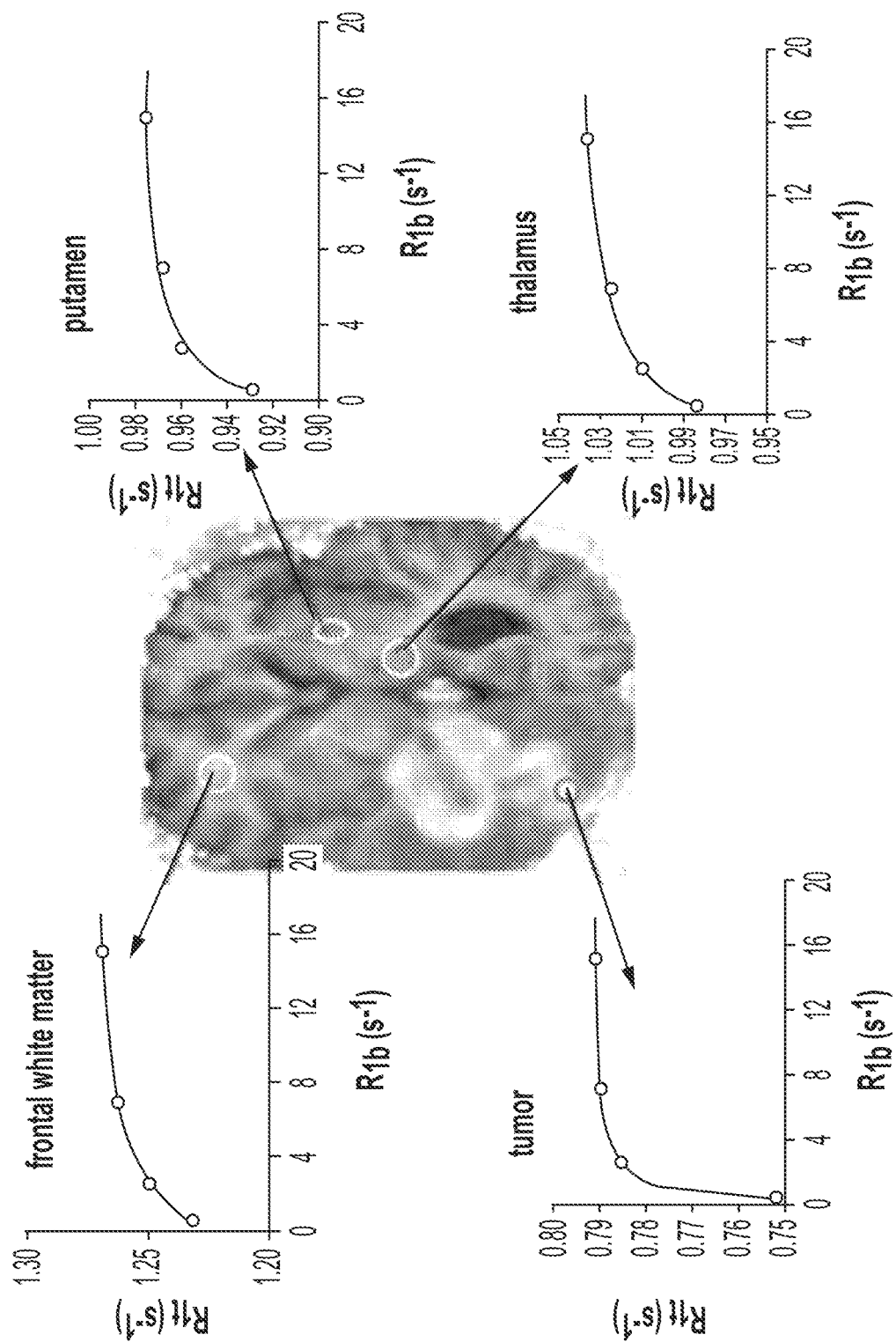
FIG. 6 shows example GBM $^1H_2O$ DCE-MRI data arising from a 52 y M glioblastoma subject.

For GBM capillaries, clinical monomeric Gd(III) chelate CAs extravasate too rapidly to allow $k_{po}$ determination. Thus, we used the intravascular, coated superparamagnetic iron oxide nanoparticle Fe-tol as CA (Gahramanov S, Raslan A M, Muldoon L I, Hamilton B E, Rooney W D, Várallyay C G, Njus J M, M. Haluska M, Neuwelt E A. Potential for differentiation of pseudoprogression from true tumor progression with dynamic susceptibility-weighted contrast-enhanced magnetic resonance imaging using Ferumoxytol vs Gadoteridol: A pilot study. Int. J. Radiat. Oncol. Biol. Phys. 2011; 79: 514-523). This agent has a molecular mass of 750,000 Da [10$^3$ times that of GdHPDO3A; 588 Da]. Its K$^{trans}$ in normal and NA brain tissue is ~10$^{-8}$ min$^{-1}$. [The biomarker K$^{trans}$≈$P_{CA}^\dagger$S, where $P_{CA}^\dagger$ is the endothelial CA permeability coefficient.]During the first pass, it remains intravascular even in very advanced GBM tumors with extremely permeable capillaries. FIG. 6 shows results from a 52 y male GBM subject. In the center is an $R_1$ map obtained 30 min after GdHPDO3A injection. The large CA-enhancing tumor is clearly visible at the lower left. Twenty-four hours after GdHPDO3A, the subject received IV Fe-tol. Inset are data (points) obtained from four representative ROIs [frontal WM, thalamus, putamen (white ellipses), and tumor (red circle)] during the Fe-tol injections. Each plot shows the $R_{1b}$-dependence of $R_{1t}$ [as in FIG. 2C]. If the TP [$\tau_b \rightarrow 0$] obtained, the $R_{1t}, R_{1b}$ plots would be linear. None are: and all are well fitted by Eq. [1] 2SX SSP expression curves with $R_{1exv}$, $v_b$, and $\tau_b$ varied. The $R_{1exv}$, $v_b$, and $\tau_b$ parameter values returned are: 1.24 s$^{-1}$, 0.008, 0.29 s [frontal WM]; 0.99 s$^{-1}$, 0.013, 0.32 s [thalamus]; 0.94 s$^{-1}$, 0.014, 0.43 s [putamen], and 0.77 s$^{-1}$, 0.028, 1.52 s [tumor]. For five subjects, the population- and ROI-averaged parameter values are given in Table 1. For this 3 T study the $R_{1exv}$ values are greater than the normal and MS brain 7 T entries. Tissue macromolecular relaxivity is greater at smaller field (Rooney W D, Johnson G, Li X, Cohen E R, Kim S-G, Ugurbil K, Springer C S. Magnetic field and tissue dependences of human brain longitudinal 1H$_2$O relaxation in vivo. Magn. Reson. Med. 2007; 57: 308-318). In the GBM-NA brain, the $v_b$ values are generally smaller than normal. They are large in the tumor.

The $k_{po}$ values in the GBM-NA brain are rather normal. This supports the general accuracy of the Fe-tol protocol. [The latter favored spatial resolution over pharmacokinetic temporal resolution, just the opposite of the GdHPDO3A protocol used to obtain the Table 1 normal and MS-NA values.] However, the FIG. 6 tumor tissue $k_{po}$ is decreased by more than a factor of five. The example tumor ROI shows why: the $R_{1t}, R_{1b}$ plot has a much sharper hyperbolic shape. Though the Fe-tol protocol yielded only four pharmacokinetic points, this behavior is confirmed by the population [n=5] averaging [Table 1], where the tumor $k_{po}$ decrease is over an order of magnitude. Since there is likely a family of fittings of the four data points for which the $k_{po}$ values are even smaller, it is best to consider the Table 1 GBM tumor $k_{po}$ entry as an upper limit. The very large GBM tumor tissue $\tau_b$ values were unexpected. Future Fe-tol protocols will acquire more than four points while still achieving full brain coverage and good spatial resolution.

That $k_{po}$ decreases in MS lesions and in GBM tumors is very significant. It is shown below that these are due to $P_W^\dagger$ decreases. However, these are both tissues well-known to have leaky capillaries: $K^{trans}$ is clearly increased in each. Furthermore, the increase of the $P_{CA}^\dagger$ factor dominates $K^{trans}$. This is what is meant by the colloquial phrase "increased capillary permeability." The facts that $P_W^\dagger$ decreases while $P_{CA}^\dagger$ increases mean that water and CA molecules do not exchange across the capillary wall by the same mechanism.

$\tau_{exv}$ Values.

Finally, equilibrium mass action demands: $\tau_{exv} = \tau_b[(1-p_b)/p_b]$; where Pb is the mole fraction of water that is vascular [$=v_b/f_W$]. Combining the Table 1 $v_b$ and $\tau_b$ values, $\tau_{exv}$ values of 19 s and 10 s for NWM and NGM, respectively, are obtained. These are comparable to the first-order lifetime, 45 s, calculated (Labadie C, Lee J-H, Vé tek G, Springer C S. Relaxographic imaging. J. Magn. Reson. B 1994; 105: 99-112) from the observed 31 s $t_{1/2}$ for brain parenchyma $^{15}OH_2$ intravasation. As detailed above, this 2SX expression does not require the assumption that parenchymal water is "well-mixed," only that its MR systems are in their FXL conditions.

Figure 7:
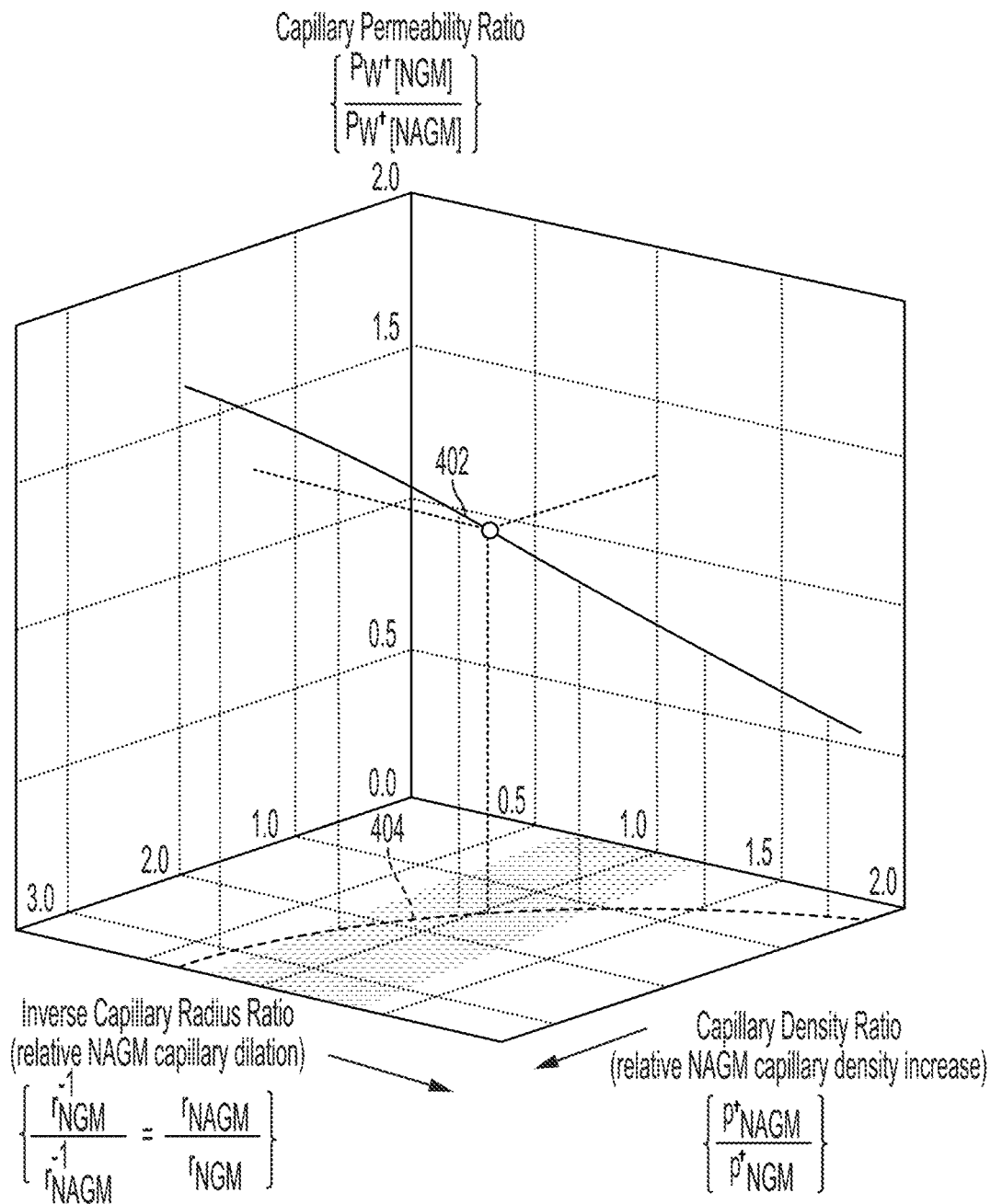
FIG. 7 shows example biomarker inter-relationships for the population-averaged normal gray matter (NGM) and multiple sclerosis (MS)-normal appearing gray matter (NAGM) regions of interest (ROIs).

FIG. 7 shows biomarker inter-relationships for the population-averaged NGM and NAGM ROIs in Table 1. Thus, $(\tau_b[\text{NAGM}])-1/(\tau_b[\text{NGM}])-1=0.80$, and $(v_b[\text{NAGM}])/(v_b[\text{NGM}])=1.5$, where $\tau_b$ is the mean capillary water lifetime and $v_b$ the capillary volume fraction. The red curve (labeled 402) is the trace of points that satisfy these relationships simultaneously, in a 3D space of brain tissue properties. The vertical axis is $P_W[\text{NGM}]/P_W[\text{NAGM}]$, the capillary water permeability coefficient ratio. The oblique axes are the inverse capillary radius ratio, $r_{NGM}^{-1}/r_{NAGM}^{-1}$, and the capillary density ratio, $\rho'_{NAGM}/\rho'_{NGM}$. The coordinates of the curve in regions of reasonable $r_{NGM}^{-1}/r_{NAGM}^{-1}$ (gray shading) are consistent only with $\tau_b$ being dominated by the $P_W$ factor.

The solid red curve (labeled 402) in FIG. 7 is the trace of all points that simultaneously satisfy the $\{P_W(\text{NAGM})/P_W(\text{NGM})\}(r_{NGM}, r_{NAGM})=0.80$ and $\{\rho'_{NGM}/\rho'_{NAGM}\}^{1/2}(r_{NGM}/r_{NAGM})=0.83$ relationships of the Table 1 ROI averaged values. The axes are: $P_W[\text{NGM}]/P_W[\text{NAGM}]$ (vertical), $r_{NGM}^{-1}/r_{NAGM}^{-1}$ (Inverse capillary Radius Ratio), and $\rho'_{NAGM}/\rho'_{NGM}$ (capillary Density Ratio). This result is informative. The curve does not pass through the $r_{NGM}=r_{NAGM}$, $\rho'_{NGM}=\rho'_{NAGM}$ point. Generally, one would expect $\rho'$ to be more altered than r in a chronic condition; and especially since r is the mean of all capillaries in the ROI. A conservatively generous range for $r_{NGM}^{-1}/r_{NAGM}^{-1}$ from 1.25 to 0.75 is shaded gray in the FIG. 7 horizontal plane. [The dot-dashed red projection labeled 404 shows that the allowed $\rho'_{NAGM}/\rho'_{NGM}$ values vary from 0.92 to 2.6 in the gray shaded region. Capillary density does not affect $P_W$, only the estimation of r.] The $P_W[\text{NGM}]/P_W[\text{NAGM}]$ values (vertical) over the gray shaded region vary from 1.0 to 1.7 (a 70% increase). This hints that overall $P_W$ is reduced in MS-NAGM (probably with some capillary density increase).

The analogous exercise indicates an even greater $P_W$ decrease in MS-NAWM. However, is it the $P_W$(passive) contribution [e.g., aquaporin level], the $P_W$(active) contribution, or both, that is reduced? It is very interesting that a recent $^{23}$Na MRSI study reports increased TSC in both MS-NAGM and MS-NAWM [M. Inglese, G. Madelin, N. Oesingmann, J. S. Babb, W. Wu, B. Stoekel, J. Herbert, G. Johnson, "Brain Tissue Sodium Concentration in Multiple Sclerosis: A Sodium Imaging Study at 3 Tesla," Brain 133, 847-857 (2010)]. Increased TSC usually reflects increased [Na$_i$]. It is possible that neuronal compromise decreases gliovascular unit NKA activity. This would account for an [Na$_i$] increase, and increased $\tau_b$ if the latter was dominated by $P_W$(active). Another way to test this hypothesis is with $^{31}$P MRSI.

Brain GM [HEP] Values are Reduced in MS.

Figure 8B:
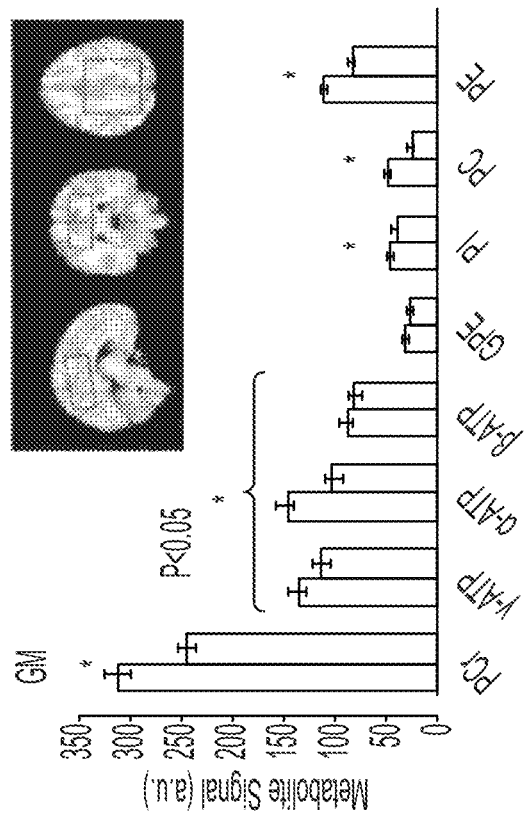
FIG. 8 shows example summarized 7 T$^{31}$P MRSI region of interest (ROI) metabolite concentrations in healthy controls and MS subjects segmented by $^1H_2O$ MRI into "pure" white matter (WM) and gray matter (GM).
Figure 8A:
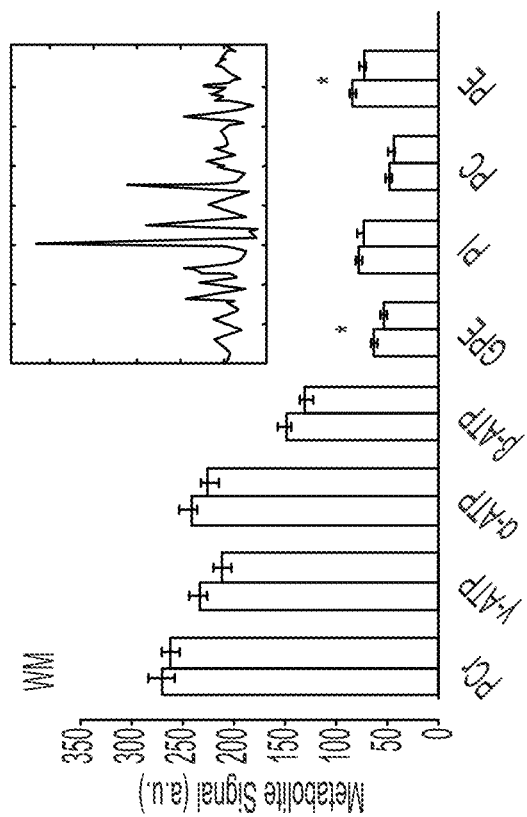

FIG. 8 shows summarized 7 T $^{31}$P MRSI ROI metabolite concentrations in healthy controls (n=12, left bars, blue) and MS (n=15, right bars, red) subjects segmented by $^1$H$_2$O MRI into "pure" WM (A) and GM (B). A sample single voxel (~2 mL) $^{31}$P spectrum and the 80-voxel ROI (~160 mL) are inset in 5A and 5B, respectively. Symbols: PCr, phosphocreatine; ATP, adenosine triphosphate; GPC, glycerophosphocholine; GPE, glycerophosphoethanolamine; P$_i$, inorganic phosphate; PC, phosphocholine; PE, phosphoethanolamine. The error bars represent ±1 standard error. Between-group differences in signal levels are indicated with asterisks. Note the significant MS PCr and ATP decreases in GM, but not WM. In particular, FIG. 8 summarizes Applicants' 7 T $^{31}$P MRSI results for healthy control [7F/5M, 48 (±10) y] and MS [10F/5M, 47 (±10) y, RRMS] subjects. Serial 1H and $^{31}$P MR data were acquired. A sample single voxel (~2 mL) spectrum and the 80-voxel ROI (~160 mL) are inset in 5A and 5B, respectively. The histograms present ROI results, segmented by the $^1$H$_2$O MRI into "pure" WM (5A) and GM (5B) metabolite concentrations for control (left bars, blue) and MS (right bars, red) subjects. It is extremely interesting that the major finding is decreased ATP ($\gamma, \alpha$, and $\beta$ signals) and PCr, and in MS-NAGM only. The concentrations decrease in rough proportion, consistent with the maintenance of overall ATP/PCr equilibrium, and very supportive of the $P_W$(active) dominated $\tau_b$ increase interpretation above. Some metabolic rates are known for neuronal cells in normal homeostasis. For 1 μL_(approximate $^1H_2O$ MR voxel) of "pure" NGM, the flux of ATP synthesis (mostly by ox-phos, FIG. 1) is 0.16 nmol/s, and of course the consumption rate is the same. The fluxes between ATP and phosphocreatine (PCr) are much larger, 1.15 nmol/s in each direction: integrated over the neuron, ATP and PCr are in effective equilibrium. If the rate of MS-NAGM ATP production by neuronal oxidative phosphorylation is diminished by mitochondrial compromise ["metabolic hypoxia"], then the ATP (and PCr) level will fall, NKA activity will decrease, and $\tau_b$ would increase. Since $\tau_b$ increases also in MS-NAWM (Table 1), while ATP and PCr do not decrease (FIG. 8A), perhaps $\tau_b$ is the more sensitive measure of metabolic distress.

FIG. 9 shows SSP parametric maps for a 52 y F advanced RRMS subject. FIG. 9(a) shows an axial $^1H_2O$ $R_{1exv}$ map, where the extensive chronic lesions are hypointense. [The small circular dark region in the right (image left) WM is an artifact.] FIG. 9(b) shows a $v_b$ map which displays substantial reductions (<0.01) in the lesion areas. FIG. 9(c) shows a $\tau_b$ map which displays a striking contrast between lesion and NABT with $\tau_b$ values strongly elevated in lesion areas and reduced in cortical regions compared to the control (FIG. 9c). This patient has quite large chronic demyelinated WM lesions, which appear hypointense in the $R_{1exv}$ map (6a)—indicating extensive demyelination and gliosis. These are many months past the maximum CA-enhancement stage [more on this below]. The $v_b$ map (6b) is rather similar to that of the control (FIG. 9b), except reduced (<0.01) in lesion areas and NAWM. However, the $\tau_b$ map (6c) is dramatically altered. The $\tau_b$ values are significantly decreased (~350 ms) in MS-NAGM. It is hard to discern the MS-NAWM situation because the lesions are so large in this case. On the other hand, the lesion $\tau_b$ values are strongly elevated (~650 ms) above those in the MS-NAWM. This manifests as significantly higher conspicuity for these chronic lesions than is the case in T$_1$-weighted images or the $K^{trans}$ map (not shown) [$K^{trans}$ is the $P_{CA}S$ product].

The inventors herein pursue first the significance of the increased lesion $\tau_b$ the effect of transendothelial water exchange in the demyelinated MS lesion. To approach this, consider MS lesion $K^{trans}$ values in general. The DCE-MRI enhancement of MS lesions is transient during disease progression, increasing and decreasing with time-constants of months. The $K^{trans}$ values are heterogeneous within the lesion, and can reach magnitudes over $10^{-2}$ min$^{-1}$. To obtain these, a different SSP version must be used.

Figures 10A, 10B:
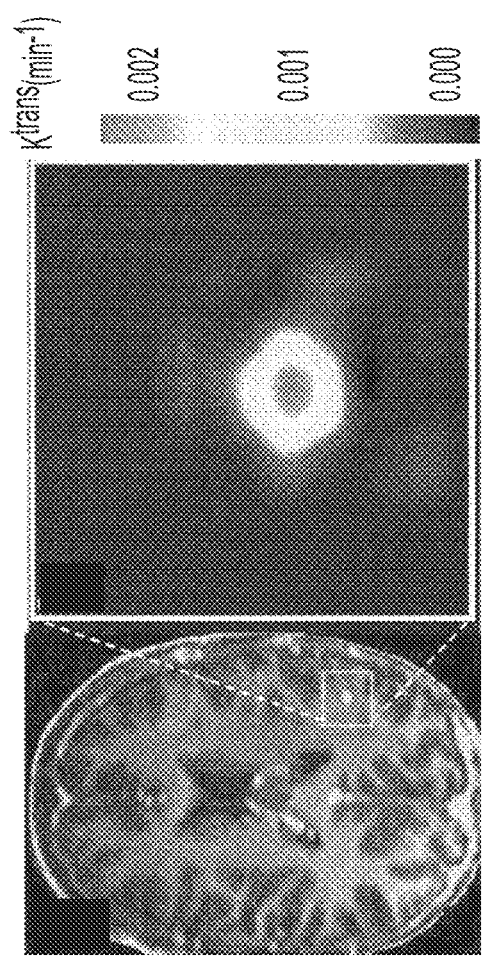
FIG. 10 shows an example axial post-contrast agent (CA) $T_1$-weighted image from a patient with an enhancing MS lesion and zoomed lesion $K^{trans}$ map.

FIG. 10 shows an axial post-CA T$_1$-weighted image (a) from a patient with an enhancing MS lesion (yellow rectangle) and zoomed lesion $K^{trans}$ map (b). FIG. 10b shows an inset zoomed $K^{trans}$ map of the yellow rectangle enclosing an MS lesion in an axial brain image slice (10a). This is a 7 T DCE-MRI study of a different subject, with an active lesion, using GdHD-DO3A. The maximum $K^{trans}$ in the lesion center has risen above $2 \times 10^{-3}$ min$^{-1}$, two orders of magnitude greater than in the normal BBB. This is an SSP $K^{trans}$ map. In general, the larger the $K^{trans}$ value, the greater its underestimation by the tracer paradigm. Since the angiogenic microvessels of malignant tumors have larger intrinsic $K^{trans}$ values than those of benign tumors, the use of shutter-speed paradigm DCE-MRI makes it possible to contemplate eliminating most, if not all, unnecessary biopsies (i.e., those that find no malignancy) in breast cancer. These comprise ~70% of all breast biopsies. The $K^{trans}$ values of malignant tumors are systematically suppressed by the tracer paradigm.

Thus, active MS lesions exhibit significantly increased $K^{trans}$ values, and these remain elevated above NWM values at least six months after maximum enhancement. The chronic FIG. 10 lesions are no longer "active," but their $K^{trans}$ values are still ten times normal. As stated above, $K^{trans} \approx P_{CA}S$, where $P_{CA}$ is the endothelial CA permeability coefficient and S is the total blood vessel surface area per unit mass of tissue. Since the $v_b$ quantity is decreased in the FIG. 10 MS lesions (10b), the S quantity must be as well. Thus, $P_{CA}$ must be significantly increased. There is little doubt that CA employs the paracellular pathway (FIG. 1a) for capillary extravasation: the endothelial cell junctions must open somewhat in an MS lesion. The paracellular pathway must also constitute a component of the passive contribution to water permeability, $P_W$(passive). [In tissues without tight junctions, $\tau_b$ values are smaller; <100 ms in muscle. However, this could be due to greater NKA activity.] Thus, it is highly likely that, in an MS lesion, $P_W$(passive) is increased; however the lesion overall $P_W$ is decreased [$\tau_b$ is increased]. Therefore, the conclusion is that $P_W$(active) is significantly decreased in an MS lesion.

Cerebral $\tau_b$ Values in Glioblastoma multiforme (GBM) Tumors.

The MS interpretation is corroborated by independent studies of human patients suffering from GBM, a serious and deadly disease. For these, the intravascular, coated superparamagnetic iron oxide nanoparticle CA Ferumoxytol is used [S Gahramanov, A M Raslan, L I Muldoon, B E Hamilton, W D Rooney, C G Varallyay, J M Njus, M Haluska, E A Neuwelt. "Potential for Differentiation of Pseudoprogression From True Tumor Progression With Dynamic Susceptibility-Weighted Contrast-Enhanced Magnetic Resonance Imaging Using Ferumoxytol vs Gadoteridol: A Pilot Study," *Int J Radiat Oncol Biol Phys.* 79, 514-23 (2011)]. This agent has a molecular mass of 750,000 Da (103 times that of GdHPDO3A; 588 Da). Its $K^{trans}$ in normal and normal-appearing brain tissue is ~$10^{-8}$ min$^{-1}$. During the first pass, it remains intravascular even in very advanced GBM tumors with extremely permeable capillaries, data very much like those of FIG. 2 is obtained, and the same analysis as for the MS-NAGM above can be made. Parameter values, averaged over six patients, in four tissue ROIs were determined: NA-frontal WM, NA-thalamus, NA-putamen, and tumor. The results are given in Table 1. The $\tau_b$ value is over an order-of-magnitude larger in tumor (T) tissue: there is a 92% decrease in tumor $\tau_b^{-1}$ ($k_{po}$) relative to putamen (P). If the transendothelial water permeability coefficients were equal [$P_W$(T)=$P_W$(P)], then $r_T$=13 $r_p$ ($r_T$ and $r_p$ are the mean capillary radii in tumor and putamen tissue, respectively). It is even more unlikely than in the MS-NAGM tissue that capillaries would dilate more than an order-of-magnitude, in the tumor tissue.

With the same assumptions as above, the ratio $\{v_b(P)/v_b(T)\}^{1/2} = \{\rho_P'/\rho_T'\}^{1/2}(r_P/r_T)$. Unlike the MS lesions (Table 1), however, the tumor $v_b(T)$, 0.046, is increased over normal-appearing tissue, $v_b(P)$=0.012. [Thus demonstrating that $\tau_b$ is indeed independent of $v_b$.] This gives $\{v_b(P)/v_b(T)\}^{1/2}$=0.51. Though extremely unlikely, if $r_T$ was actually 13 $r_p$, then $\rho_{T'}$=0.023 $\rho_p'$: as in the MS lesions, the tumor capillary density would have to be <3% of that of normal brain also just as unreasonable. An unchanged $P_W$ value is incompatible with both the $\tau_b$ and $v_b$ changes. If $r_T$=$r_p$, then $\rho_T'$=3.8 $\rho_p'$, capillary density is increased almost four-fold in the tumor. This may be plausible, and explains the $v_b$ ratio. Recall, however, capillary density does not directly affect the intensive $P_W$ value.

If $r_T=r_P$, $P_W(T)=0.078$ $P_W(P)$. Whatever the actual capillary radius change, it seems certain that overall $P_W$ is much decreased in the tumor. However, $P_{CA}S$ ($K^{trans}$) is highly increased (four orders-of-magnitude) in GBM tumors: mostly due to the $P_{CA}$ factor, since the $v_b$ increase is less than 10. Once again, this points to the almost inescapable conclusion that $P_W$(active) is very much decreased in the brain pathology.

Finally, equilibrium mass action demands: $T_{exv}=\tau_b((1-v_b)/v_b)$; where $\tau_{exv}$ T is the mean extravascular water molecule lifetime. Combining the $v_b$ and $\tau_b$ values from Table 1, yields $\tau_{exv}$ values of 24 s and 13 s for WM and GM, respectively. These are comparable to the first-order lifetime, ~45 s, calculated from the observed ~31 s $t_{1/2}$ for brain parenchyma $^{15}OH_2$ intravasation. As detailed above, this 2SX expression does not require the assumption that parenchymal water is "well-mixed," only that its MR systems are in their FXL conditions ($\tau_{exv}$ is a complicated function of water populations and lifetimes $\tau_i''$, $\tau_o$, $\tau_i$, $\tau_i'$, etc.; FIG. 1).

These results permit calculation of the equilibrium water efflux from brain capillaries. In a 1 µL high-resolution MRI voxel, the average capillary length and radius are estimated as 2 mm and 2.6 respectively (see above). For a cylindrical shape, this gives a mean capillary volume of 42.5 µL. Taking the water concentration to be 50 M, this yields 1.3×1015 $H_2O$ molecules/capillary. For a typical $\tau_b$ of 0.4 s, $\tau_b^{-1}$ ($k_{po}$) is 2.5 $s^{-1}$. This gives the equilibrium water efflux=[1.3× 1015×2.5]=3.2×1015 $H_2O$ molecules/capillary/s (and, of course, an equal influx). This phenomenon is dominated by transcellular pathways (FIG. 1b-1d). This can be seen from the following calculation.

When they extravasate, CA molecules surely use the paracellular pathway (FIG. 1a). A typical maximum plasma CA concentration is 3 mM. The blood $[CA_b]_{max}=(1 h) [CA_p]_{max}$. For a hematocrit (h) of 0.4, this yields $[CA_b]_{max}=0.6\times3=1.8$ mM. Thus at maximum, there are $1.8\times10^{-3}\times42.5\times10^{-12}=4.6\times10^{10}$ CA molecules/capillary. The first-order rate constant for CA extravasation ($k_{pe}$) is $K^{trans}/v_p$. Taking a large $k^{trans}$ value, 0.1 $min^{-1}$, say for a GBM tumor capillary, and a $v_p=[(1-h)v_b=0.6\times0.03]$ of 0.02; $k_{pe}=8.3\times10-2$ $s^{-1}$. This gives a maximum efflux=[4.6× $10^{10}\times8.3\times10^{-2}$]=3.8×10$^9$ CA molecules/capillary/s. Thus the minimal ($H_2O$ efflux/CA efflux) ratio is $8.4\times10^5$. Even if 28,000 $H_2O$ molecules accompanied each CA molecule ($[H_2O]/[CA_b]_{max}$) through the paracellular tight junction pore, there would be 840,000 $H_2O$ molecules exiting by transcellular pathways at the same time. And this would be true for only very leaky capillaries.

Thus, for the normal brain ($K^{trans}$~$10^{-5}$ $min^{-1}$) by far the vast majority of capillary water efflux occurs via one or more transcellular pathways. Here the inventors herein report evidence suggesting that active water cycling processes dominate these. This is visualized as a cascade of $\tau_i$ changes for cells within the gliovascular unit (FIG. 1d). The inventors herein have recently reported similar evidence in the heterogeneity, and response to therapy, of cellular $\tau_i$ values within human breast tumors in vivo. It has been shown that $\tau_i$ is sensitive to the $ATP_i$ and $K_o^+$ substrates for, and specific inhibitors of, the driving ATPase transporters. Thus, it is possible that $\tau_b$ reflects on-going gliovascular unit metabolic activity, particularly Na$^+$/K$^+$ATPase activity: the smaller $\tau_b$ the greater NKA activity, and vice versa.

In this light, it is particularly interesting to observe that $\tau_b$ is increased above normal throughout the normal-appearing MS brain (Table 1). This may be an example of biological insight into a pathology from high-resolution metabolic neuroimaging. Multiple sclerosis is as an immune-system mediated brain, optic nerve, and spinal cord inflammatory pathology. The primary disease process is thought to be a T-cell mediated autoimmune attack directed against myelin, the fatty substance insulating nerve fibers that increases conduction velocity. The pathological hallmark of MS is the demyelinated lesion, recognized for more than 170 years [A Compston, "The 150th anniversary of the first depiction of the lesions of multiple sclerosis," *J Neurol Neurosurg Psychiatry* 51: 1249-1252 (1988)]. The disease cause is unknown, and although several disease modifying therapies have been developed, there is no cure. A clinically definite diagnosis requires clear evidence that disease be disseminated in time and space. This can be demonstrated by exacerbations affecting different sensory or motor areas at distinctly different times, or combined with MRI evidence demonstrating CNS lesions of varying age in different regions. Individuals that present with an initial neurological symptom(s) suggestive of MS are classified as having a clinically isolated syndrome (CIS). CIS subjects with multiple CNS lesions are at high risk for conversion to clinically definite MS within 3 years. There are four principal MS disease subtypes; relapsing-remitting MS (RRMS), secondary-progressing MS (SPMS), primary progressive (PPMS), and relapsing progressive MS (RPMS). By far, the most common disease subtype is RRMS which accounts for about 85% of all new diagnoses. Within 10 years about 50% of those diagnosed with RRMS will transition to SPMS.

While MS has long been considered a WM disease, emerging data suggest that GM may be an early, or even the initial, disease target. Neurodegeneration, manifest as GM atrophy, is detected with excellent sensitivity using anatomical in vivo MRI, and increasingly is recognized as an early MS feature and a significant contributor to clinical disability. Thus, the recently proposed novel concept is that MS disease activity originates in brain regions other than WM, perhaps GM; the "outside-in" hypothesis. In early disease stages, pro-inflammatory cytokines are chronically upregulated in MS brain and these are known to reduce oxygen utilization despite sufficient delivery ["metabolic hypoxia"], mediate mitochondrial function, decrease neurogenesis, and may increase overall risk of neurodegenerative processes. Metabolic deficits of MS-NAGM are more extensive than those in MS-NAWM and include decreased oxygen utilization, altered perfusion, and high-energy phosphate depletion.

Applicants' evidence is that $\tau_b$ is elevated (Table 1) while PCr and ATP are decreased (FIG. 8) in MS-NAGM. Combined with the observation of increased TSC, and likely $Na_i^+$, these strongly suggest decreased Na$^+$/K$^+$ ATPase (NKA) activity in the normal-appearing MS brain. The $\tau_b$ increase may be the earliest metabolic imaging manifestation of this. Since the cell membrane $P_W$'(cell) values of the gliovascular unit cells are dominated by the NKA activity that drives active water cycling, it is likely that there is a $P_W$(active) component of transendothelial permeability comprising the FIG. 1d mechanisms a cascade of decreased active trans-membrane water cycling. This would represent a slow-down of the Magistretti processes (FIG. 1e,f,g), an exciting hypothesis. These results further suggest that the $\tau_b$ increase in MS lesions and GBM tumors is reflecting greatly decreased NKA metabolic activity in the lesion tissue.

Possibly even more exciting, however, is the significantly decreased $\tau_b$ in MS-NAGM of the advanced disease (FIG. 9c). If this is also dominated by the $P_W$(active) component, it means that gliovascular unit NKA activity is increased in advanced MS-NAGM—a strong indication of global metabolic GM involvement—possibly indicating an RRMS to SPMS conversion. Access to a metabolic imaging biomarker for this subtype conversion would be of tremendous benefit. What could be the source of this? There is an interesting recent report that cells intentionally put into a defined apoptotic state exhibit a substantially decreased r, value. Perhaps gliovascular unit cells enter apoptosis in advanced MS disease.

$k_{po}$ Variations are Due to $P_W^\dagger$ Differences.

As noted above, the essential independence of the experimental $k_{po}$ and $v_b$ parameters in the FIG. 4 pixel scatter plot signifies that $k_{po}$ is dominated by capillary wall water permeability. Further, quantitative deductive analyses of concomitant population-averaged $\tau_b^{-1}$ ratios and $v_b$ ratios in normal brain, MS-NA brain, GBM-NA brain, MS lesions, and GBM tumors show that variations in the capillary equilibrium water efflux rate constant [$k_{po}$] are dominated by differences in microvessel wall water permeability [$P_W^\dagger$], not capillary radius. Example analyses are detailed below.

$k_{po}$ Variations and Accompanying $v_b$ Variations.

Consider [conservatively] the MS-induced GM $k_{po}$ change—the smallest in Table 1. We have ⟨ $\tau_b$(NAGM)⟩ $^{-1}$/⟨ $\tau_b$(NGM)⟩ $^{-1}$=2.0 s$^{-1}$/2.5=0.80: the NAGM ⟨ $\tau_b$⟩ $^{-1}$ is reduced by 20% from that in NGM [⟨ $k_{po}$⟩ is reduced by 31%]. From the fundamental theoretical relationship, ⟨ $\tau_b$(NAGM)⟩ $^{-1}$/⟨ $\tau_b$(NGM)⟩ $^{-1}$={$P_W^\dagger$(NAGM)/$P_W^\dagger$(NGM)}($r_{NGM}/r_{NAGM}$): where $r_{NGM}$ and $r_{NAGM}$ are the mean capillary radii in NGM and NAGM tissues, respectively. [Capillaries dominate vascular volume in most voxels (Gesztelyi G, Finnegan W, DeMaro J A, Wang J-Y, Chen J-L, Fenstermacher J. Parenchymal microvascular systems and cerebral atrophy in spontaneously hypertensive rats. Brain Res. 1993; 611: 249-257; Hutchinson E B, Stefanovic B, Koretsky A P, Silva A C. Spatial flow-volume dissociation of the cerebral microcirculatory response to mild hypercapnia. Neuroimage 2006; 32: 520-530.] Thus, the experimental relationship {$P_W^\dagger$(NAGM)/$P_W^\dagger$(NGM)}($r_{NGM}/r_{NAGM}$)=0.80 must be satisfied. There is an infinite number of possibilities: if $r_{NAGM}$=1.25 $r_{NGM}$, $P_W^\dagger$(NAGM)=$P_W^\dagger$(NGM); if $r_{NAGM}$=$r_{NGM}$, $P_W^\dagger$(NAGM)=0.8 $P_W^\dagger$(NGM); etc.

It is extremely difficult, and invasive, to determine individual capillary radii in vivo (38,40,41). However, capillary radius changes, if any, can be estimated from the data. The blood volume fraction $v_b$=(n/$V_T$)V=ρ$^\dagger$V, where (n/$V_T$) is the number of capillaries in the voxel or ROI total volume, the capillary number density, p$^\dagger$ [hundreds/μL (81)], and V is the mean individual capillary volume. Assuming cylindrical capillaries, r~$V^{1/2}$ and the ratio {$v_b$(NGM)/$v_b$(NAGM)}$^{1/2}$={ρ$^\dagger_{NGM}$/ρ$^\dagger_{NAGM}$}$^{1/2}$($r_{NGM}/r_{NAGM}$) Taking $v_b$(NGM) as 0.031, and $v_b$(NAGM) as 0.045 [Table 1] gives {$v_b$(NGM)/$v_b$(NAGM)}$^{1/2}$=0.83.

The solid red curve in FIG. 7 is the trace of all points that simultaneously satisfy the experimental {$P_W^\dagger$(NAGM)/$P_W^\dagger$(NGM)}($r_{NGM}/r_{NAGM}$)=0.80 and {ρ$^\dagger_{NGM}$/ρ$^\dagger_{NAGM}$}$^{1/2}$($r_{NGM}/r_{NAGM}$)=0.83 relationships [from the population- and ROI-averaged Table 1 biomarker values], in a 3D space of tissue microvascular properties. The axes are: $P_W^\dagger$[NGM]/$P_W^\dagger$[NAGM] (vertical), $r_{NGM}^{-1}/r_{NAGM}^{-1}$ (Inverse Capillary Radius Ratio,=$r_{NAGM}/r_{NGM}$), and ρ$^\dagger_{NAGM}$/ρ$^\dagger_{NGM}$ (Capillary Density Ratio). This is very informative. The dot-dashed red projection does not pass through the $r_{NGM}$=$r_{NAGM}$, ρ$^\dagger_{NGM}$=ρ$^\dagger_{NAGM}$ point. The experimental data are incompatible with the mean capillary radius and density simultaneously remaining invariant from NGM to NAGM. The brain literature generally indicates it more likely that chronic $v_b$ differences are due to capillary density [ρ$^\dagger$] differences than to capillary dilation or constriction [r changes]. [Even in an acute hypercapnic perturbation, the microvascular radii for the dominant capillary volume fraction remain unchanged (Hutchinson E B, Stefanovic B, Koretsky A P, Silva A C. Spatial flow-volume dissociation of the cerebral microcirculatory response to mild hypercapnia. Neuroimage 2006; 32: 520-530). The very smallest capillaries, normally effectively occluded, are opened during the hypercapnia there is some "recruitment"—but in most capillaries there is a blood velocity increase.] When the (solid) red curve passes through $r_{NAGM}$=$r_{NGM}$ (black point), the other coordinates are ρ$^\dagger_{NAGM}$=1.44 ρ$^\dagger_{NGM}$ and $P_W^\dagger$[NGM]=1.25 $P_W^\dagger$[NAGM] (dashed black lines). A conservatively large area for $r_{NAGM}$ from 0.75 $r_{NGM}$ to 1.25 $r_{NGM}$ is shaded gray in the bottom FIG. 7 plane. Over this area, the red curve ρ$^\dagger_{NAGM}$ coordinates range from 2.56 ρ$^\dagger_{NGM}$ to 0.92 ρ$^\dagger_{NGM}$, and the $P_W^\dagger$[NGM] coordinates range from 1.67 $P_W^\dagger$[NAGM] to 1.0 $P_W^\dagger$[NAGM]. These results clearly indicate that the mean capillary water permeability in MS normal-appearing GM is reduced from its value in normal GM. For equal mean capillary radii, $P_W^\dagger$[NAGM]=0.8 $P_W^\dagger$[NGM], $P_W^\dagger$ is reduced by 20%. Recall that r is the average for a large number of capillaries. Only 100 capillaries/μL means 4000 per 40 μL voxel. The Table 1 ROIs represent 80 to 100 voxels. 100 voxel ROIs in six subjects yield averages over 2,400,000 capillaries. The analogous exercise indicates an even greater $P_W^\dagger$ decrease in MS-NAWM. $k_{po}$ [$\tau_b^{-1}$] is dominated by the $P_W^\dagger$ factor, not the r$^{-1}$-factor.

For the GBM tumor, the same analysis was made, using tissue ROI- and population-averaged parameter values from Table 1. There is a 93% decrease in tumor [T] $k_{po}$ relative to putamen [P]. If the permeability coefficients were equal [$P_W^\dagger$(T)=$P_W^\dagger$(P)], then $r_T$=14 $r_P$ [with $r_T$ and $r_P$ the mean capillary radii in tumor and putamen tissue, respectively]. It is even more unlikely than in the MS-NAGM tissue that capillaries would dilate more than an order-of-magnitude, in the tumor tissue. As above, the ratio {$v_b$(P)/$v_b$(T)}$^{1/2}$={ρ$_P^\dagger$/ρ$_T^\dagger$}$^{1/2}$($r_P/r_T$). Unlike the MS lesions [Table 1], however, the tumor $v_b$(T), 0.046, is increased over normal-appearing tissue, $v_b$(P)=0.012. [This reinforces that $k_{po}$ is indeed independent of $v_b$. It is decreased in MS lesions and in GBM tumors, though $v_b$ is decreased in the former and increased in the latter.] This gives {$v_b$(P)/$v_b$(T)}$^{1/2}$=0.51. Though extremely unlikely, if $r_T$ was actually 14 $r_P$, then ρ$_T^\dagger$=0.020 ρ$_P^\dagger$: the tumor capillary density would be <3% of that of normal brain even more unreasonable. An unchanged $P_W^\dagger$ value is incompatible with both the $k_{po}$ and $v_b$ changes. If $r_T$=$r_P$, then ρ$_T^\dagger$=3.8 ρ$_P^\dagger$, capillary density is increased almost four-fold in the tumor. This is plausible, and explains the $v_b$ ratio. [However, capillary density does not affect the supra-intensive $P_W^\dagger$ value.] If $r_T$=$r_P$, $P_W^\dagger$(T)=0.072 $P_W^\dagger$(P). Whatever the actual capillary radius change, if any, it seems certain that overall $P_W^\dagger$ is much decreased in the tumor.

Figure 11:
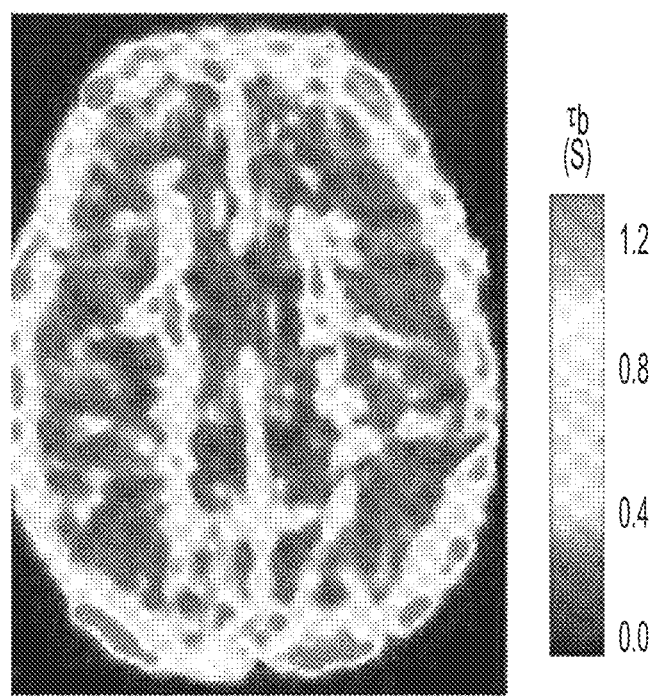
FIG. 11 shows an example $\tau_b$ map for a 52 y F advanced RRMS subject.

Briefly, the following relationships are used: $k_{po}$(A)/$k_{po}$(B)=[$P_W^\dagger$(A)/$P_W^\dagger$(B)][$r_B/r_A$], and [$v_b$(B)/$v_b$(A)]$^{1/2}$=[ρ$_B^\dagger$/ρ$_A^\dagger$]$^{1/2}$[$r_B/r_A$], for ROIs A and B. For example, for A=NAGM and B=NGM we plot in 3D capillary property space the trace of all points that simultaneously satisfy the experimental population-averaged $k_{po}$(A)/$k_{po}$(B) and [$v_b$(B)/$v_b$(A)]$^{1/2}$ ratios [FIG. 11]. The experimental data are incompatible with the mean capillary radius and density simultaneously remaining invariant from NGM to NAGM. Now, the brain literature generally indicates it more likely that chronic $v_b$ differences are due to capillary density [ρ$^\dagger$] differences than to capillary dilation or constriction [r changes] (Itoh Y, Suzuki N. Control of brain capillary blood flow. J. Cereb. Blood Flow & Metabol. 2012; 32: 1167-1176;

Gesztelyi G, Finnegan W, DeMaro J A, Wang J-Y, Chen J-L, Fenstermacher J. Parenchymal microvascular systems and cerebral atrophy in spontaneously hypertensive rats. Brain Res. 1993; 611: 249-257; Pawlik G, Rackl A, Bing R J. Quantitative capillary topography and blood flow in the cerebral cortex of cats: An in vivo microscopic study. Brain Res. 1981; 208: 35-58; Hutchinson E B, Stefanovic B, Koretsky A P, Silva A C. Spatial flow-volume dissociation of the cerebral microcirculatory response to mild hypercapnia. Neuroimage 2006; 32: 520-530). [Even in an acute hypercapnic perturbation, the microvascular radii for the dominant capillary volume fraction remain unchanged. The very smallest capillaries, normally effectively occluded, are opened during the hypercapnia there is some "recruitment" but in most capillaries there is a blood velocity increase.] Therefore, the FIG. 2A results clearly indicate that the mean capillary water permeability in MS normal-appearing GM is reduced from its value in normal GM [the NGM NAGM transition]. For equal mean capillary radii, $P_W^{\dagger}$[NAGM]=0.8 $P_W^{\dagger}$[NGM], $P_W^{\dagger}$ is reduced by 20%. Recall that r is the average for a large number of capillaries. Only 100 capillaries/µL means 4000 per 40 µL voxel. The Table 1 ROIs represent 80 to 100 voxels. 100 voxel ROIs in six subjects yield averages over 2,400,000 capillaries.

Capillary Water Exchange is Dominated by Trans-Cellular Pathways.

There are many possible pathways water molecules can use for capillary egress and ingress. FIG. 1 summarizes these. It depicts: a) para-cellular water passage through endothelial tight junctions [endothelial cells are colored gray], b) simple, trans-cellular water diffusion across cell membrane lipid bilayers, and c) trans-cellular transport through membrane aquaporin protein water channels and/or leakage through membrane transporters. The [6d] trans-cellular process will be elaborated below.

The facts that, in MS lesions and GBM tumors, $P_W^{\dagger}$ decreases while $P_{CA}^{\dagger}$ increases mean that water and CA molecules exchange via different pathways. CA molecules are universally thought to employ the para[endothelial]cellular pathway [FIG. 1a], and it was previously thought that this would be a major mechanism for water as well. However, below $k_{po}$ is compared with $k_{pe}$ [for CA extravasation] to show that, for the normal brain, by far the vast majority [>95%] of capillary water efflux [and influx] occurs via one or more trans-cellular processes [FIG. 1b-1d].

Calculation of Capillary Trans-Cellular Water Flux.

The significance of decreased MS lesion $k_{po}$—decreased trans-endothelial water exchange—was pursued. Consider lesion $K^{trans}$ values. The biomarker $K^{trans} \approx P_{CA}^{\dagger}S$, where $P_{CA}^{\dagger}$ is the endothelial CA permeability coefficient (Li X, Springer C S, Jerosch-Herold M. First-pass dynamic contrast-enhanced MRI with extravasating contrast reagent: Evidence for human myocardial capillary recruitment in adenosine-induced hyperemia. NMR Biomed. 2009; 22: 148 157). The DCE-MRI enhancement of MS lesions is transient during disease progression, increasing and decreasing with time-constants of months, making them hard to "catch" (see Njus J M, Li X, Springer C S, Taylor M, Greisel T, Telang F W, Coyle P K, Rooney W D. Changes in blood-brain barrier permeability and blood volume during MS lesion development and evolution. Proceedings of the 16th Annual Meeting ISMRM, Toronto, Ontario, Canada, 2008; 3431; Njus J M, Li X, Springer C S, Taylor M, Telang F W, Coyle P K, Rooney W D. DCE-MRI Ktrans mapping of MS lesion evolution in individuals. Proceedings of the 16th Annual Meeting ISMRM, Toronto, Ontario, Canada, 2008; 3434). When measurable, however, the $K^{trans}$ values exhibit intra-lesion heterogeneity, and can reach magnitudes over $10^{-2}$ min$^{-1}$. Thus, active MS lesions exhibit significantly increased $K^{trans}$ values, and these remain elevated above NWM values [$10^{-5}$ min$^{-1}$] for at least six months after maximum enhancement. Though the chronic FIG. 5 lesions are no longer "active" in the clinical sense, their $K^{trans}$ values are still ten times normal. Since $v_b$ is decreased in the FIG. 5 MS lesions, the S quantity must be as well. Thus, $P_{CA}^{\dagger}$ must be significantly increased. There is little doubt that CA employs the para[endothelial]cellular pathway [FIG. 1a] for capillary extravasation: the endothelial cell junctions must open somewhat in an MS lesion. The para-cellular pathway must also constitute a component of the passive water permeability, $P_W^{\dagger}$(passive), contribution. Thus, it is highly likely that, in an MS lesion, $P_W^{\dagger}$(passive) is increased. But, it was seen that the lesion overall $P_W^{\dagger}$ is decreased [$k_{po}$ is decreased]. The conclusion is that $P_W^{\dagger}$(active) is significantly decreased in an MS lesion.

Also, for monomeric Gd(III) chelate CAs, $P_{CA}^{\dagger}S$ [$K^{trans}$] is greatly increased [four orders-of-magnitude] in GBM tumors [see FIG. 6, center]: mostly due to the $P_{CA}^{\dagger}$ factor [since the $v_b$ increase is less than one order-of-magnitude]. There is little doubt this is due to widened para[endothelial] cellular pores. Thus, para-cellular water extravasation [a $P_W^{\dagger}$(passive) pathway] must also increase. But this would make $k_{po}$ increase. Once again, we are left with the essentially inescapable conclusion that $P_W^{\dagger}$(active) is very much decreased in the brain pathology.

Previously, the equilibrium brain capillary water efflux in 1 µL tissue was calculated for an average capillary length and radius of 2 mm and 2.6 µm, respectively. For a cylinder, this gives a mean capillary volume [V] of 42.5 pL. A 50 M [H$_2$O] yields $1.3 \times 10^{15}$ H$_2$O molecules/capillary. For NGM, $k_{po}$ is 2.9 s$^{-1}$ [Table 1]. This gives the equilibrium water efflux=[$1.3 \times 10^{15} \times 2.9$]=$3.8 \times 10^{15}$ H$_2$O molecules/s/capillary [and, of course, an equal influx]. Extravasating contrast agent molecules surely use the para-cellular pathway [1a; for H$_2$O]. A typical maximum plasma CA concentration is 3 mM (Landis C S, Li X, Telang F W, Coderre J A, Micca P L, Rooney W D, Latour L L, Vetek G, Palyka I, Springer C S. Determination of the MRI contrast agent concentration time course in vivo following bolus injection: Effect of equilibrium transcytolemmal water exchange. Magn. Reson. Med. 2000; 44: 563-574). The blood [CA$_b$]$_{max}$=(1-h) [CA$_p$]$_{max}$A 0.4 hematocrit (h) yields [CA$_b$]$_{max}$=0.6×3=1.8 mM. Thus at maximum, there are $1.8 \times 10^{-3} \times 42.5 \times 10^{-12} \times 6.0 \times 10^{23} = 4.6 \times 10^{10}$ CA molecules/capillary. The CA extravasation first-order rate constant [$k_{pe}$] is $K^{trans}/v_p$, also supra-intensive. A large $K^{trans}$ value, 0.1 min$^{-1}$, say for a GBM tumor capillary, and $v_p = [(1-h)v_b = 0.6 \times 0.03] = 0.02$, yields $k_{pe} = 8.3 \times 10^{-2}$ s$^{-1}$. This gives a maximum efflux= [$4.6 \times 10^{10} \times 8.3 \times 10^{-2}$]=$3.8 \times 10^{9}$ CA molecules/s/capillary. Thus the minimal [H$_2$O efflux/CA efflux] ratio is 1,000,000. Even if 28,000 H$_2$O molecules accompanied each CA molecule {[H$_2$O]/[CA$_b$]$_{max}$ through the para-cellular tight junction pore (1a), there would be 972,000 H$_2$O molecules simultaneously exiting by trans-cellular pathways [1b-1d]. Only 3% of water employs the para-cellular pathway [4a]; 97% of equilibrium water flux is trans-cellular [1b-1d]. This is for quite leaky capillaries: less permeable vessels would give an even greater trans-cellular percentage. [Though the $K^{trans}$ for head muscle tissue is greater, 0.15 min$^{-1}$ (96), $k_{po}$ may be >10 s$^{-1}$ (Schwarzbauer C, Morrissey S P, Deichmann R, Hillenbrand C, Syha J, Adolf H, Nöth U, Haase A. Quantitative magnetic resonance imaging of capillary water permeability and regional blood volume with an intravascular MR contrast agent. Magn. Reson. Med. 1997; 37: 769

777). Consequently, even in that case <1% of the steady-state water flux is para-cellular [1a].] Thus, for the normal brain [$K^{trans}$~$10^{-5}$ min$^{-1}$] by far the vast majority of capillary water efflux occurs via one or more trans-cellular processes.

Equilibrium Transendothelial Water Exchange is a Metabolically Active Process.

Mechanisms 1b and 1c in FIG. 1 [bilayer diffusion, and passage through trans-membrane aquaporin and/or protein channels, respectively] are passive, i.e., require no energy expenditure. However, comparison of Applicants' results with literature metabolic imaging studies of the same tissues indicates the process measured by $k_{po}$ is metabolically active. This is shown in Table 2 below. In Table 2, the second and third columns repeat the Table 1 $v_b$ and $k_{po}$ entries and places them adjacent to results of pertinent quantitative $^{31}$PMRSI (78: Sammi M K, Berlow Y, Barbara T, Selzer A, Grinstead J, Kim E, Bourdette D, Rooney W. Decreased cellular energetics in multiple sclerosis gray matter: A 7 T phosphorus spectroscopy study," Neurol. 2012; 78: 521.004; 79: Sammi M, Berlow Y, Selzer A, Maloney B, Grinstead J, Kim E, Bourdette D, Rooney W. Decreased gray matter high energy phosphate levels in multiple sclerosis: A 7 Tesla phosphorus spectroscopic imaging study) and $^{23}$NaMRSI (19: Inglese M, Madelin G, Oesingmann N, Babb J S, Wu W, Stoekel B, Herbert J, Johnson G. Brain tissue sodium concentration in multiple sclerosis: A sodium imaging study at 3 Tesla. Brain 2010; 133: 847-857; 80: Ouwerkerk R, Bleich K R, Gillen J S, Pomper M G, Bottomley P A. Tissue sodium concentration in human brain tumors as measured with 23Na MR imaging. Radiology 2003; 227, 529-537) studies. Because of $^{31}$PMRSI spatial resolution limitations, it is important that WM/GM image segmentation be accomplished with co-registered $^1$H$_2$O maps, and then applied to apportion the MRSI measurements. Such results are listed in Table 2. It is clear that $k_{po}$ exhibits a positive correlation with tissue ATP concentration, [ATP$_t$]; comparing NWM to NGM, NWM to NAWM, NGM to NAGM, or NAWM to NAGM. For example, [ATP$_t$] decreases from normal brain in both NAWM [13%] and NAGM [20%]. The phosphocreatine concentration, [PCr$_t$], also decreases [not shown] in rough proportion to [ATP$_t$], consistent with the maintenance of overall ATP/PCr equilibrium. In contrast, $k_{po}$ correlates negatively with tissue sodium concentration, [Na$_t$], which increases in NAWM [39%], NAGM [17%], and GBM tumor [51%]. An [Na$_t$], TSC, increase usually reflects an [Na$_i$] increase. Since there is insignificant extracellular ATP, [ATP$_t$] reflects [ATP$_i$]. Both [ATP$_i$] decrease and [Na$_i$] increase signify compromised metabolism: decreased ATP hydrolysis chemical potential and trans-mural Na$^+$ gradient electrochemical potential, respectively. The brain $k_{po}$ values are correlated with metabolic thermodynamic properties.

TABLE 2

| | SSP DCE-MRI ($^1$H$_2$O) | | $^{31}$PMRSI | $^{23}$NaMRSI | SSP DCE-MRI ($^1$H$_2$O) | $^{31}$PMRSI-MT |
|---|---|---|---|---|---|---|
| | $v_b$ | $k_{po}$ [$\tau_b^{-1}$] (s$^{-1}$) | [ATP$_t$] (mM) | [Na$_t$] (mM) | $k_{po} \cdot v_b$ (s$^{-1}$) | CMR$_{oxphos}$ (pmol(ATP)/s/μL) |
| Healthy Controls | | | | | | |
| NWM | 0.014 | 3.2 | 2.43 | 19$^a$ | 0.045 | 50 |
| NGM | 0.031 | 2.9 | 1.62 | 31$^a$ | 0.090 | 160 |
| NGM/NWM | | | | | 2.0 | 3.2 |
| Relapsing Remitting MS | | | | | | |
| NAWM | 0.019 | 2.2 | 2.11 | 27$^a$ | 0.042 | |
| NAGM | 0.045 | 2.0 | 1.29 | 36$^a$ | 0.090 | |
| lesion | 0.012 | 1.8 | | 35$^a$ | 0.022 | |
| Glioblastoma | | | | | | |
| NA-frontal WM | 0.008 | 2.6 | | ↑3%$^b$ | 0.021 | |
| NA-thalamus | 0.017 | 2.9 | | ↓12%$^b$ | 0.049 | |
| NA-putamen | 0.012 | 2.5 | | | 0.030 | |
| tumor | 0.046 | ≤0.18 | | ↑51%$^b$ | ≤0.008 | |
| References | this work | | 78, 79 | 19, 80 | this work | 17 |

However, $k_{po}$ is a kinetic parameter [of dimension, reciprocal time]. In order to validate a flux measurement, one must compare it with the gold standard flux measurement. Normal homeostatic neuronal cell metabolic rates have been measured with $^{31}$PMRSI-MT, using $^1$H$_2$O segmentation (Zhu X-H, Qiao H, Du F, Xiong Q, Liu X, Zhang X, Ugurbil K, Chen W. Quantitative imaging of energy expenditure in human brain. Neuroimage. 2012; 60: 2107-2117). For NGM, the ATP synthesis [mostly by oxidative phosphorylation, CMR$_{oxphos}$; FIG. 1] flux is 0.16 nmol/s/A, and the consumption rate is the same. The fluxes between ATP and phosphocreatine (PCr) are seven times larger, 1.15 nmol/s/μL in each direction: integrated over the neuron, ATP and PCr are in effective equilibrium. The NGM and NWM CMR$_{oxphos}$ values, 160 and 50 pmol(ATP)/s/μL, respectively, are entered in Table 2, as is the CMR$_{oxphos}$[NGM]/CMR$_{oxphos}$[NWM] ratio, 3.2. By definition, $k_{po}$ is proportional to the H$_2$O flux/capillary and $v_b$ to the number of capillaries per unit tissue volume. Since CMR$_{oxphos}$ is an intensive property [all that is accessible by $^{31}$PMRSI], we must multiply the supra-intensive $k_{po}$ by the intensive $v_b$ in order to compare. Thus, the $k_{po} \bullet v_b$ products and the ($k_{po}v_b$[NGM])/($k_{po}v_b$[NWM]) ratio, 2.0, are displayed in Table 2. The agreement of the flux ratios for these two very different, and independent techniques, $^{31}$PMRSI-MT and DCE-MRI ($^1$H$_2$O), is rather remarkable and strongly suggests $k_{po}$ is proportional to CMR$_{oxphos}$, per capillary.

The Table 2 NGM and NWM [ATP$_t$] and CMR$_{oxphos}$ values exemplify the thermodynamics/kinetics distinction. While the steady-state ATP concentration [and thus free energy] per unit tissue volume is 1.5× greater in NWM than NGM, the oxidative phosphorylation ATP flux in the same unit tissue volume is 3.2× greater in NGM than NWM.

A Neurogliovascular Unit Chain Mechanism.

Table 2 shows that $k_{po}$ is proportional to the ATP consumption flux per capillary [the core of the neurogliovascular unit]. A clue to the mechanism of this is in a recent report on the heterogeneity, and response to therapy, of cellular values within human breast tumors in vivo (Springer C S, Li X, Tudorica L A, Oh K Y, Roy N, Chui S Y-C, Naik A M, Holtorf M L, A. Afzal A, W. D. Rooney W D, Huang W. Intra-tumor mapping of intra-cellular water lifetime: Metabolic images of breast cancer? NMR Biomed. 2014; 27: 760-773). That paper also assembles the evidence from model studies that $\tau_i^{-1}$ is increased by the gene dosage of, and substrates for, the driving cell membrane P-type ATP-ase ion pump, and decreased by specific inhibitors. Cellular $k_{io}$ [$\tau_i^{-1}$] reflects P-type ATP-ase turnover, per cell. FIG. 1d visualizes a cascade [or chain] of $\tau_i$ changes for cells within the neurogliovascular unit. These are $\tau_i$ [neuroglia, pink], $\tau_i'$ [endothelial cells], and $\tau_i''$ [neurons, blue]. In the FIG. 1 cartoon, these active processes are indicated by trans-membrane water cycles [stars, 1d]. The pink cells can be astrocytes, oligodendrocytes, pericytes, etc. Combinations of neurons, glia, and microvessels have been termed "gliovascular units" (Abbot N J, Ronnback L, Hansson E. Astrocyte-endothelial interactions at the blood-brain barrier. Nat. Rev. Neurosci. 2006; 7: 41 53), because of their crucial, exquisite symbiotic metabolic and energetic interactions. The [1d] pathways represent processes driven by NKA turnover, perhaps the most crucial on-going cellular metabolic activity in the brain. These would affect each other by changes in transporter substrate concentrations ["paracrine communication"]. This is plausible because these cells are within synaptic proximities, and have asymmetric transporter distributions. Microjets of water and substrates are continually injected into these confined spaces as transporters turn over. Thus, it is possible that $\tau_b$ in turn reflects on-going neurogliovascular unit metabolic turnover, particularly $Na^+,K^+$ ATP-ase activity: the smaller $\tau_b$ the greater NKA turnover, and vice versa a cascade of altered active trans-membrane water cycling—a $k_{po}$ decrease reflecting $k_{io}$ decreases within the unit. For example, the "Magistretti Mechanism" [FIG. 1e-g] has neuroglia essentially conducting most glycolysis and transferring lactate to neurons for mostly oxidative phosphorylation: the capillary is intimately involved in this intercellular metabolic cooperativity. An increase in $k_{po}$ would reflect a speed-up of Magistretti-type processes [FIG. 1e,f,g], an exciting hypothesis. The increased $k_{po}$ in NWM [FIGS. 3c,4] may reflect increased metabolic activity in common tracts shared by fluctuating resting-state neural circuits. [it is noted that the BOLD effect reflects the coupling of metabolic activity with vascular properties.] The extravascular water lifetime $\tau_{exv}$ r is a complicated function of water populations and lifetimes $\tau_i''$, $\tau_o$, $\tau_i$, $\tau_i'$, etc. [FIG. 1].

Absolute Quantitation.

The results described herein allow calculation of the equilibrium brain capillary water efflux. In 1 µL tissue, the average capillary length and radius were estimated as 2 mm and 2.6 µm, respectively, above. For a cylinder, this gives a mean capillary volume [V] of 42.5 µL. A 50 M [$H_2O$] yields $1.3 \times 10^{15}$ $H_2O$ molecules/capillary. For NGM, $k_{po}$ is 2.9 s$^{-1}$ [Table 1]. This gives the equilibrium water efflux=[$1.3 \times 10^{15} \times 2.9$]=$3.8 \times 10^{15}$ $H_2O$ molecules/s/capillary [and, of course, an equal influx]. Now, consider the homeostatic NGM CMR$_{oxphos}$, 160 pmol(ATP)/s/µL (Zhu X-H, Qiao H, Du F, Xiong Q, Liu X, Zhang X, Ugurbil K, Chen W. Quantitative imaging of energy expenditure in human brain. Neuroimage. 2012; 60: 2107-2117). If 75% is used for NKA turnover, we have 120 pmol(ATP)/s/µL consumption. For 100 capillaries/A, this is 1.2 pmol(ATP)/s/capillary. The NGM water flux estimated above corresponds to 6 nmol ($H_2O$)/s/capillary, and yields $5 \times 10^3$ $H_2O$ molecules cycled per NKA turnover [one ATP molecule consumed]. Some individual water co-transporting membrane symporters have $H_2O$ stoichiometries approaching this order of and there are likely a number of different symporters involved in the neurogliovascular unit chain [FIG. 1d]. Thus, in addition to the remarkable agreement with relative CMR$_{oxphos}$ values in Table 2, it is possible that brain $k_{po}$ values can be interpreted quantitatively. For a 44 µL rat brain ROI in vivo, $k_{io}$ was measured as 1.8 s$^{-1}$ using a very invasive intracerebroventricular CA infusion (Quirk J D, Bretthorst G L, Duong T Q, Snyder A Z, Springer C S, Ackerman J J H, Neil, J J. Equilibrium water exchange between the intra- and extra-cellular spaces of mammalian brain. Magn. Reson. Med. 2003; 50: 493-499). The chain mechanism [FIG. 1d] suggests $k_{po}$ should be similar to $k_{io}$.

Clinical Implications.

Embodiments described herein have many potential clinical applications, examples of which are described below.

Multiple Sclerosis (MS).

The longstanding MS imaging hallmark is the "enhancing" WM lesion. Above it was mentioned that enhancement [with CA] is transient, and not always "caught" in an MRI study. The FIG. 5 late-stage subject is an example. Though her WM lesions are chronic, and large, they were not especially CA-enhancing at the time of acquisition, and their conspicuity in the $R_{1exv}$ map [essentially a $T_1$-w image] is poor. However, if we inspect the $\tau_b$ map [the FIG. 5c inverse] in FIG. 11, the conspicuity is very high. Thus, the prospect for detecting lesions is much greater with a $\tau_b$ map.

Meanwhile, MS understanding is evolving. While long considered a WM disease, emerging data suggest that GM may be an early, or even the initial, disease target (Miron V E, Kuhlmann T, Antel J P. Cells of the oligodendroglial lineage, myelination, and remyelination. Biochim. Biophys. Acta 2011; 1812: 184-193; Popescu B F, Lucchinetti C F. Meningeal and cortical grey matter pathology in multiple sclerosis. BMC Neurol. 2012; 12: 11). A recent concept is that MS disease activity originates in brain regions other than WM, perhaps GM; the "outside-in" hypothesis. In early disease, pro-inflammatory cytokines are chronically upregulated and can reduce oxygen utilization despite sufficient delivery ["metabolic hypoxia"], mediate mitochondrial function, decrease neurogenesis, and may increase overall neurodegeneration risk. Metabolic deficits of MS-NAGM are more extensive than those in MS-NAWM and include decreased oxygen utilization, altered perfusion, and high-energy phosphate depletion.

If MS-NAGM and MS-NAWM NKA turnover is diminished by metabolic hypoxia then, according to our mechanism, the supra-intensive $k_{po}$ would decrease. This is what is demonstrated in Table 2. The results described herein predict this should not be detectable by $^{31}$PMRSI-MT, which can access only the intensive CMR$_{oxphos}$. Table 2 indicates that $k_{po} \bullet v_b$—the CMR$_{oxphos}$ analog—does not decrease in RRMS NAGM or NAWM: the $\rho^\dagger$ increase compensates the $P_W^\dagger$ decrease. By itself, a [$Na_i$] increase would cause NKA turnover to increase. However, a simultaneous [$ATP_i$] decrease in the same cell probably takes precedence. Alternatively, the [$Na_i$] increase observed [Table 2] may be confined to certain cells within the neurogliovascular unit, say neuroglia, that have lower NKA copy numbers, while at the same time, cells with larger NKA copy numbers, say neurons, overwhelm with slower NKA turnover. NKA activity can be regulated in several different ways (Reinhard L, Tidow H, Clausen M J, Nissen P. Na+,K+-ATPase as a docking station: Protein-protein complexes of the Na+,K+-ATPase. Cell Mol. Life. Sci. 2013; 70: 205-222).

Also exciting is the significantly increased MS-NAGM $k_{po}$ in the late-stage disease [FIG. 5c]. If this is borne out in more subjects, it means that neurogliovascular unit NKA activity is increased in advanced MS-NAGM a strong indication of global metabolic GM involvement possibly indicating an RRMS to SPMS conversion. Access to a metabolic imaging biomarker for this stage change would be of tremendous benefit. Inspection of the same map [FIG. 5c] suggests the demyelinated lesions in WM seem to have greatly diminished resting-state metabolic activity. Perhaps the NAGM activity is increased because of the necessity to employ "detour" circuitry. Alternatively, perhaps neurogliovascular unit cells enter apoptosis in advanced MS disease. There is an interesting report that cells intentionally put into a defined apoptotic state exhibit a substantially increased $k_{io}$ (Bailey C, Giles A, Czarnota G J, Stanisz G J. Detection of apoptotic cell death in vitro in the presence of Gd-DTPA-BMA. Magn. Reson. Med. 2009; 62: 46-55).

Glioblastoma Multiforme (GBM) Tumor.

In GBM tumors, $k_{po}$ values <1 s$^{-1}$ [Table 2] suggest that NKA turnover is exceptionally slow. This is consistent with tumor [Na$_t$] being increased 51% over its value in NWM [Table 2]. The findings that $k_{po}$ values in GBM-NA tissue are similar to those in the control brain are also consistent with the fact that tumor-NA tissue [Na$_t$] values differ little from control [Table 2]. A recent qualitative $^{31}$PMRSI investigation of human GBM in vivo suggests that [ATP$_t$] and [PCr$_t$] values are essentially the same in tumor tissue as in control brain (Ha D-H, Choi S, Oh J Y, Yoon S K, Kang M J, Kim K-U. Application of 31P MR spectroscopy to the brain tumors. Korean J. Radiology 2013; 14: 477-486). Also it has been found that, while MR$_{glc}$ is only slightly elevated over adjacent WM in GBM tumor (Krohn K A, Mankoff D A, Muzi M, Link J M, Spence A M. True tracers: Comparing FDG with glucose and FLT with thymidine. Nucl. Med. Biol. 2005; 32: 663-671), there is extensive hypoxia (Rajendran J G, Mankoff D A, O'Sullivan F, Peterson L M, Schwartz D L, Conrad E U, Spence A M, M. Muzi M, Farwell D G, Krohn K A. Hypoxia and glucose metabolism in malignant tumors: Evaluation by [18F]fluoromisonidazole and [18F]fluorodeoxyglucose positron emission tomography. Clin. Cancer Res. 2004; 10: 2245-2252). In this condition, ATP production shifts from oxidative phosphorylation toward glycolysis. Within the neurogliovascular unit, this means that the locus of ATP synthesis shifts from neurons toward neuroglial cells. The consequence of this could be that a decrease in neuronal glucose consumption is slightly overcompensated by an increase in neuroglia, which also have proliferated in the tumor. However, net NKA turnover in the neurogliovascular unit, dominated by neurons, would decrease and consequently neuronal [Na$_t$] would increase. The substantial GBM tumor $k_{po}$ decrease [Table 2] may be a hypoxia signature. Unlike $^{18}$FDG PET or glucoCEST/CESL, the activity we ostensibly measure is catabolically downstream of an oxphos→glycolysis shift. The turnover of NKA is a major end-point of central [intermediary] metabolism. However, the population-averaged value of 6 s for $\tau_b$ in GBM tissue [Table 1] is quite surprisingly large. Perhaps it really reflects just a complete breakdown of the neurogliovascular unit.

Stroke.

The acute and significant cerebral water apparent diffusion coefficient [ADC] drop after an ischemic event is of considerable clinical importance, though the mechanism has remained elusive. An active trans-membrane water cycling decrease may contribute. Consistent with this, the ADC drops by 40% within 15 minutes of direct application of ouabain [a specific NKA inhibitor] to the striatum—before there is significant decrease of the NKA substrate ATP, (Veldhuis W B, van der Stelt M, Delmas F, Gillet B, Veldink G A, Vliegenthart J F G, Nicolay K, Bår P R. In vivo excitotoxicity induced by ouabain, a Na+/K+-ATPase inhibitor. J. Cerebr. Blood Flow & Metabol. 2003; 23: 62-74).

High-Resolution Metabolic MRI of Myocardium in Vivo.

Paramagnetic Gd(III) chelate contrast agents (CAs) have been used in myocardial MRI for some time. This began as what is now referred to as DCE-MRI. Generally, DCE-MRI involves the acquisition of serial high-resolution $T_1$-weighted $^1$H$_2$O MR images before, during, and after the bolus injection of one of several CAs approved for human use. Normal myocardial tissue shows a very rapid image intensity enhancement The application of DCE-MRI to cancer has flourished dramatically. However, after it was learned that damaged myocardial tissue has a significantly delayed enhancement, the cardiovascular MR community has very deliberately moved away from early DCE-MRI enhancement—even to the point of not acquiring many serial images, often only one before and one 15 to 30 minutes after the CA injection. In fact, elegant CA administration protocols have been devised involving a bolus followed by an infusion. The aim is to achieve a CA steady-state, in which the blood plasma and myocardial interstitium CA concentrations ([CA$_p$] and [CA$_o$], respectively) are constant during the post-CA acquisition. It is thought this allows a good measure of the (interstitial) extracellular myocardial volume fraction, ECV. The latter is an outstanding outcome predictor for many different myocardial pathologies.

In extensive studies of tumor DCE-MRI, Applicants have learned that the temporal [CA$_o$] variation (driven by varying the plasma concentration of the contrast agent (CA); [CA$_p$]) that follows a bolus contrast injection is crucial for correct tissue characterization. This is because the kinetics of equilibrium inter-compartmental water molecule exchange is inherently encoded in DCE-MRI time-course data. Straightforward application of the tracer pharmacokinetic paradigm carries the inherent assumption that these kinetics are effectively infinitely fast. This incorrect postulate causes systematic errors in the values of the classic pharmacokinetic parameters ECV and K$^{trans}$., mostly a measure of the CA extravasation rate. There is an indication that the incorrect tracer ECV value does not agree as well with myocardial pathology assessed by histology. Applicants' novel shutter-speed pharmacokinetic paradigm (SSP) accounts for the water exchange kinetics, characterized by the mean intracellular water molecule lifetime. The [CA$_o$] variation allows measurement because it varies the MR shutter-speed. Thus, in addition to its extracellular volume (ECV) and K$^{trans}$ errors, the tracer paradigm denies access to the water exchange kinetics themselves because it assumes that is effectively zero. However, Applicants have recently learned that is a biomarker measuring cellular metabolic activity. It is dominated by the on-going turnover rate constant of one of nature's most important and ubiquitous enzymes, the Na$^+$K$^+$ATPase (NKA) cell membrane ion transporter. This is a very significant discovery because this has never been possible. It has been estimated that most cells expend nearly ⅓ of their total energy maintaining ion gradients across the cell membrane; an even higher percentage of energy use is observed for excitable cells. Therefore measures are likely to provide strong surrogate from regional metabolic activity. High-resolution maps are metabolic activity maps.

Figure 12:
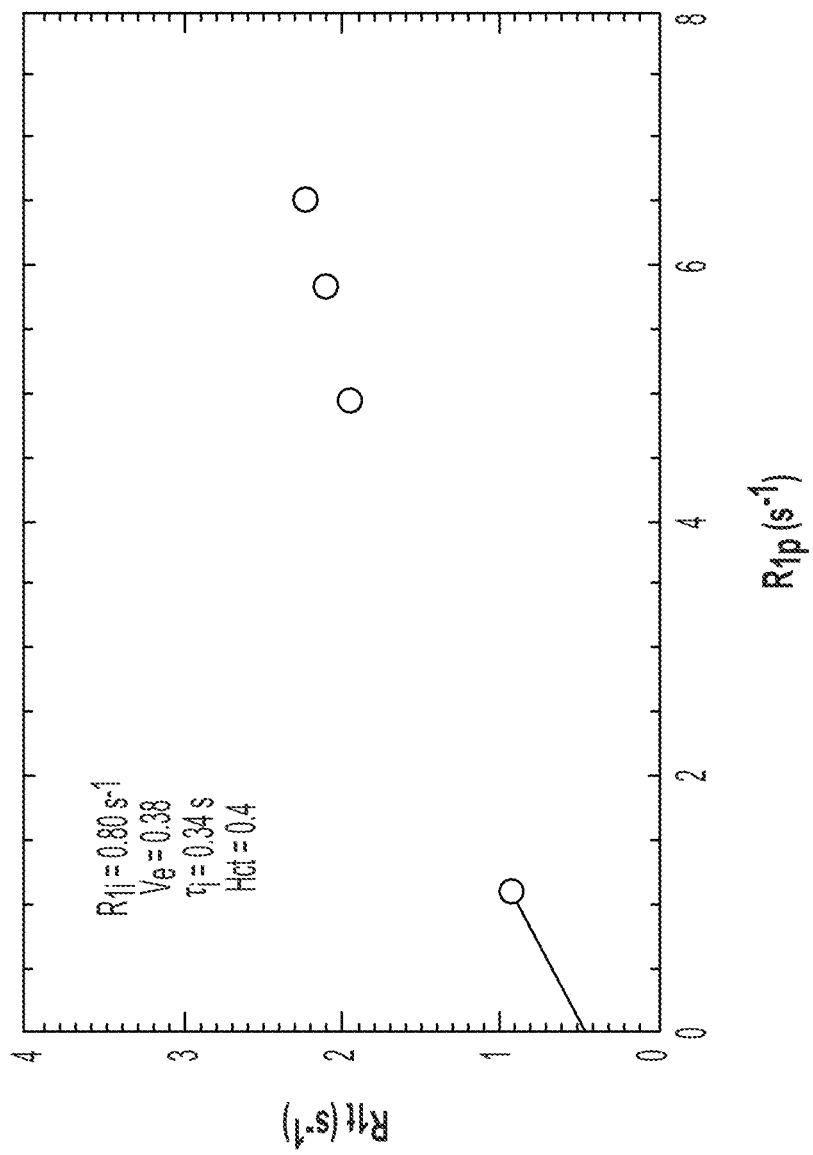
FIG. 12 shows an example SSP approach fitting of DCE-MRI data collected from a human heart.

Cardiovascular disease is the leading cause of death in the United States. The diagnosis and treatment of cardiovascular disease could benefit substantially from the SSP DCE-MRI approach, which has the capability to assess regional cardiac metabolism using the $\tau_i$, biomarker as described above. Applicants demonstrate feasibility of this approach using human in vivo cardiac DCE-MRI data which has been fitted using the SSP approach. In particular, FIG. 12 shows an SSP approach fitting of DCE-MRI data collected from human heart. The circles represent data collected at four times: one prior to CA administration (the first circle representing $R_{1t}$ and $R_{1p}$ both at their smallest values prior to CA injection) and three post-CA administration. $R_{1t}$ is the cardiac tissue $^1H_2O$ $R_1$, value, and $R_{1p}$ is the blood plasma $^1H_2O$ $R_1$ value calculated for a hematocrit (Hct) of 0.4. The solid line represents the best SSP model fitting to the data with parameters shown in inset.

This data was acquired from a normal heart. Applicants expect substantially elevated values from metabolically impaired myocardium as occurs in ischemic heart disease. This approach has important applications to non-invasively assess cardiac metabolism in the human myocardium in vivo. Applicants will employ an adaptive SSP data analysis. Successive fittings of the wash-out portion of the DCE time-course (more sensitive to $\tau_i$) and the uptake portion (more sensitive to $K^{trans}$) will be iterated to rapid convergence [ECV contributes to both portions]. High-resolution ECV, $\tau_i$, and $K^{trans}$ maps will be produced (similar to the $\tau_b$ map shown in the figures). The $K^{trans}$ biomarker has a four order-of-magnitude dynamic range to myocardial tissue insult. Embodiments are contemplated to apply modern SSP DCE-MRI to the human myocardium in vivo and employ an adaptive SSP data analysis. Successive fittings of the wash-out portion of the DCE time-course (which is more sensitive to $\tau_i$) and the uptake portion (which is more sensitive to $K^{trans}$) may be iterated to rapid convergence [ECV contributes to both portions]. High-resolution ECV, $\tau_i$, and $K^{trans}$ maps may be produced. The $K^{trans}$ biomarker has a four order-of-magnitude dynamic range to myocardial tissue insult.

In this way, the SSP may be applied to extract mean intracellular water lifetimes from human myocardium and compare values between healthy and diseased myocardium. The hypothesis that will be tested is that intracellular water lifetimes are longer in diseased myocardium than healthy tissue. Such an approach may provide an adaptive cardiac DCE-MRI acquisition approach that will support the precise determination of pharmacokinetic parameters $K^{trans}$, $v_e$, and $\tau_i$, used to measure and compare PK parameters between healthy controls (n=10) and individuals with ischemic heart disease (n=10).

The examples described herein have demonstrated a new acquisition pulse sequence that incorporates the "multiband" approach (Breuer F A, Blaimer M, Heidemann R M, Mueller M F, Griswold M A, Jakob P M. Controlled aliasing in parallel imaging results in higher acceleration (CAIPIR-INHA) for multi-slice imaging. Magn. Reson. Med. 2005; 53: 684-691) and yields full brain coverage with nominal voxel volume less than half that in FIGS. 3, 5, and 11.

The existence of, or dominance of, an active cell membrane $k_{io}$ has implications for many different types of in vivo MR experiments. In the metaboCEST experiment, The RF-induced $^1H_2O$ intensity change depends on two factors: 1) the metabolite concentration, and 2) the probability per unit time of a water molecule encountering the metabolite molecule. Some water must cross a cell membrane to gain this access, and this transport can contribute to the metaboCEST signal. In glucoCEST, for example, the contribution from intracellular glucose is "very small to negligible" (Chan K W Y, McMahon M T, Kato Y, Liu G, Bulte J W M, Bhujwalla Z M, Artemov D, van Zijl P C M. Natural D glucose as a biodegradable MRI contrast agent for detecting cancer. Magn. Reson. Med. 2012; 68: 1764-1773). But, ~80% of water is intracellular. An aim of glucoCEST is to determine relative glucose concentrations (Walker-Samuel S, Ramasawmy R, Torrealdea F, Rega M, Rajkumar V, Johnson S P, Richardson S, Gongalves M, Parkes H G, Arstad E, Thomas D L, Pedley R B, Lythgoe M F, Golay X. In vivo imaging of glucose uptake and metabolism in tumors. Nat. Med. 2013; 19: 1067-1072). Since $k_{io}$ likely changes during a glucose challenge, the probability of intra- and extracellular $H_2O$ molecules crossing the membrane changes. The fact that this would also alter the temporal probability of water encountering glucose could affect the interpretation of glucoCEST changes. This phenomenon may have already been manifest in the glucoCESL experiment (Jin T, Mehrens H, Hendrich Kans., Kim S-G. Mapping brain glucose uptake with chemical exchange-sensitive spin-lock magnetic resonance imaging. J. Cereb. Blood Flow & Metabol. 2014; 34: 1402-1410).

It is possible that water movement in living tissue is dominated by active trans-membrane water cycling. Significant shutter-speed effects are very common in cancer MRI (Springer C S, Li X, Tudorica L A, Oh K Y, Roy N, Chui S Y-C, Naik A M, Holtorf M L, A. Afzal A, W. D. Rooney W D, Huang W. Intra-tumor mapping of intra-cellular water lifetime: Metabolic images of breast cancer? NMR Biomed. 2014; 27: 760-773). [Since the angiogenic microvessels of malignant tumors have larger intrinsic $K^{trans}$ values than those of benign tumors, the use of SSP DCE-MRI makes it possible to contemplate eliminating most, if not all, unnecessary biopsies (i.e., those that find no malignancy) in breast and prostate cancer. These comprise ~70% of all breast and prostate biopsies. The $K^{trans}$ values of malignant tumors are systematically suppressed by the tracer paradigm.] These effects are now also being found in animal and human myocardium in vivo (Zhang Y, Balschi J A. Water exchange kinetics in the isolated heart correlate with Na+/K+ ATPase activity: Potentially high spatiotemporal resolution in vivo MR access to cellular metabolic activity. Proceedings of the 21st Annual Meeting ISMRM, Salt Lake City, Utah, USA, 2013; 4045; W. D. Rooney, C. S. Broberg, C. S. Springer, Taui, a metabolic imaging biomarker for myocardium. Proceedings of the 22nd Annual Meeting ISMRM, Milan, Italy, 2014; 2460). The NMR shutter-speed concept described herein has broad application.

In some embodiments, the above described methods and processes may be tied to a computing system including one or more computers. In particular, the methods and processes described herein may be implemented as a computer application, computer service, computer API, computer library, and/or other computer program product.

Figure 13:
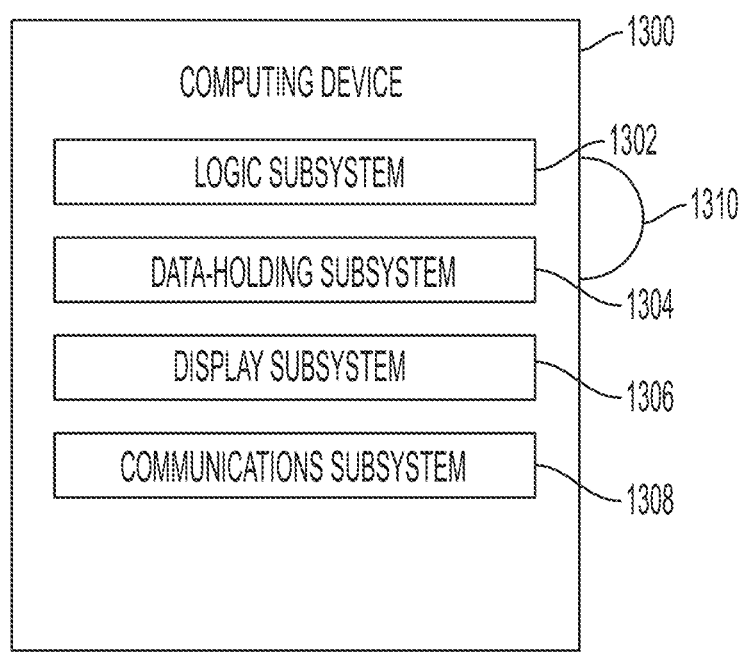
FIG. 13 shows a schematic depiction of a computing device in accordance with various embodiments.

FIG. 13 schematically shows a nonlimiting computing device 1300 that may perform one or more of the above described methods and processes. Computing device 1300 is shown in simplified form. It is to be understood that virtually any computer architecture may be used without departing from the scope of this disclosure. In different embodiments, computing device 1300 may take the form of a mainframe computer, server computer, desktop computer, laptop computer, tablet computer, home entertainment computer, network computing device, mobile computing device, mobile communication device, gaming device, etc.

Computing device 1300 includes a logic subsystem 1302 and a data-holding subsystem 1304. Computing device 1300 may optionally include a display subsystem 1306, communication subsystem 1308, and/or other components not shown in FIG. 13. Computing device 1300 may also optionally include user input devices such as keyboards, mice, game controllers, cameras, microphones, and/or touch screens, for example.

Logic subsystem 1302 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1304 may include one or more physical, non-transitory, devices configured to hold data and/or instructions executable by the logic subsystem to implement the herein described methods and processes. When such methods and processes are implemented, the state of data-holding subsystem 1304 may be transformed (e.g., to hold different data).

Data-holding subsystem 1304 may include removable media and/or built-in devices. Data-holding subsystem 1304 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1304 may include devices with one or more of the following characteristics: volatile, nonvolatile, dynamic, static, read/write, read-only, random access, sequential access, location addressable, file addressable, and content addressable. In some embodiments, logic subsystem 1302 and data-holding subsystem 1304 may be integrated into one or more common devices, such as an application specific integrated circuit or a system on a chip.

FIG. 13 also shows an aspect of the data-holding subsystem in the form of removable computer-readable storage media 1310, which may be used to store and/or transfer data and/or instructions executable to implement the herein described methods and processes. Removable computer-readable storage media 1310 may take the form of CDs, DVDs, HD-DVDs, Blu-Ray Discs, EEPROMs, and/or floppy disks, among others.

It is to be appreciated that a "service", as used herein, may be an application program executable across multiple user sessions and available to one or more system components, programs, and/or other services. In some implementations, a service may run on a server responsive to a request from a client.

When included, display subsystem 1306 may be used to present a visual representation of data held by data-holding subsystem 1304. As the herein described methods and processes change the data held by the data-holding subsystem, and thus transform the state of the data-holding subsystem, the state of display subsystem 1306 may likewise be transformed to visually represent changes in the underlying data. Display subsystem 1306 may include one or more display devices utilizing virtually any type of technology. Such display devices may be combined with logic subsystem 1302 and/or data-holding subsystem 1304 in a shared enclosure, or such display devices may be peripheral display devices.

When included, communication subsystem 1308 may be configured to communicatively couple computing device 1300 with one or more other computing devices. Communication subsystem 1308 may include wired and/or wireless communication devices compatible with one or more different communication protocols. As nonlimiting examples, the communication subsystem may be configured for communication via a wireless telephone network, a wireless local area network, a wired local area network, a wireless wide area network, a wired wide area network, etc. In some embodiments, the communication subsystem may allow computing device 1300 to send and/or receive messages to and/or from other devices via a network such as the Internet.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention claimed is:

1. A computer-implemented method for determining a level of cellular metabolic activity for a region of interest in a brain of a subject, comprising:
  receiving, with one or more processors of a computing device, a first set of Dynamic Contrast Enhanced Magnetic Resonance Imaging (DCE-MRI) time-course data obtained with a Magnetic Resonance Imaging (MRI) device for the brain of the subject, wherein the first set of DCE-MRI time-course data is obtained with the MRI device after administration of a contrast agent to the subject;
  identifying, with the one or more processors of the computing device, the region of interest in the brain from the first set of DCE-MRI time-course data for further analysis;
  determining, with the one or more processors of the computing device, a first mean water molecule capillary lifetime value ($\tau_b$) in the region of interest using shutter-speed pharmacokinetic (SSP) analysis of the first set of DCE-MRI time-course data; and
  determining, with the one or more processors of the computing device, a level of cellular metabolic activity in the region of interest of the brain based on the first mean water molecule capillary lifetime value.

2. The method of claim 1, wherein the cellular metabolic activity comprises Na+/K+ ATPase activity.

3. The method of claim 1, further comprising:
indicating a decrease in Na+/K+ ATPase activity when the first mean water molecule capillary lifetime value increases relative to a threshold; and
indicating an increase in Na+/K+ ATPase activity when the first mean water molecule capillary lifetime value decreases relative to the threshold.

4. The method of claim 1, further comprising outputting, with the one or more processors of the computing device, a map of the region of interest of the brain to a display device based on an inverse of the first mean water molecule capillary lifetime value.

5. The method of claim 1, further comprising determining, with the one or more processors of the computing device, a blood volume fraction using SSP analysis of the first set of DCE-MRI time-course data.

6. The method of claim 5, further comprising estimating, with the one or more processors of the computing device, individual capillary radii based on the blood volume fraction.

7. The method of claim 1, further comprising calculating, with the one or more processors of the computing device, an equilibrium water efflux from brain capillaries in the region of interest of the brain based on an estimated average capillary length and radius and the first mean water molecule capillary lifetime value.

8. The method of claim 1, further comprising:
receiving, with the one or more processors of the computing device, a second set of DCE-MRI time-course data for the region of interest in the brain, wherein the second set of DCE-MRI time-course data is obtained after the region of interest in the brain has been treated;
determining, with the one or more processors of the computing device, a second mean water molecule capillary lifetime value (m) in the region of interest of the brain using SSP analysis of the second set of DCE-MRI time-course data;
determining, with the one or more processors of a computing device, a second level of cellular metabolic activity in the brain based on the second mean water molecule capillary lifetime value; and
calculating, with the one or more processors of a computing device, a difference between the level of cellular metabolic activity in the brain based on the first mean water molecule capillary lifetime value and the second level of cellular metabolic activity in the brain based on the second mean water molecule capillary lifetime value.

9. The method of claim 1, further comprising determining the presence of, with the one or more processors of the computing device, a cerebral pathology based on the first mean water molecule capillary lifetime.

10. The method of claim 9, wherein determining the presence of the cerebral pathology comprises determining a glioblastoma multiforme condition based on the level of cellular metabolic activity in the region of interest of the brain.

11. The method of claim 9, wherein determining the cerebral pathology comprises determining a multiple sclerosis condition based on the level of cellular metabolic activity in the region of interest of the brain.

12. The method of claim 11, further comprising determining, with the one or more processors of the computing device, a first multiple sclerosis brain condition in response to the first mean water molecule capillary lifetime value having a value greater than a first threshold; and
providing, with the one or more processors of the computing device, an indication of a second multiple sclerosis brain condition in response to the first mean water molecule capillary lifetime value having a value greater than a second threshold, where the second threshold is larger than the first threshold.

13. The method of claim 12, wherein the first multiple sclerosis brain condition is a normal-appearing multiple sclerosis brain condition and the second multiple sclerosis brain condition is a multiple sclerosis lesion condition and/or a glioblastoma multiforme tumor condition.

14. The method of claim 12, further comprising providing, with the one or more processors of the computing device, an indication of an advanced stage multiple sclerosis brain condition in response to the first mean water molecule capillary lifetime value having a value less than a third threshold, where the third threshold is less than the first threshold.

15. The method of claim 1, wherein the first mean water molecule capillary lifetime value in the region of interest of the brain is obtained via non-linear modeling.

16. The method of claim 1, wherein the cellular metabolic activity comprises neuroglial and/or neuronal metabolic activity.

* * * * *

UNITED STATES PATENT AND TRADEMARK OFFICE
CERTIFICATE OF CORRECTION

| | |
|---|---|
| PATENT NO. | : 10,335,048 B2 |
| APPLICATION NO. | : 14/543071 |
| DATED | : July 2, 2019 |
| INVENTOR(S) | : William Rooney, Charles Springer, Jr. and Xin Li |

Page 1 of 1

It is certified that error appears in the above-identified patent and that said Letters Patent is hereby corrected as shown below:

In the Specification

Column 1, Lines 16 to 20, within the ACKNOWLEDGEMENT OF GOVERNMENT SUPPORT, replace:
"This invention was made with Government support under Grant Nos. R01-EB007258, RO1-NS40801, and UO1 CA-154602 awarded by The National Institutes of Health. The United States Government has certain rights in the invention."

With the following:
--This invention was made with government support under NS040801 awarded by the National Institutes of Health. The government has certain rights in the invention.--

Signed and Sealed this
Seventeenth Day of January, 2023

Katherine Kelly Vidal
*Director of the United States Patent and Trademark Office*